United States Patent
Tamayo et al.

(10) Patent No.: US 9,865,821 B2
(45) Date of Patent: Jan. 9, 2018

(54) ORGANIC SEMICONDUCTING COMPOUNDS FOR USE IN ORGANIC ELECTRONIC DEVICES

(71) Applicant: Next Energy Technologies, Inc., Santa Barbara, CA (US)

(72) Inventors: Arnold B. Tamayo, Santa Barbara, CA (US); Corey V. Hoven, Santa Barbara, CA (US); Thomas K. Wood, Santa Barbara, CA (US); Braden Smith, Santa Barbara, CA (US)

(73) Assignee: Next Energy Technologies, Inc., Santa Barbara, CA (US)

(*) Notice: Subject to any disclaimer, the term of this patent is extended or adjusted under 35 U.S.C. 154(b) by 0 days.

(21) Appl. No.: 14/379,468

(22) PCT Filed: Feb. 19, 2013

(86) PCT No.: PCT/US2013/026718
§ 371 (c)(1),
(2) Date: Aug. 18, 2014

(87) PCT Pub. No.: WO2013/123508
PCT Pub. Date: Aug. 22, 2013

(65) Prior Publication Data
US 2015/0034161 A1    Feb. 5, 2015

Related U.S. Application Data

(60) Provisional application No. 61/600,307, filed on Feb. 17, 2012.

(51) Int. Cl.
| | | |
|---|---|---|
| C07D 513/04 | (2006.01) |
| C07F 7/10 | (2006.01) |
| H01L 51/00 | (2006.01) |
| C07F 7/08 | (2006.01) |
| B82Y 10/00 | (2011.01) |
| C08G 61/12 | (2006.01) |
| H01L 51/42 | (2006.01) |

(52) U.S. Cl.
CPC .......... *H01L 51/0071* (2013.01); *B82Y 10/00* (2013.01); *C07D 513/04* (2013.01); *C07F 7/0807* (2013.01); *C07F 7/0816* (2013.01); *C07F 7/10* (2013.01); *C08G 61/126* (2013.01); *H01L 51/0035* (2013.01); *H01L 51/0068* (2013.01); *H01L 51/0094* (2013.01); *H01L 51/42* (2013.01); *C08G 2261/3243* (2013.01); *C08G 2261/3246* (2013.01); *C08G 2261/91* (2013.01); *H01L 51/0047* (2013.01); *H01L 51/4253* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 8,227,691 B2 | 7/2012 | Bazan et al. | |
| 8,273,599 B2 | 9/2012 | Bazan et al. | |
| 8,318,532 B2 | 11/2012 | Bazan et al. | |
| 8,723,169 B2 | 5/2014 | Bazan et al. | |
| 2005/0026927 A1* | 2/2005 | Boettcher | C07D 403/06 514/253.06 |
| 2006/0052612 A1 | 3/2006 | Stossel | |
| 2006/0134425 A1 | 6/2006 | Suzuki et al. | |
| 2006/0292736 A1 | 12/2006 | Lee et al. | |
| 2007/0169816 A1 | 7/2007 | Lee et al. | |
| 2007/0221926 A1 | 9/2007 | Lee et al. | |
| 2008/0315187 A1 | 12/2008 | Bazan et al. | |
| 2009/0032808 A1 | 2/2009 | Bazan et al. | |
| 2009/0108255 A1 | 4/2009 | Bazan et al. | |
| 2009/0126779 A1 | 5/2009 | Heeger et al. | |
| 2009/0188558 A1 | 7/2009 | Jen et al. | |
| 2010/0252112 A1 | 10/2010 | Watson | |
| 2010/0326525 A1 | 12/2010 | Nguyen et al. | |
| 2013/0032791 A1 | 2/2013 | Bazan et al. | |
| 2013/0240845 A1 | 9/2013 | Bazan et al. | |
| 2013/0247990 A1 | 9/2013 | Facchetti | |
| 2014/0167002 A1* | 6/2014 | Welch | C07D 498/04 257/40 |

FOREIGN PATENT DOCUMENTS

| | | |
|---|---|---|
| CN | 101504971 A | 8/2009 |
| EP | 2407464 A1 | 1/2012 |
| EP | 2597127 A1 | 5/2013 |
| FR | 2910277 * | 6/2008 |
| WO | WO2010/052448 A2 * | 5/2010 |
| WO | WO-2011/049531 A1 | 4/2011 |
| WO | WO-2011/060526 A1 | 5/2011 |
| WO | WO2012/008556 A1 * | 1/2012 |
| WO | WO 2012/074853 | 6/2012 |

(Continued)

OTHER PUBLICATIONS

Thomas, A., & Sliwa, W., 20(6) Heterocycles 1043-1048 (1983).*
Greiner et al., "Universal energy-level alignment of molecules on metal oxides," 2011 Nature Materials, DOT: 10.1038/NMAT3159, pp. 76-81.
Guenes et al., "Photovoltaic characterization of hybrid solar cells using surface modified TiO2 nanoparticles and poly(3-hexyl)thiophene," 2008 Nanotechnology 19 424009.
O'Regan et al., "A low-cost, high-efficiency solar cell based on dye-sensitized colloidal TiO2 films," 1991 Nature 353:737.
Zhuo et al, "Enhanced Photovoltaic Performance of Low-Bandgap Polymers with Deep LUMO Levels," 2010 Angewandte Chemie, International Edition, vol. 49, No. 43, pp. 7992-7995, S7992/1-S7992/11.
Yuze Lin et al: "Small molecule semiconductors for high-efficiency organic photovoltaics", Chem. Soc. Rev., vol. 41, No. 11, Jan. 1, 2012 (Jan. 1, 2012), p. 4245-4272.

(Continued)

*Primary Examiner* — Timothy R Rozof
(74) *Attorney, Agent, or Firm* — Venable LLP; Henry J. Daley; Annette K. Kwok

(57) ABSTRACT

Organic molecule semi-conducting chromophores containing a halogen-substituted core structure are disclosed. Such compounds can be used in organic heterojunction devices, such as organic molecule solar cells and transistors.

39 Claims, 1 Drawing Sheet

(56) References Cited

FOREIGN PATENT DOCUMENTS

| WO | WO 2012/178116 | 12/2012 |
| WO | WO 2013/142850 | 9/2013 |

OTHER PUBLICATIONS

Zhou et al., "Development of Fluorinated Benzothiadiazole as a Structural Unit for a Polymer Solar Cell of 7% Efficiency," Angewandte Chemie International Edition, vol. 50, No. 13, Mar. 2, 2011, pp. 2995-2998.
Price et al., "Fluorine Substituted Conjugated Polymer of Medium Band Gap Yields 7% Efficiency in Polymer—Fullerene Solar Cells", Journal of the American Chemical Society, American Chemical Society, US, vol. 133, No. 12, Mar. 30, 2011 (Mar. 30, 2011), pp. 4625-4631.
Sanghyun Paek et al: "Efficient Organic Semiconductors Containing Fluorine-Substituted Benzothiadiazole for Solution-Processed Small Molecule Organic Solar Cells", Journal of Physical Chemistry C, vol. 116, No. 44, Oct. 22, 2012 (Oct. 10, 2012), pp. 23205-23213, XP055207197,.
Amaresh Mishra et al: "Small Molecule Organic Semiconductors on the Move: Promises for Future Solar Energy Technology", Angewandte Chemie International Edition, vol. 51, No. 9, Feb. 27, 2012 (Feb. 27, 2012), pp. 2020-2067, XP055131346.
Extended European Search Report in European Patent Application No. 13748582.7, dated Aug. 19, 2015.
Notification of the First Office Action in Chinese Application No. 2015102901546720, dated Nov. 3, 2015.
Zhang et al., "Increased Open Circuit Voltage in Fluorinated Benzothiadiazole-based Alternating Conjugated Polymers," Chemical Communications, vol. 47, No. 39, Jan. 1, 2011, p. 11026.
Zhang et al., "Solution-Processable Star-Shaped Photovoltaic Organic Molecule with Triphenylamine Core and Benzothiadiazole-Thiophene Arms," Macromolecules, vol. 42, No. 20, Oct. 27, 2009, pp. 7619-7622.
International Search Report in International Application No. PCT/US2013/033615, dated Jul. 16, 2013.
International Search Report in International Application No. PCT/US2013/25936, dated Feb. 14, 2012.
Takacs et al., "Solar Cell Efficiency, Self-Assembly, and Dipole-Dipole Interactions of Isomorphic Narrow-Band-Gap Molecules," AM. Chem. Soc., 2012, vol. 134, pp. 16597-16606.
Gupta et al., "Barium: An Efficient Cathode Layer for Bulk-heterojunction Solar Cells," Scientific Reports, vol. 3, 1965, pp. 1-6.
Kyaw et al., "Improved Light Harvesting and Improved Efficiency by Insertion of an Optical Spacer (ZnO) in Solution-Processed Small-Molecule Solar Cells," Nano Lett., 2013, vol. 13, pp. 3796-3801.
"Electronic." Merriam-Webster.com. Merriam-Webster, n.d. Web. Dec. 5, 2016.
Blouin, N. et al. (Sep. 19, 2007, e-pub. Dec. 21, 2007). "Toward a Rational Design of Poly (2,7-Carbazole) Derivatives for Solar Cells," Journal of the American Chemical Society, 130:732-742.
Chen, J.J.A. et al. (2010, e-pub. Aug. 30, 2010). "Auinacridone-Based Molecular Donors for Solution Processed Bulk-Heterojunction Organic Solar Cells," ACS Applied Materials & Interfaces, 2(9)2679-2686.

Coffin, R.C., et al. (Nov. 2009, e-pub. Oct. 18, 2009). "Streamlined Microwave-Assisted Preparation of Narrow-Bandgap Conjugated Polymers for High-Performance Bulk Heterojunction Solar Cells," Nat. Chem. 1:657-661.
Hau, S.K. et al. (Nov. 6, 2010). "A Review on the Development of the Inverted Polymer Solar Cell Architecture," Polymer Reviews, 50(4):474-510.
Henson, Z. B. et al., (Oct. 4, 2011, e-pub. Jan. 27, 2012). "Pyridalthiadiazole-Based Narrow Band Gap Chromophores," J. Am. Chem. Soc. 134(8):3766-3779.
International Search Report dated Jul. 17, 2013, for PCT Patent Application No. PCT/US2013/033615, filed Mar. 22, 2013, 4 pages.
Kyaw, A.K.K. et al. (Jun. 27, 2013). "Improved Light Harvesting and Improved Efficiency by Insertion of an Optical Spacer (ZnO) in Solution-Processed Small-Molecule Solar Cells," Nano Lett., 13:3796-3801.
Leroy, J. et al. (Sep. 28, 2006, e-pub. Jan. 17, 2007). "Symmetrical and Nonsymmetrical Liquid Crystalline Oligothiophenes: Convenient Synthesis and Transition-Temperature Engineering," Eur. J. Org <http://Eur.J.Org>. Chem., 1256-1261.
Love, J.A. et al. (2013). "Film Morphology of High Efficiency Solution-Processed Small-Molecule Solar Cells," Adv. Funct. Matter, 23:5019-5026.
Peng, Q. et al., (2011). "Novel Benzo [1,2-b:4,5-5 ] dithiophene-Benzothiadiazole Derivatives with Variable Side Chains for High-Performance Solar Cells," Adv. Mater. 23:4554-4558.
Perez, L.A. et al. (May 25, 2013, e-pub. Sep. 4, 2013). "Solvent Additive Effects on Small Molecule Crystallization in Bulk Heterojunction Solar Cells Probed During Spin Casting," Adv. Mater., 25:6380-6384.
Sharif, M. et al., (Feb. 2, 2010, e-pub. Mar. 20, 2010). "One-Pot Synthesis of Fluorinated Terphenyls by Site-Selective Suzuki-Miyaura Reactions of 1,4-Dibromo-2-Fluorobenzene," Teterahedron Letters, 51:2810-2812.
Sun, Y. et al., (Jan. 2012, e-pub. Nov. 6, 2011). "Solution-Processed Small-Molecule Solar Cells with 6.7% Efficiency," Nat. Mater. 11:44-48.
Van der Poll, T.S. et al. (Mar. 19, 2012, e-pub. Jun. 6, 2012). "Non-Basic High-Performance Molecules for Solution-Processed Organic Solar Cells," Adv. Mater., 24:3646-3649.
Welch, G. C. et al., (Mar. 4, 2011). "Lewis Acid Adducts of Narrow Band Gap Conjugated Polymers," J. Am. Chem. Soc., 133:4632-4644.
Welch, G.C. et al., (2011). "A Modular Molecular Framework for Utility in Small-Molecule Solution-Processed Organic Photovoltaic Devices," J. of Matter. Chem., 21:12700-12709.
Written Opinion dated Jul. 16, 2013, for PCT Application No. PCT/US2013/033615, Internationally filed on Mar. 22, 2013, 6 pages.
Notification of the First Office Action in Chinese Patent Application No. 201380019851.4, dated Nov. 3, 2015.
Notification of the Second Office Action in Chinese Patent Application No. 201380019851.4, dated Aug. 4, 2016.
Office Action in European Patent Application No. EP 13748582.7, dated Sep. 29, 2016.

* cited by examiner

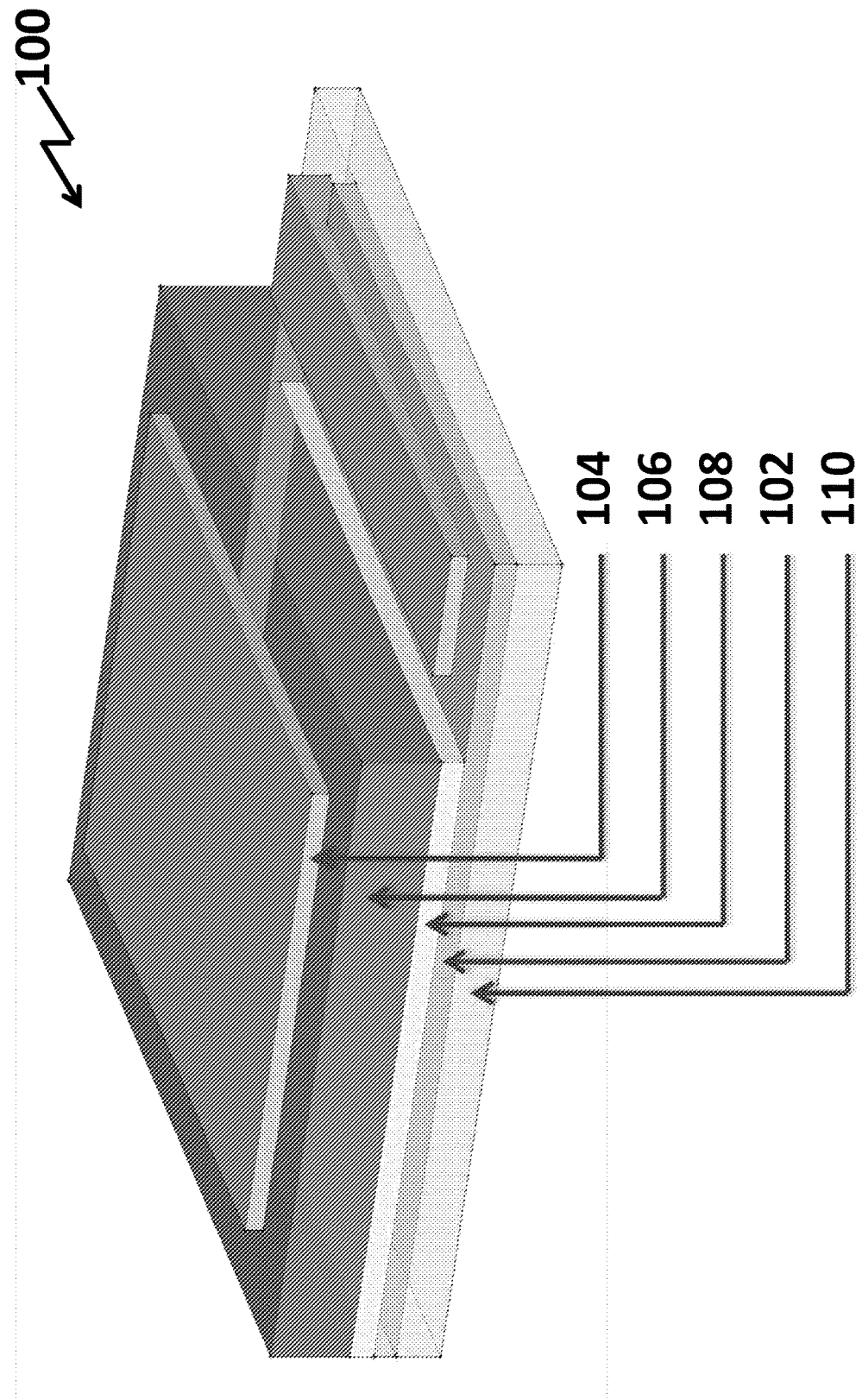

ORGANIC SEMICONDUCTING COMPOUNDS FOR USE IN ORGANIC ELECTRONIC DEVICES

CLAIM OF PRIORITY

This application is a national stage of PCT/US2013/026718, filed Feb. 19, 2013, which claims priority to provisional U.S. application No. 61/600,307, filed Feb. 17, 2012, each of which is incorporated by reference in its entirety.

BACKGROUND

Solution-processed organic photovoltaic devices (OPV) have emerged as a promising energy technology due to their ease of processing, low-cost, and ability to be fabricated onto light-weight flexible substrates. Polymer based OPV's have by far been the most studied, and power conversion efficiencies (PCE's) above 6% have recently been reported for polymer:fullerene bulk heterojunction (BHJ) devices. On the other hand, solution processed small molecule BHJ devices have received far less attention. Such molecular heterojunctions (MHJ) have several advantages over their polymer counterparts, in that small molecules have well defined structures, are easily functionalized, are monodisperse, are readily purified, and do not suffer from batch-to-batch variations. Reports of efficient solution processed MHJ devices have recently emerged that have utilized merocyanine dyes, squaraine dyes, isoindigo, and diketopyrrolopyrrole based chromophores as the light harvesting donor component with a fullerene acceptor. PCE's have reached upwards of 4% for such devices. While these results are encouraging, there still exits a need for the development of novel discrete light harvesting materials. Key parameters for effective small molecule donors include having broad and efficient optical absorption that extends into the near-IR region to maximize photon absorption, deep HOMO levels from −5 to −5.5 eV to maximize open circuit voltages, relatively planar structures for high charge carrier mobility, high solution viscosity and solubilizing side chains for solution to film processing. Additionally, it is important that novel structures have facile and highly tunable syntheses to enable rapid and cheap generation of molecular libraries.

The present invention seeks to address the need for improved light harvesting molecules and molecular heterojunction devices by providing novel and advantageous materials and their use in such devices.

SUMMARY

In one embodiment, the present invention is directed to organic semiconducting compounds containing halogen-substituted pyroidothiadiazole (PT, [1,2,5]thiadiazolo[3,4-c]pyridine), pyridooxadizaole (PO, [1,2,5]oxadiazolo[3,4-c]pyridine), pyridotriazole (P3N, 2H-[1,2,3]triazolo[4,5-c]pyridine), pyridoselenadiazole (PSe, [1,2,5]selenadiazolo[3,4-c]pyridine), pyridotelluradiazole (PTe, [1,2,5]telluradiazolo[3,4-c]pyridine), 2,3-dihydropyrido[3,4-b]pyrazine, and pyrido[3,4-b]pyrazine structures for use in heterojunction devices, such as organic solar cells and transistors. In one embodiment, the present invention is directed to electron-donating and electron-accepting chromophores having a halogen-substituted pyroidothiadiazole (PT, [1,2,5]thiadiazolo[3,4-c]pyridine), pyridooxadizaole (PO, [1,2,5]thiadiazolo[3,4-c]pyridine), 2-substituted pyridotriazole (P3N, 2H-[1,2,3]triazolo[4,5-c]pyridine), pyridoselenadiazole (PSe, [1,2,5]selenadiazolo[3,4-c]pyridine), core structure. In other embodiments, the present invention is directed to optoelectronic devices comprising a first electrode, a second electrode and an active layer between the two electrodes containing a compound described herein.

Embodiments include compounds comprising one or more groups of Formula A:

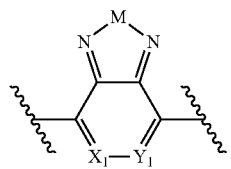

Formula A where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N–R$_1$)—; where R$_6$ is H or a substitutent; R$_7$ is H or a substituent; and R$_8$ is H or a substituent. X$_1$ is N or C—R$_9$, Y$_1$ is N or C—R$_9$, and one of X$_1$ and Y$_1$ is N, and the other is C—R$_9$; where R$_9$ is F, Cl, Br, or I.

Embodiments include electronic or optoelectronic devices comprising a non-polymeric compound of Formula A.

BRIEF DESCRIPTION OF THE DRAWINGS

FIG. 1 is a schematic illustration of an example device according to an embodiment of the invention.

DETAILED DESCRIPTION

Definitions

The terms "alkyl" used alone or as part of a larger moiety (i.e. "alkoxy," "hydroxyalkyl," "alkoxyalkyl," and "alloxycarbonyl") include both straight and branched saturated hydrocarbon chains containing one to sixteen carbon atoms (i.e. 1, 2, 3, 4, 5, 6, 7, 8, 9, 10, 11, 12, 13, 14, 15, or 16 carbon atoms), as well as cyclic structures. Alkyl groups may be independently defined between any two endpoints within this range, so that a particular alkyl group may have, for example, 1 to 12 carbons, 1 to 6 carbons, 1 to 4 carbons, 6-16 carbons, 6-12 carbons, and so forth. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkoxy" refers to an —O-alkyl radical, such as, for example —O-Me, —O-Et, —O—Pr, and so on. The term "hydroxyalkyl" refers to an alkyl group substituted with one or more hydroxyl, such as, for example, hydroxymethyl, 1-hydroxyethyl, 2-hydroxyethyl, 1,2-dihydroxyethyl, and so forth. The term "alkylthio" refers to an —S-alkyl group, such as, for example, example —S-Me, —S-Et, —S—Pr. The term "haloalkyl" means alkyl, substituted with one or more halogen atoms, such as trifluoromethyl, chloromethyl, 2,2,2-trifluoroethyl, 1,1,2,2,2-petanfluoroethyl, and so on, and includes "fluoroalkyl," where at least one carbon atom in the alkyl chain is substituted with fluorine, and perfluoro alkyl, where all hydrogen atoms on the alkyl chain are replaced with fluorine. The term "aminoalkyl" means alkyl, substituted with an amine group ($NH_2$), such as, for example, aminomethyl, 1-aminoethyl, 2-aminoethyl, 3-aminopropyl and so forth. The term "alkoxyalkyl" refers to an alkyl group, substituted with an alkoxy group, such as, for example, methoxymethyl, ethoxymethyl, methoxyethyl, and so forth. As used herein, the term "alkylaminoalkyl" refers to an allyl group substituted with an alkylamine group, such as, for example, N-methylaminomethyl, N,N-dimethylaminomethyl, N,N-methylpentylaminomethyl, 2-(N-methylamino)ethyl, 2-(N,N-dimethylamino)ethyl, and so forth.

The term "halogen" or "halo" means F, Cl, Br, or I.

The term "nitro" means (—$NO_2$).

The term "hydroxy" or "hydroxyl" means —OH.

The term "amine" or "amino" used alone or as part of a larger moiety refers to unsubstituted (—$NH_2$). The term "alkylamine" refers to mono- (—NRH) or di-substituted (—$NR_2$) amine where at least one R group is an alkyl substituent, as defined above. Examples include methylamino (—$NHCH_3$), dimethylamino (—$N(CH_3)_2$), The term "arylamine" refers to a mono (—NRH) or di-substituted (—$NR_2$) amine, where at least one R group is an aryl group as defined below, including, for example, phenylamino, diphenylamino, and so forth. The term "heteroarylamine" refers to a mono (—NRH) or di-substituted (—$NR_2$) amine, where at least one R group is a heteroaryl group as defined below, including, for example, 2-pyridylamino, 3-pyridylamino and so forth. The term "aralkylamine" refers to a mono (—NRH) or di-substituted (—$NR_2$) amine, where at least one R group is an aralkyl group, including, for example, benzylamino, phenethylamino, and so forth. The term "heteroaralkylamine" refers to a mono (—NRH) or di-substituted (—$NR_2$) amine, where at least one R group is a heteroaralkyl group. As used herein, the term "alkylaminoalkyl" refers to an alkyl group substituted with an alkylamine group. Analogously, "arylaminoalkyl" refers to an alkyl group substituted with an arylamine, and so forth, for any substituted amine described herein.

The term "alkenyl" used alone or as part of a larger moiety include both straight and branched chains containing at least one double bond and two to sixteen carbon atoms (i.e. 2, 3, 4, 5, 6, 7, 8, 9, 10, 11, 12, 13, 14, 15, or 16 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "aryl" used alone or as part of a larger moiety, refers to mono-, bi-, tri-, or larger aromatic hydrocarbon ring systems having five to thirty members. Aryl groups may be independently defined between any two endpoints within this range, so that a particular aryl group may have, for example, 5 to 24 members, 6 to 24 members, 6 to 14 members, 10 to 30 members, and so forth. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, and including spiro compounds, such as spirobi[fluorene], where the radical or point of attachment is on the aromatic ring. The term "aralkyl" refers to an alkyl substituent substituted by an aryl group. The term "aryloxy" refers to an —O-aryl group, such as, for example phenoxy, 4-chlorophenoxy and so forth. The term "arylthio" refers to an —S-aryl group such as, for example phenylthio, 4-chlorophenylthio, and so forth. The term "aryl" used alone or as part of a larger moiety also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, 5 or more substituents. The substituents may the same or different. Substituents on an aryl group include hydrogen, halogen, alkyl, alkenyl, nitro, hydroxyl, amino, alkylamino, alkoxy, and alkylthio, acyl, O-acyl, N-acyl, S-acyl as defined herein.

The term "heteroaryl", used alone or as part of a larger moiety, refers to heteroaromatic ring groups having five to thirty members, in which one or more ring carbons (1 to 6, 1 to 4, 1 to 3, 1 to 2, or 1), are each replaced by a heteroatom such as N, O, S, or Si. Heteroaryl groups may be independently defined between any two endpoints within this range, so that a particular heteroaryl group may have, for example, 5 to 24 members, 6 to 24 members, 6 to 14 members, 10 to 30 members, and so forth. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, benzoisoxazolyl. Other specific examples include thiophene, pyrrole, furan, phosphole, benzodithiophene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene where R and R'=$C_1$-$C_{30}$ alkyl or $C_6$-$C_3$ aryl. Also included within the scope of the term "heteroaryl", as it is used herein, is a group in which a heteroaromatic ring is fused to one or more aromatic or nonaromatic rings, including spiro compounds, where the radical or point of attachment is on the heteroaromatic ring. Examples include tetrahydroquinolinyl, tetrahydroisoquinolinyl, pyrido[3,4-d]pyrimidinyl, spirobi[dibenzo[b,c]silole], spirobi[cyclopenta[1,2-b:5,4-b']dithiophene], or spirobi[silolo[3,2-b:4,5-b']dithiophene]. The term "heteroaryl" may be used interchangeably with the term "heteroaryl ring" or the term "heteroaromatic." The term "heteroaralkyl" refers to an alkyl group substituted by a heteroaryl, such as, for example, 2-pyridylmethyl, 3-pyridylmethyl, 1-imidazolomethyl, 2-imidazolomethyl and so forth. The term "heteroaryloxy" refers to an —O-heteroaryl group. The term "heteroarylthio" refers to an —S-aryl group. A heteroaryl group may have more than one substituent, up to the total number of free substitution positions. For example, a heteroaryl group may have 1, 2, 3, 4, or 5 substituents. The substituents may be the same or different. Substituents on a heteroaryl group include hydrogen, halogen, alkyl, alkenyl, nitro, hydroxyl, amino, alkylamino, alkoxy, and alkylthio, acyl, O-acyl, N-acyl, S-acyl as defined herein.

The term "acyl" refers to an "—C(O)-alkyl," "C(O)-aryl," or "C(O)-heteroaryl" group. The term "O-acyl" refers to an "—O—C(O)-alkyl," "—O—C(O)-aryl," or "—O—C(O)—heteroaryl" group. The term "N-acyl" refers to an "—NR—C(O)-alkyl," "—NR—C(O)-aryl," or "—NR—C(O)-heteroaryl" where R is an alkyl, hydroxyl, or alkoxy group. The term "S-acyl" refers to "—S—C(O)-alkyl," "—S—C(O)-aryl," or "—S—C(O)-heteroaryl." The term "N—O-acyl" refers to an "N—O—C(O)-alkyl," "N—O—C(O)-aryl," or "N—O—C(O)-heteroaryl" group.

As used herein, a "substituted" structure refers to a chemical structure where a hydrogen atom has been replaced by a substituent. A "substituent" is a chemical structure that replaces a hydrogen atom on the substituted structure, and may be, independently, any chemical moiety defined previously. When present, multiple substituents may be the same or different. The term "substituent" does not imply that the substituent is smaller than the substituted structure. In some embodiments, a "substituent" may be halogen, F, $NO_2$, CN, acyl, O-acyl, S-acyl, N-acyl, alkyl, haloalkyl, substituted or unsubstituted aryl, substituted or unsubstituted heteroaryl, alkenyl, alkoxy, alkylthio, alkylamine, arylamine, or hydroxy.

"Polymer" or "polymeric molecule" is defined herein as a structure containing at least eight repeating units. A "non-polymeric" molecule is a molecule containing seven or fewer repeating units. Thus, monomers, dimers, trimers, tetramers, pentamers, hexamers, and heptamers are non-polymeric molecules for the purposes of this disclosure. Interruption of a repeating unit "resets" the count of subunits for the purposes of this disclosure; thus, for example, for a molecule such as Formula 6:

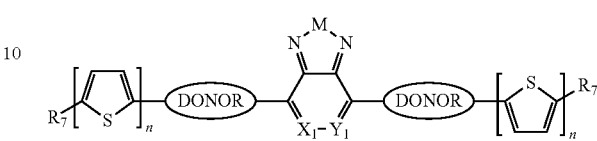

6 when n is 5, the molecule is considered to have two separate five-subunit pieces, that is, it is comprised of two pentamers of thiophene, and is not considered a decamer or 10-subunit polymer of thiophene.

Non-polymeric molecules have a discrete molecular weight, while polymeric molecules usually have a distribution of molecular weights due to varying numbers of monomers that are incorporated into the growing chain during polymerization. Thus, in one embodiment, a preparation of a non-polymer molecule will be characterized by a single molecular weight (where the molecular weight is averaged only over isotopic variation due to differing isotopes such as hydrogen, deuterium, carbon-12, carbon-13, etc.). In contrast, preparations of a polymeric molecule will have a distribution of molecular weights due to varying numbers of monomers in the final polymer, where the molecular weight is an average over each individual polymeric species present in a given preparation (measured in either number-average molecular weight or weight-average molecular weight).

In some embodiments, the compounds are non-polymeric molecules. Compositions of the non-polymeric molecules described herein are not part of a mixture of oligomers or polymers. In other words, in some embodiments, compositions comprising the non-polymer molecules described herein will not contain oligomers or polymers having a repeating structure in common with the non-polymeric molecules described herein. In some embodiments, the non-polymer molecule is substantially pure, i.e. the molecules described herein may be greater than 90% pure, greater than 95% pure, or greater than 98% pure.

Organic Molecules

Some embodiments of the current invention provide several advantages for preparation of optoelectronic devices. The organic materials described may be non-polymeric allowing for synthesis and purification to be more repeatable than organic polymers. Unlike polymers, mono-disperse small molecules allow for their exact structure to be known and reproduced.

Organic compounds described herein may have favorable frontier molecular orbital levels (HOMO and LUMO) to accept and transport holes and electrons. The organic molecule compounds described also have favorable frontier molecular orbital levels (HOMO and LUMO) for use as electron donating materials in organic solar cell devices with fullerene, methanofullerene, rylene diimides or related π-conjugated organic electron acceptors. In addition, the organic molecule chromophores described have favorable frontier molecular orbital levels (HOMO and LUMO) for use as electron accepting materials in organic solar cell devices with thiophene or phenyl based π-conjugated organic electron donors.

The optical properties of the compounds are also very good. The organic molecule chromophores described have broad absorption spectra that absorb ultraviolet, visible, and near infrared radiation. The absorption spectra of the organic molecule chromophores described have a favorable spectral overlap with the terrestrial solar spectrum, making them excellent light harvesting materials for organic solar cells.

The compounds may also be readily handled in solution, as the organic molecules described retain good solubility in many common organic solvents. This allows solution processing during the preparation of the optoelectronic devices.

While solution processing may be advantageous for its ease of handling and low cost, vapor deposition can also be used, or mixtures of said molecules with other components, which are suitable for use in such a method (e.g., vacuum deposition, physical vapor deposition, chemical vapor deposition).

Embodiments include compounds comprising one or more groups of Formula A:

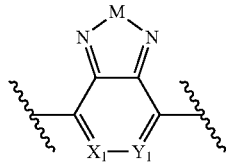

Formula A where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—; where $R_6$ is H or a substitutent; $R_7$ is H or a substituent; and $R_8$ is H or a substituent. $X_1$ is N or C—$R_9$, $Y_1$ is N or C—$R_9$, and one of $X_1$ and $Y_1$ is N, and the other is C—$R_9$; where $R_9$ is F, Cl, Br, or I.

In some embodiments, all $R_9$ substituents are F.

Because Formula A is asymmetric, the substructure of formula A may be replaced with either of the structures below in any compound described herein.

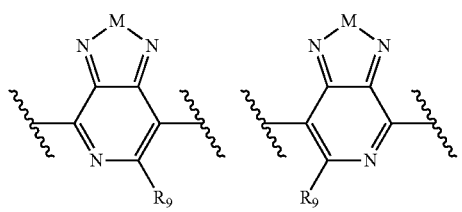

In some embodiments, the compound of formula A is a polymer.

Embodiments of the invention include compounds of Formula A having Formula B:

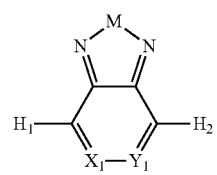

B where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—; where $R_6$ is H or a substitutent; $R_7$ is H or a substituent; and $R_8$ is H or a substituent. $X_1$ is N or C—$R_9$, $Y_1$ is N or C—$R_9$, and one of $X_1$ and $Y_1$ is N, and the other is C—$R_9$; where $R_9$ is F, Cl, Br, or I.

$H_1$ is selected from —$B_2$, -$A_1$-$B_1$, -$A_1$-$B_2$, or

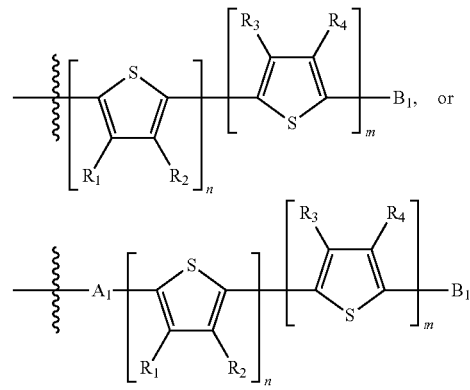

where n is an integer between 0 and 5, inclusive and m is an integer between 0 and 5, inclusive, and 1≤m+n≤5. $A_1$ is independently selected from substituted or unsubstituted aryl group, substituted or unsubstituted heteroaryl group,

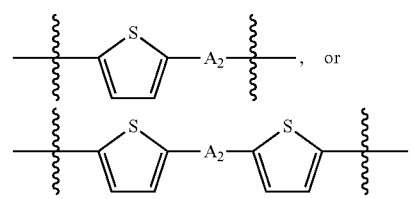

where $A_2$ is independently a substituted or unsubstituted aryl group or substituted or unsubstituted heteroaryl group. Each $B_1$ is independently selected from a an aryl or heteroaryl groups substituted with one, two, or more $B_2$. Each $B_2$ is independently selected from H, a substituent, halogen, —Sn($C_1$-$C_4$ allyl)$_4$, —Zn(halide), —Mg(halide), —B(OH)$_2$, or boronate ester, or

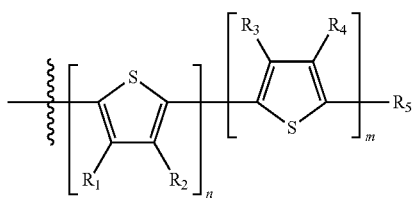

where n is an integer between 0 and 5, inclusive and m is an integer between 0 and 5, inclusive, and $1 \leq m+n \leq 5$. $R_1$, $R_2$, $R_3$, and $R_4$ are each independently H or a substituent, $R_5$ is H, a substituent, halogen, $-Sn(C_1-C_4\ alkyl)_3$, $-Zn(halide)$, $-Mg(halide)$, $-B(OH)_2$, or boronate ester.

$H_2$ is selected from $-B_2$, $-A_1-B_1$, $-A_1-B_2$,

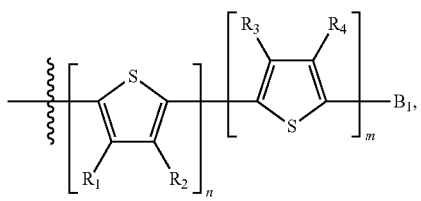

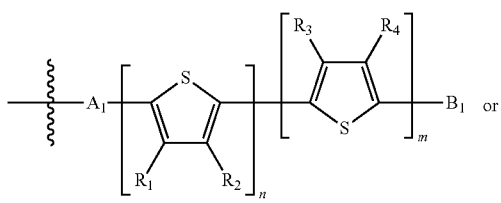

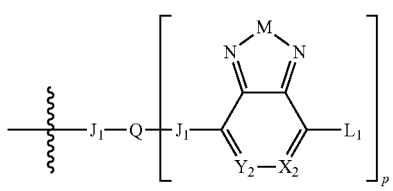

where p is 1, 2, or 3, n is an integer between 0 and 5, inclusive, and m is an integer between 0 and 5, inclusive, and $1 \leq m+n \leq 5$. Each $X_2$ is N or $C-R_9$, $Y_2$ is N or $C-R_9$, one of $X_2$ and $Y_2$ is N, and the other is $C-R_9$; where $R_9$ is F, Cl, Br, or I. Each $J_1$ is independently selected from a nonentity, substituted or unsubstituted aryl, substituted or unsubstituted heteroaryl groups, or

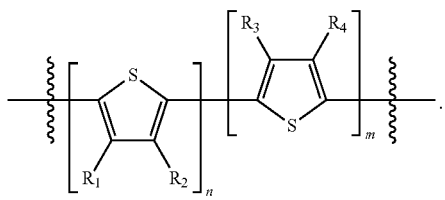

Q is a bivalent, trivalent, or tetravalent aryl or heteroaryl group or

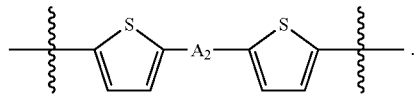

$L_1$ is selected from $-B_2$, $-A_1-B_1$, $-A_1-B_2$,

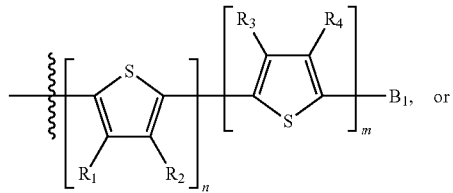

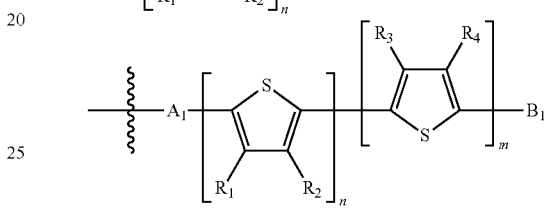

where each $A_1$ is independently selected from substituted or unsubstituted aryl group, substituted or unsubstituted heteroaryl group,

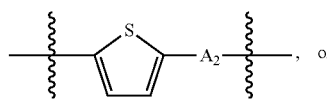

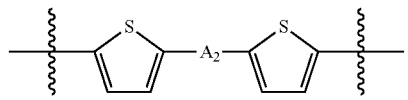

where $A_2$ is independently a substituted or unsubstituted aryl group or substituted or unsubstituted heteroaryl group.

In some compounds according to Formula B, M is S, O, or Se.

In some compounds according to Formula B, $H_1$ and $H_2$ are the same.

Some compounds according to Formula B have Formula III:

Formula III

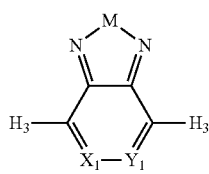

where M is selected from sulfur (S), oxygen (O), selenium (Se), tellurium (Te), $-N(R_6)-$, $-C(R_7)_2-C(R_8)_2-$, $-CR_7=CR_8-$, $-S(=O)_2-$, $-S(=O)-$, $-C(=O)-$, $-C(=S)-$, or $-C(=N-R_1)-$; where $R_6$ is H or a substitutent; $R_7$ is H or a substituent; and $R_8$ is H or a substituent. $X_1$ is N or C—$R_9$, $Y_1$ is N or C—$R_9$, and one of $X_1$ and $Y_1$ is N, and the other is C—$R_9$; where $R_9$ is F, Cl, Br, or I.

$H_3$ is selected from -$A_1$-$B_1$, -$A_1$-$B_2$, or

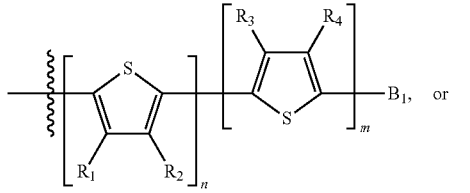

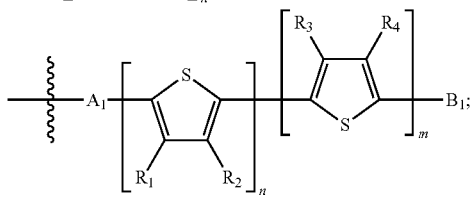

where n is an integer between 0 and 5, inclusive and m is an integer between 0 and 5, inclusive, and $1 \le m+n \le 5$.

Each $A_1$ is independently selected from substituted or unsubstituted aryl group, substituted or unsubstituted heteroaryl group,

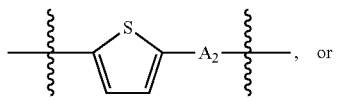

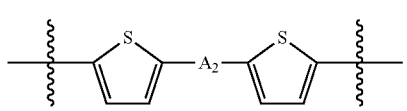

where $A_2$ is independently a substituted or unsubstituted aryl group or substituted or unsubstituted heteroaryl group. Each $B_1$ is independently selected from a an aryl or heteroaryl groups optionally substituted with one, two, or more $B_2$. Each $B_2$ is independently selected from H, a substituent, halogen, —Sn($C_1$-$C_4$ alkyl)$_4$, —Zn(halide), —Mg(halide), —B(OH)$_2$, or boronate ester, or

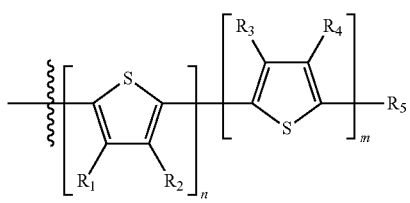

where n is an integer between 0 and 5, inclusive and m is an integer between 0 and 5, inclusive, and $1 \le m+n \le 5$. $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

Some compounds of Formula A or Formula B or Formula III have the formula:

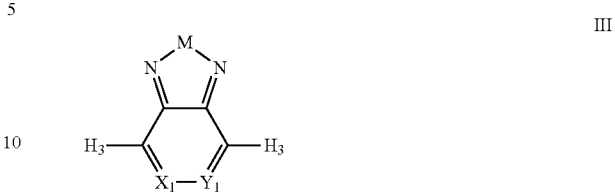

where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N–$R_1$)—; where $R_6$ is H or a substitutent; $R_7$ is H or a substituent; and $R_8$ is H or a substituent. $X_1$ is N or C—$R_9$, $Y_1$ is N or C—$R_9$, and one of $X_1$ and $Y_1$ is N, and the other is C—$R_9$; where $R_9$ is F, Cl, Br, or I.

$H_3$ is —$B_2$ and each $B_2$ is independently selected from H, a substituent, F, Cl, Br, I, —Sn($C_1$-$C_4$ alkyl)$_3$, —Zn(halide), —Mg(halide), —B(OH)$_2$, or boronate ester.

In some compounds according to formula III, $H_3$ is -$A_1$-$B_2$, or

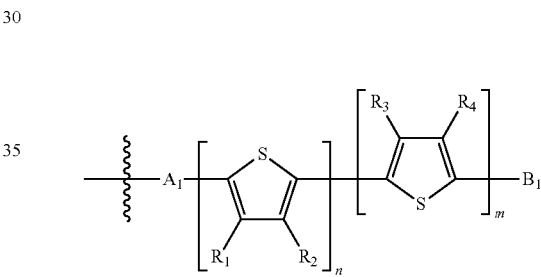

where n is an integer between 0 and 5, inclusive and m is an integer between 0 and 5, inclusive, and $1 \le m+n \le 5$. Each $B_1$ is independently selected from a an aryl or heteroaryl groups: optionally substituted with lone two, or more $B_2$. Each $B_2$ is independently selected from a substituent or n

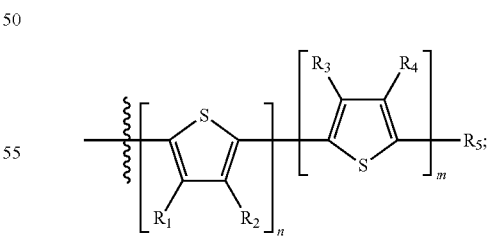

where $R_1$, $R_2$, $R_3$, $R_4$ and $R_5$ are each independently H or a substituent.

In some compounds according to Formula III, $A_1$ is a DONOR, defined below.

In some compounds according to Formula III, $H_3$ is -$A_1$-$B_2$, or

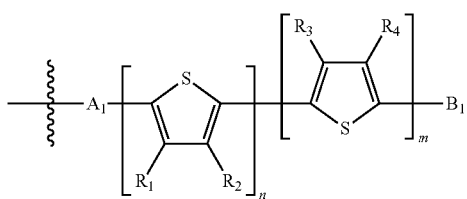

where n is an integer between 0 and 5, inclusive and m is an integer between 0 and 5, inclusive, and $1 \leq m+n \leq 5$ and $A_1$ is a DONOR, defined below. Each $B_1$ is independently selected from a an aryl or heteroaryl groups optionally substituted with one, two, or more $B_2$. Each $B_2$ is independently selected from H, a substituent or

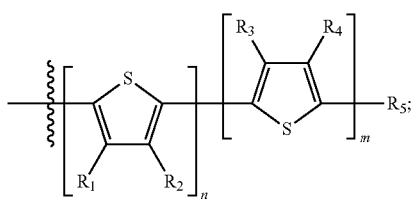

where $R_1$, $R_2$, $R_3$, $R_4$ and $R_5$ are each independently H or a substituent.

In some compounds according to Formula III, $B_2$ is H or a substituent.

In some compounds according to Formula III, $B_2$ is

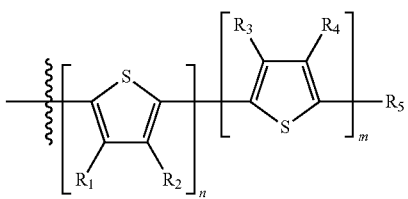

where $R_1$, $R_2$, $R_3$, $R_4$ and $R_5$ are each independently H or a substituent.

In some compounds according to Formula III, —$B_1$ is

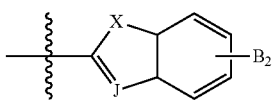

where J is selected from CH and N, and X is S, O, or NH when X is CH; and X is S when J is N.

In some compounds according to Formula III, —$B_1$ is $R_6$ is selected from aryl, perfluoroaryl, or $C_6$-$C_{30}$ aryl optionally perfluorinated.

Some compounds according to Formula III have Formulas 6, 7, or 8

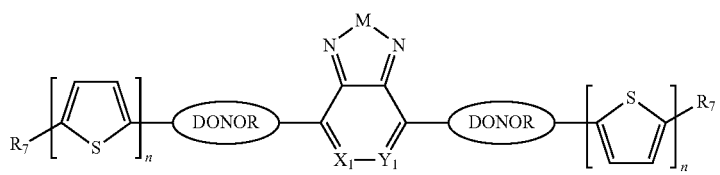

6

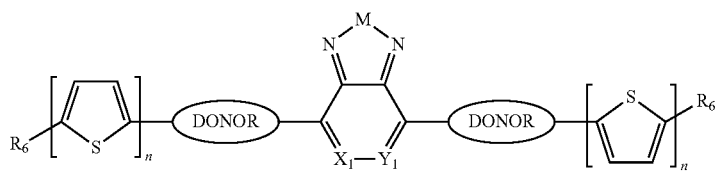

7

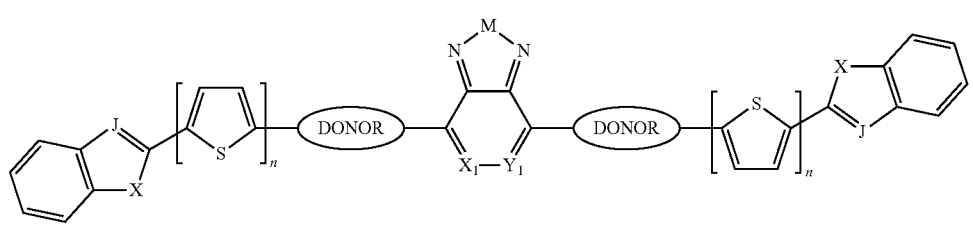

8 where n is an integer from 0 to 5 inclusive; m is an integer from 0 to 5 inclusive, where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N-R$_1$)—; where R$_6$ is H or a substituent; R$_7$ is H or a substituent; and R$_8$ is H or a substituent. X$_1$ is H or halogen and Y$_1$ is H or halogen, where at least one of X$_j$ and Y$_1$ is halogen. R$_7$ is selected from H or a substituent. J is selected from CH and N. X is S, O, or NH when X is CH; and X is S when J is N. R$_6$ is selected from aryl, perfluoroaryl, or C$_6$-C$_{30}$ aryl optionally perfluorinated or optionally substituted with one or more C$_1$-C$_{16}$ alkyl groups.

In some compounds according to Formula B, H$_2$ is

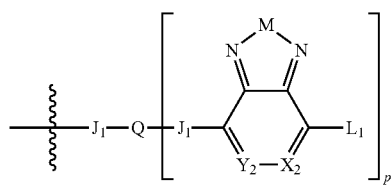

where p is 1, and H$_1$ and L$_1$ are the same.

In some compounds according to Formula B, H$_1$ is

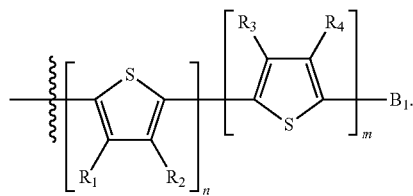

In some compounds according to formula B, B$_1$ is substituted by one B$_2$.

In some compounds according to formula B, each J$_1$ is a nonentity.

In some compounds according to formula B, H$_2$ is

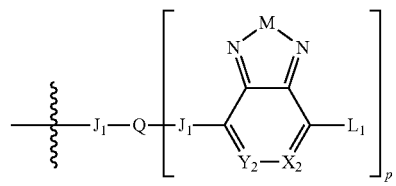

where p is 1, both J$_1$ are both nonentities, and L$_1$ and H$_1$ are the same and are both

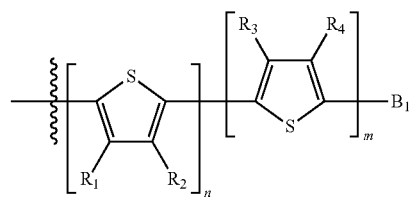

where B$_1$ is substituted by one B$_2$.

Some compounds according to formula B have Formula II, shown below:

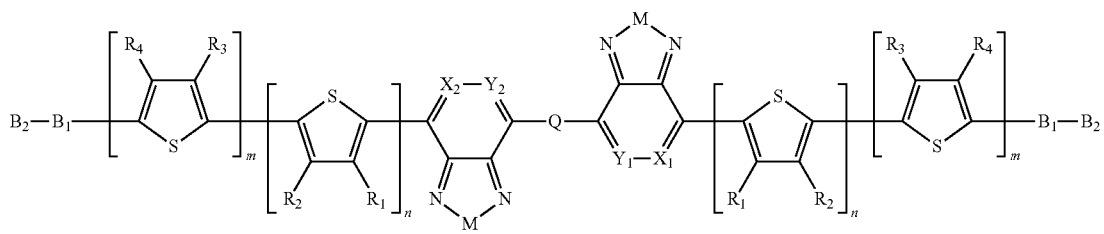

where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N—R$_1$)—; where R$_6$ is H or a substitutent; R$_7$ is H or a substituent; and R$_8$ is H or a substituent. X$_1$ is N or C—R$_9$, Y$_1$ is N or C—R$_9$, and one of X$_1$ and Y$_1$ is N, and the other is C—R$_9$; where R$_9$ is F, Cl, Br, or I. X$_2$ is N or C—R$_9$, Y$_2$ is N or C—R$_9$, and one of X$_2$ and Y$_2$ is N, and the other is C—R$_9$; where R$_9$ is F, Cl, Br, or I. Q is a bivalent aryl or heteroaryl group. Each B$_1$ is independently selected from a an aryl or heteroaryl groups. Each B$_2$ is independently selected from H or a substituent; where R$_1$, R$_2$, R$_3$, and R$_4$ are each independently H or a substituent.

In some compounds according to Formula II, B$_1$ is a substituted or unsubstituted thiophene.

In some compounds according to Formula II, Q may be thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b: 3,4-b']-dithiophene, where R and R'=$C_1$-$C_{30}$ alkyl or $C_6$-$C_{30}$ aryl.

In some compounds according to formula II, $B_1$ may be, independently, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole.

In some compounds according to Formula II, Q is 3,3'-RR'silylene-2,2'-bithiophene and R and R' are both $C_1$-$C_{30}$ alkyl.

In some compounds according to Formula II, Q is

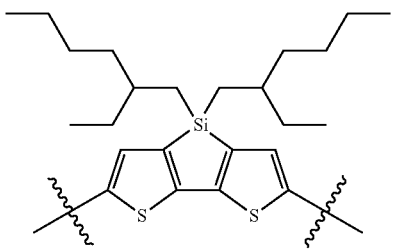

In some compounds according to Formula II, n±m=1.

In some compounds according to Formula II, $B_2$ is alkyl.

In some compounds according to Formula II, Q is 3,3'-RR'silylene-2,2'-bithiophene and R and R' are both $C_1$-$C_{30}$ alkyl, $B_1$ is thiophene, n+m=1, and $B_2$ is alkyl.

For example, the compound according to Formula II may have the structure

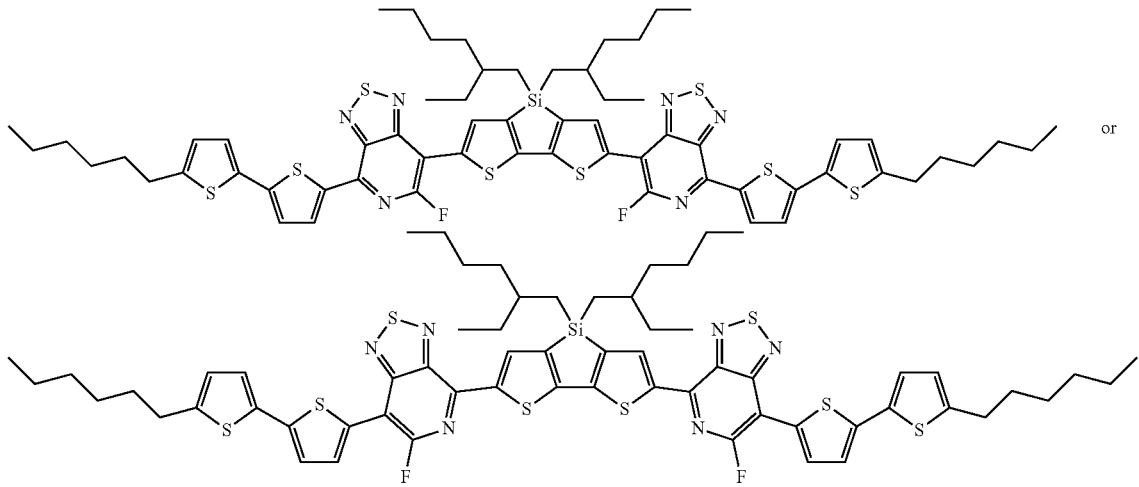

or

In some compounds according to Formula II, M is S. In some compounds according to Formula II, all $R_9$ are F.

In some compounds according to Formula B, $H_2$ is

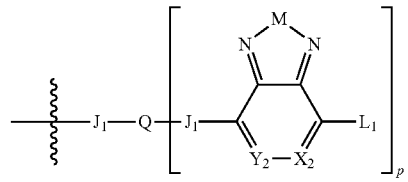

where p is 1, both $J_1$ are both nonentities, and $L_1$ and $H_1$ are the same and are both —$B_2$ or -$A_1$-$B_2$.

Some compounds according to Formula B have Formula I:

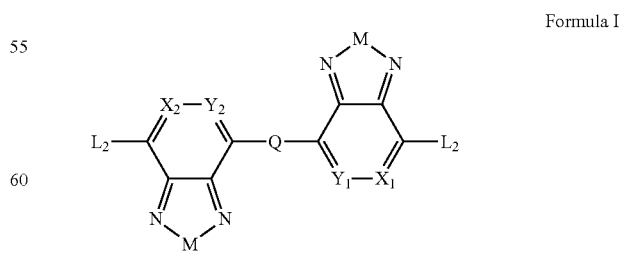

Formula I where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—R$_1$)—; where R$_6$ is H or a substitutent; R$_7$ is H or a substituent; and R$_8$ is H or a substituent. X$_1$ is N or C—R$_9$, Y$_1$ is N or C—R$_9$, one of X$_1$ and Y$_1$ is N, and the other is C—R$_9$; where R$_9$ is F, Cl, Br, or I. X$_2$ is N or C—R$_9$, Y$_2$ is N or C—R$_9$, one of X$_2$ and Y$_2$ is N, and the other is C—R$_9$; where R$_9$ is F, Cl, Br, or I. Q is a bivalent aryl or heteroaryl group.

Each L$_2$ is independently —B$_2$ or -A$_1$-B$_2$. Each A$_1$ is independently selected from substituted or unsubstituted aryl group, substituted or unsubstituted heteroaryl group,

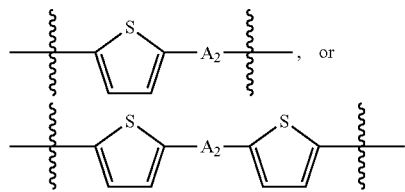, or where A$_2$ is independently a substituted or unsubstituted aryl group or substituted or unsubstituted heteroaryl group;

Each B$_2$ is independently selected from H, a substituent, halogen, —Sn(C$_1$-C$_4$ alkyl)$_4$, —Zn(halide), —Mg(halide), —B(OH)$_2$, or boronate ester, or

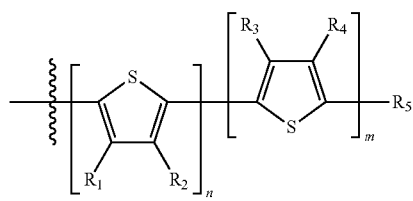

where n is an integer between 0 and 5, inclusive and m is an integer between 0 and 5, inclusive, and 1≤m+n≤5; and where R$_1$, R$_2$, R$_3$, and R$_4$ are each independently H or a substituent, R$_5$ is H, a substituent, halogen, —Sn(C$_1$-C$_4$ alkyl)$_3$, —Zn(halide), —Mg(halide), —B(OH)$_2$, or boronate ester.

In some compounds according to Formula I, Q may be substituted or unsubstituted thiophene, pyrrole, furan, phenyl, phosphole, benzodithiophene, spirofluorene, spirothiophene, bithiophene terthiophene, thienothiophene, dithienothiophene benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2, 2'-bithiophene, 3,3'RR'-cyclopenta[2,1-b:3,4-b']-dithiophene where R and R'=C$_1$-C$_{30}$ alkyl or C$_6$-C$_{30}$ aryl.

In some compounds according to Formula I, each L$_2$ is -A$_1$-B$_2$.

In some compounds according to Formula I, and A$_1$ is independently substituted or unsubstituted thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole.

In some compounds according to Formula I each L$_2$ is B$_2$.

In some compounds according to Formula I B$_2$ is

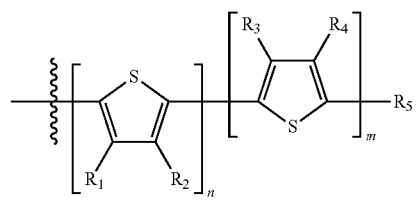

where n is an integer between 0 and 5, inclusive and m is an integer between 0 and 5, inclusive, and 1≤m+n≤5; and where R$_1$, R$_2$, R$_3$, R$_4$ and R$_5$ are each independently H or a substituent.

In some compounds according to Formula B, H$_2$ is

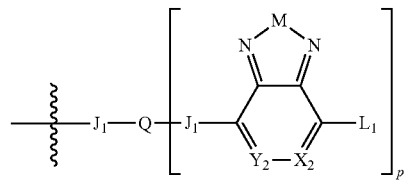

where p is 2.

In some compounds according to formula B, H$_2$ is

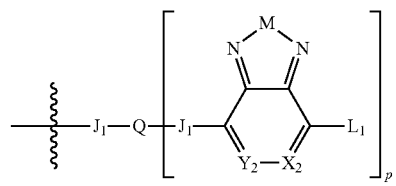

where p is 2, and H$_1$ and each L$_1$ are the same.

In some compounds according to formula B, H$_2$ is

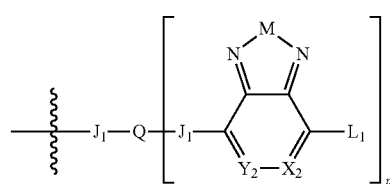

where p is 2, and H$_1$ and each L$_1$ are the same and are —B$_2$ or -A$_1$-B$_2$.

Some compounds according to Formula B have Formula IV-V:

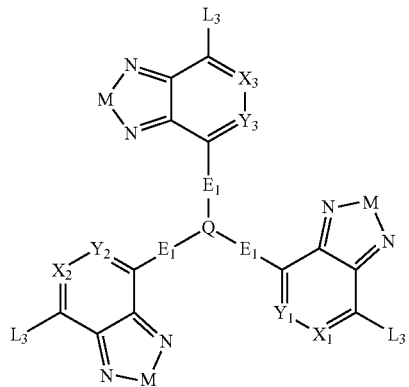

Formula IV-V where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N-$R_1$)—; where $R_6$ is H or a substituent; $R_7$ is H or a substituent; and $R_8$ is H or a substituent. $X_1$ is N or C—$R_9$, $Y_1$ is N or C—$R_9$, one of $X_1$ and $Y_1$ is N, and the other is C—$R_9$; where $R_9$ is F, Cl, Br, or I. $X_2$ is N or C—$R_9$, $Y_2$ is N or C—$R_9$, one of $X_2$ and $Y_2$ is N, and the other is C—$R_9$; where $R_9$ is F, Cl, Br, or I. $X_3$ is N or C—$R_9$, $Y_3$ is N or C—$R_9$, one of $X_3$ and $Y_3$ is N, and the other is C—$R_9$; where $R_9$ is F, Cl, Br, or I. Q is a trivalent aryl or heteroaryl group.

Each $E_1$ is independently either nonentity, substituted or unsubstituted aryl, substituted or unsubstituted heteroaryl groups, or

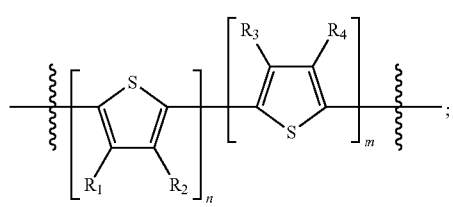

Each $L_3$ is, independently, —$B_2$ or -$A_1$-$B_2$.

Each $A_1$ is independently selected from substituted or unsubstituted aryl group, substituted or unsubstituted heteroaryl group,

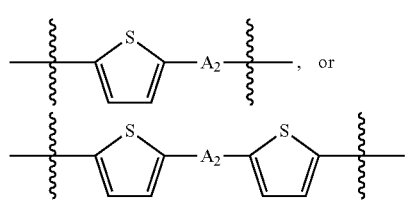

where $A_2$ is independently a substituted or unsubstituted aryl group or substituted or unsubstituted heteroaryl group.

Each $B_2$ is independently selected from H, a substituent, halogen, —Sn($C_1$-$C_4$ alkyl)$_4$, —Zn(halide), —Mg(halide), —B(OH)$_2$, or boronate ester, or

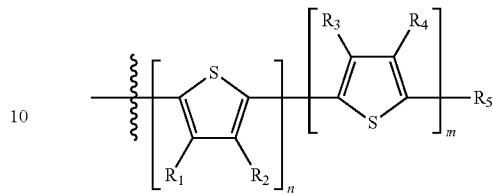

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_5$ is H, a substituent, halogen, —Sn($C_1$-$C_4$ alkyl)$_3$, —Zn (halide), —Mg(halide), —B(OH)$_2$, or boronate ester.

In some compounds according to Formula IV-V, $E_1$ is a nonentity.

Some compounds according to Formula IV-V have formula IVa

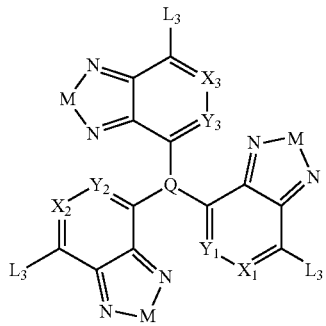

Formula IVa where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N-$R_1$)—; where $R_6$ is H or a substituent; $R_7$ is H or a substituent; and $R_8$ is H or a substituent. $X_1$ is N or C—$R_9$, $Y_1$ is N or C—$R_9$, one of $X_1$ and $Y_1$ is N, and the other is C—$R_9$; where $R_9$ is F, Cl, Br, or I. $X_2$ is N or C—$R_9$, $Y_2$ is N or C—$R_9$, one of $X_2$ and $Y_2$ is N, and the other is C—$R_9$; where $R_9$ is F, Cl, Br, or I. $X_3$ is N or C—$R_9$, $Y_3$ is N or C—$R_9$, one of $X_3$ and $Y_3$ is N, and the other is C—$R_9$; where $R_9$ is F, Cl, Br, or I. Q is a trivalent aryl or heteroaryl group.

Each $L_3$ is, independently, —$B_2$ or -$A_1$-$B_2$.

Each $A_1$ is independently selected from substituted or unsubstituted aryl group, substituted or unsubstituted heteroaryl group,

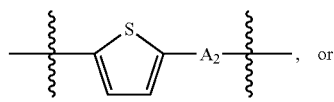

-continued

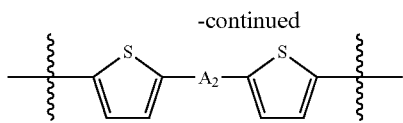

where $A_2$ is independently a substituted or unsubstituted aryl group or substituted or unsubstituted heteroaryl group.

Each $B_2$ is independently selected from H, a substituent, halogen, —Sn($C_1$-$C_4$ alkyl)$_4$, —Zn(halide), —Mg(halide), —B(OH)$_2$, or boronate ester, or

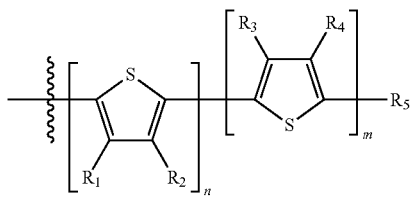

where n is an integer between 0 and 5, inclusive and m is an integer between 0 and 5, inclusive, and $1 \leq m+n \leq 5$; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

In some compounds according to Formula IV-V, each $E_1$ is independently, a substituted or unsubstituted aryl, a substituted or unsubstituted heteroaryl group, or

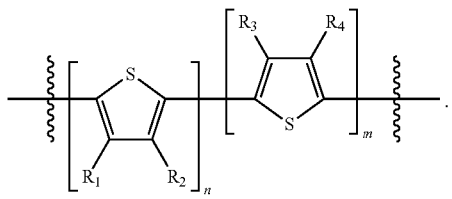

Some compounds according to Formula IV-V have Formula Va:

Formula Va

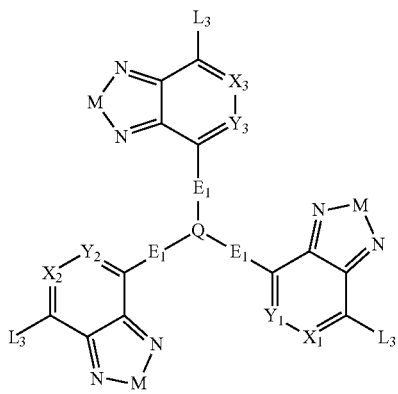

where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—; where $R_6$ is H or a substitutent; $R_7$ is H or a substituent; and $R_8$ is H or a substituent. $X_1$ is N or C—$R_9$, $Y_1$ is N or C—$R_9$, one of $X_1$ and $Y_1$ is N, and the other is C—$R_9$; where $R_9$ is F, Cl, Br, or I. $X_2$ is N or C—$R_9$, $Y_2$ is N or C—$R_9$, one of $X_2$ and $Y_2$ is N, and the other is C—$R_9$; where $R_9$ is F, Cl, Br, or I. $X_3$ is N or C—$R_9$, $Y_3$ is N or C—$R_9$, one of $X_3$ and $Y_3$ is N, and the other is C—$R_9$; where $R_9$ is F, Cl, Br, or I. Q is a trivalent aryl or heteroaryl group.

Each $E_1$ is independently a substituted or unsubstituted aryl, a substituted or unsubstituted heteroaryl groups, or

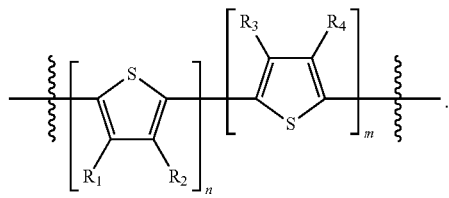

Each $L_3$ is, independently, —$B_2$ or -$A_1$-$B_2$.

Each $A_1$ is independently selected from substituted or unsubstituted aryl group, substituted or unsubstituted heteroaryl group,

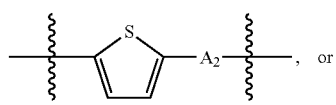, or

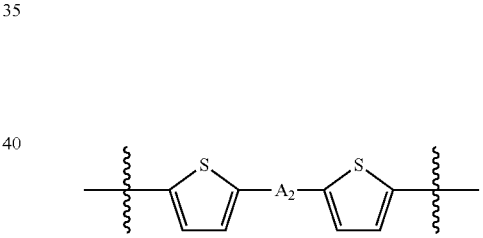

where $A_2$ is independently a substituted or unsubstituted aryl group or substituted or unsubstituted heteroaryl group.

Each $B_2$ is independently selected from H, a substituent, halogen, —Sn($C_1$-$C_4$ alkyl)$_4$, —Zn(halide), —Mg(halide), —B(OH)$_2$, or boronate ester, or

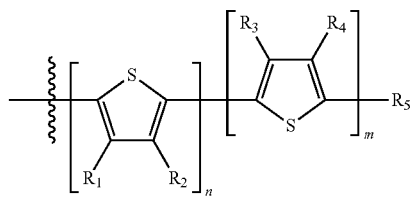

where n is an integer between 0 and 5, inclusive and m is an integer between 0 and 5, inclusive, and $1 \leq m+n \leq 5$; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

In some compounds according to Formula B, H₂ is

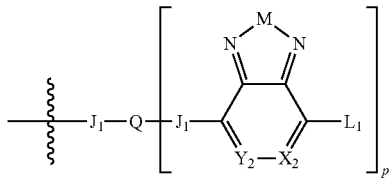

where p is 3.

In some compounds according to formula B, H₂ is

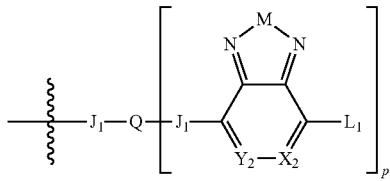

where p is 3, and H₁ and each L₁ are the same.

In some compounds according to formula B, H₂ is

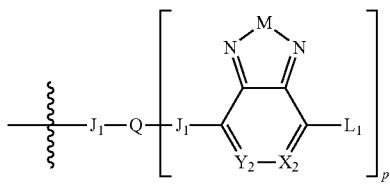

where p is 3, and H₁ and each L₁ are the same and are —B₂ or -A₁-B₂.

Some compounds according to Formula B have Formula VI-VII:

VI-VII

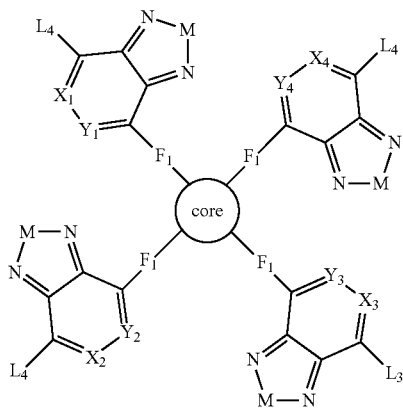

where the moiety

is a tetravalent aryl or heteroaryl group selected from

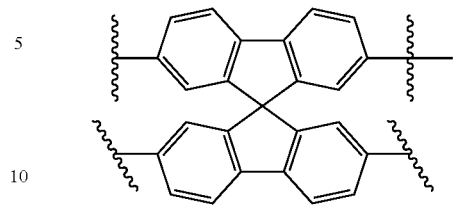

(2,2',7,7'-yl-9,9'-spirobi[fluorene]),

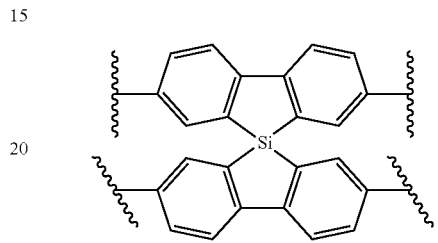

(3,3',7,7'-yl-5,5'-spirobi[dibenzo[b,d]silole]),

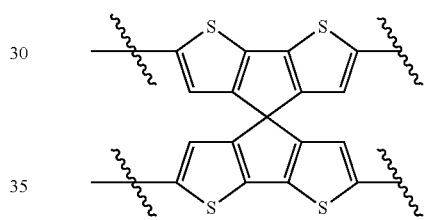

(2,2',6,6'-yl-4,4"-spirobi[cyclopenta[1,2-b:5,4-b']dithiophene]), or

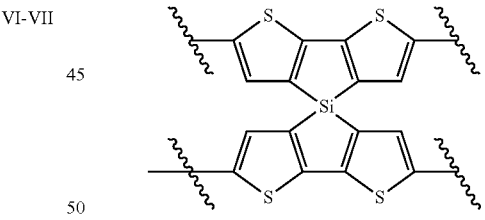

(2,2',6,6'-yl-4,4'-spirobi[silolo[3,2-b:4,5-b']dithiophene]);
where M is selected from sulfur (S), oxygen (O), selenium (Se), tellurium (Te), —N(R₆)—, —C(R₇)₂—C(R₈)₂—, —CR₇=CR₈—, —S(=O)₂—, —S(=O)—, —C(=O)—, —C(=S)—, or —C(=N—R₁)—; where R₆ is H or a substitutent; R₇ is H or a substituent; and R₈ is H or a substituent. X₁ is N or C—R₉, Y₁ is N or C—R₉, one of X₁ and Y₁ is N, and the other is C—R₉; where R₉ is F, Cl, Br, or I. X₂ is N or C—R₉, Y₂ is N or C—R₉, one of X₂ and Y₂ is N, and the other is C—R₉; where R₉ is F, Cl, Br, or I. X₃ is N or C—R₉, Y₃ is N or C—R₉, one of X₃ and Y₃ is N, and the other is C—R₉; where R₉ is F, Cl, Br, or I. X₄ is N or C—R₉, Y₄ is N or C—R₉, one of X₄ and Y₄ is N, and the other is C—R₉; where R₉ is F, Cl, Br, or I.

Each $F_1$ is independently either nonentity, substituted or unsubstituted aryl, substituted or unsubstituted heteroaryl groups, or

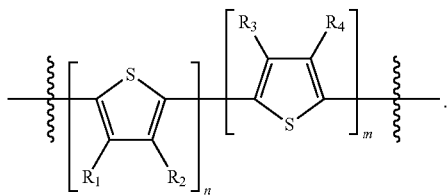

Each $L_4$ is, independently, —$B_2$ or -$A_1$-$B_2$.

Each $A_1$ is independently selected from substituted or unsubstituted aryl group, substituted or unsubstituted heteroaryl group,

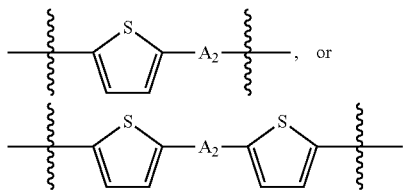

where $A_2$ is independently a substituted or unsubstituted aryl group or substituted or unsubstituted heteroaryl group.

Each $B_2$ is independently selected from H, a substituent, halogen, —$Sn(C_1\text{-}C_4 \text{ alkyl})_4$, —Zn(halide), —Mg(halide), —$B(OH)_2$, or boronate ester, or

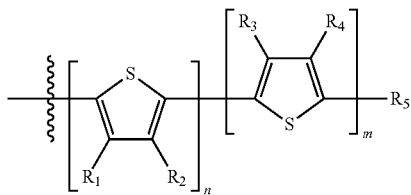

where n is an integer between 0 and 5, inclusive and m is an integer between 0 and 5, inclusive, and $1 \leq m+n \leq 5$; and where $R_1$, $R_2$, $R_3$, and $R_4$ are each independently H or a substituent, $R_5$ is H, a substituent, halogen, —$Sn(C_1\text{-}C_4 \text{ alkyl})_3$, —Zn (halide), —Mg(halide), —$B(OH)_2$, or boronate ester.

Some compounds according to Formula VI-VII have Formula VIa:

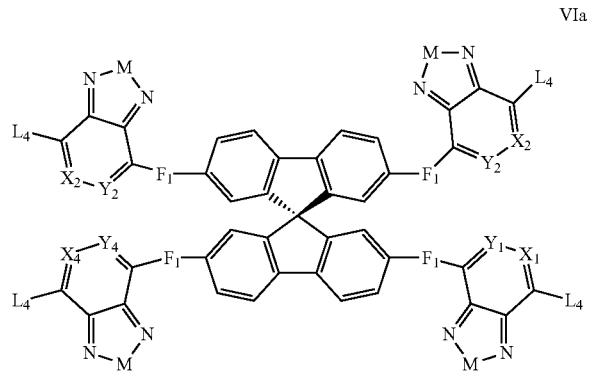

VIa where M is selected from sulfur (S), oxygen (O), selenium (Se), tellurium (Te), —$N(R_6)$—, —$C(R_7)_2$—$C(R_8)_2$—, —$CR_7$=$CR_8$—, —$S(=O)_2$—, —$S(=O)$—, —$C(=O)$—, —$C(=S)$—, or —$C(=N-R_1)$—; where $R_6$ is —H or a substitutent $R_7$ is H or a substituent and $R_8$ is H or a substituent. $X_1$ is N or C—$R_9$, $Y_1$ is N or C—$R_9$, one of $X_1$ and $Y_1$ is N, and the other is C—$R_9$; where $R_9$ is F, Cl, Br, or I. $X_2$ is N or C—$R_9$, $Y_2$ is N or C—$R_9$, one of $X_2$ and $Y_2$ is N, and the other is C—$R_9$; where $R_9$ is F, Cl, Br, or I. $X_3$ is N or C—$R_9$, $Y_3$ is N or C—$R_9$, one of $X_3$ and $Y_3$ is N, and the other is C—$R_9$; where $R_9$ is F, Cl, Br, or I. $X_4$ is N or C—$R_9$, $Y_4$ is N or C—$R_9$, one of $X_4$ and $Y_4$ is N, and the other is C—$R_9$; where $R_9$ is F, Cl, Br, or I.

Each $F_1$ is independently either nonentity, substituted or unsubstituted aryl, substituted or unsubstituted heteroaryl groups, or

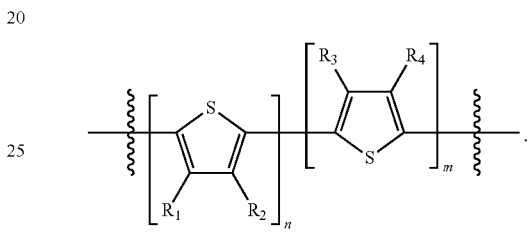

Each $L_4$ is, independently, —$B_2$ or -$A_1$-$B_2$

Each $A_1$ is independently selected from substituted or unsubstituted aryl group, substituted or unsubstituted heteroaryl group,

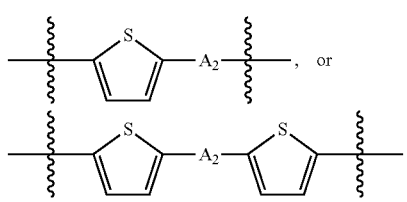

where $A_2$ is independently a substituted or unsubstituted aryl group or substituted or unsubstituted heteroaryl group.

Each $B_2$ is independently selected from H, a substituent, halogen, —$Sn(C_1\text{-}C_4 \text{ alkyl})_4$, —Zn(halide), —Mg(halide), —$B(OH)_2$, or boronate ester, or

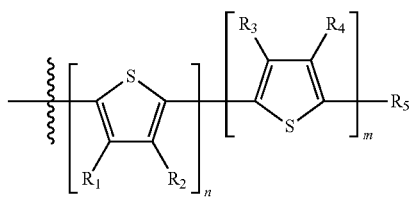

where n is an integer between 0 and 5, inclusive and m is an integer between 0 and 5, inclusive, and $1 \leq m+n \leq 5$; and where $R_1$, $R_2$, $R_3$, and $R_4$ are each independently H or a substituent, $R_5$ is H, a substituent, halogen, —$Sn(C_1\text{-}C_4 \text{ alkyl})_3$, —Zn (halide), —Mg(halide), —$B(OH)_2$, or boronate ester.

Some compounds according to Formula VI-VII have Formula VIIa:

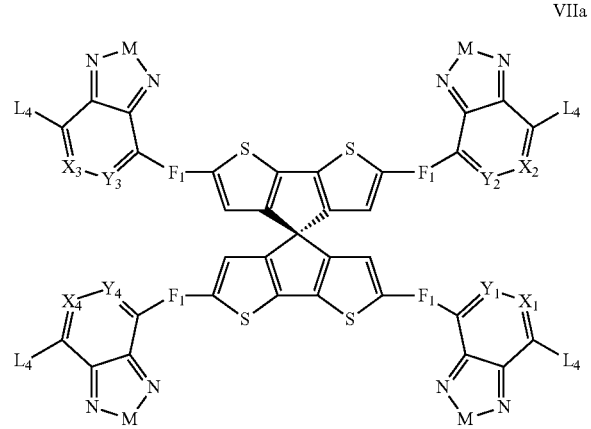

where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N–R$_1$)—; where R$_6$ is H or a substitutent; R$_7$ is H or a substituent; and R$_8$ is H or a substituent. X$_1$ is N or C—R$_9$, Y$_1$ is N or C—R$_9$, one of X$_1$ and Y$_1$ is N, and the other is C—R$_9$; where R$_9$ is F, Cl, Br, or I. X$_2$ is N or C—R$_9$, Y$_2$ is N or C—R$_9$, one of X$_2$ and Y$_2$ is N, and the other is C—R$_9$; where R$_9$ is F, Cl, Br, or I. X$_3$ is N or C—R$_9$, Y$_3$ is N or C—R$_9$, one of X$_3$ and Y$_3$ is N, and the other is C—R$_9$; where R$_9$ is F, Cl, Br, or I. X$_4$ is N or C—R$_9$, Y$_4$ is N or C—R$_9$, one of X$_4$ and Y$_4$ is N, and the other is C—R$_9$; where R$_9$ is F, Cl, Br, or I.

Each F$_1$ is independently either nonentity, substituted or unsubstituted aryl, substituted or unsubstituted heteroaryl groups, or

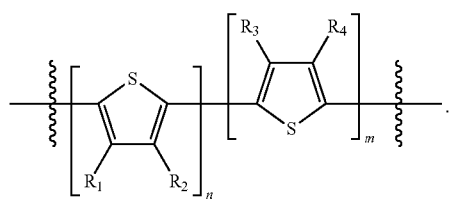

Each L$_4$ is, independently, —B$_2$ or -A$_1$-B$_2$.

Each A$_1$ is independently selected from substituted or unsubstituted aryl group, substituted or unsubstituted heteroaryl group,

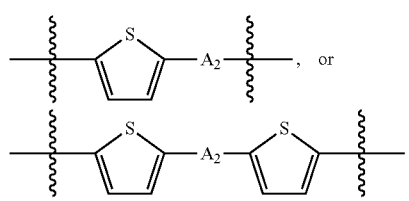

where A$_2$ is independently a substituted or unsubstituted aryl group or substituted or unsubstituted heteroaryl group.

Each B$_2$ s independently selected from H a substituent, halogen, —Sn(C$_1$-C$_4$ alkyl)$_4$, —Zn(halide), —Mg(halide), —B(OH)$_2$, or boronate ester, or

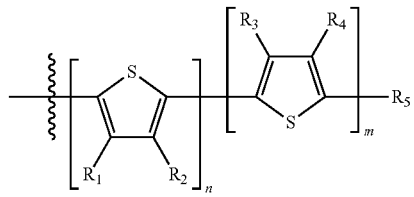

where n is an integer between 0 and 5, inclusive and m is an integer between 0 and 5, inclusive, and 1≤m+n≤5; and where R$_1$, R$_2$, R$_3$, and R$_4$ are each independently H or a substituent, R$_5$ is H, a substituent, halogen, —Sn(C$_1$-C$_4$ alkyl)$_3$, —Zn (halide), —Mg(halide), —B(OH)$_2$, or boronate ester.

In some compounds according to Formula B, Q is a DONOR.

In some compounds according to Formula B, H$_2$ is

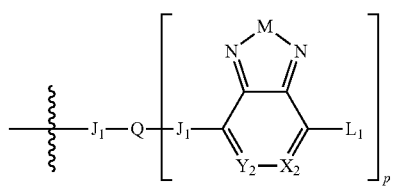

where p is 1, and H$_1$ and L$_1$ are the same, and both H$_1$ and L$_1$ are —B$_2$, where B$_2$ is independently selected from, H, a substituent or

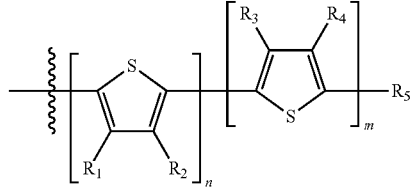

where n is an integer between 0 and 5, inclusive and m is an integer between 0 and 5, inclusive, and 1≤m+n≤5. And where R$_1$, R$_2$, R$_3$, R$_4$ and R$_5$ are each independently H or a substituent.

In some compounds of formula B, Q is a DONOR, H$_2$ is

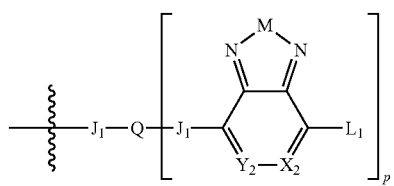

where p is 1, each J$_1$ is a nonentity, and H$_1$ and L$_1$ are the same, and both H$_1$ and L$_1$ are —B$_2$, where B$_2$ is independently selected from, H, a substituent or

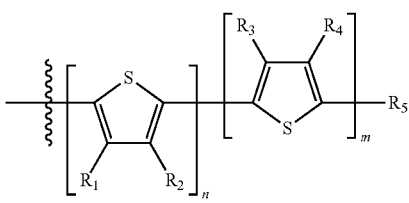

where n is an integer between 0 and 5, inclusive and m is an integer between 0 and 5, inclusive, and $1 \leq m+n \leq 5$. And where $R_1$, $R_2$, $R_3$, $R_4$ and $R_5$ are each independently H or a substituent.

Some compounds of Formula B have Formula 1:

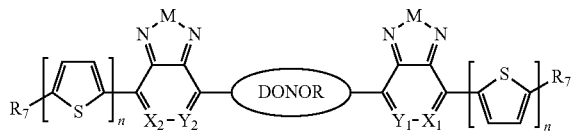

where n is an integer from 0 to 5 inclusive, where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N-R$_1$)—; where $R_6$ is H or a substitutent; $R_7$ is H or a substituent; and $R_8$ is H or a substituent. $X_1$ is N or C—$R_9$, $Y_1$ is N or C—$R_9$, one of $X_1$ and $Y_1$ is N, and the other is C—$R_9$; where $R_9$ is F, Cl, Br, or I. $X_2$ is N or C—$R_9$, $Y_2$ is N or C—$R_9$, one of $X_2$ and $Y_2$ is N, and the other is C—$R_9$; where $R_9$ is F, Cl, Br, or I.

In some compounds of formula B, $H_2$ is

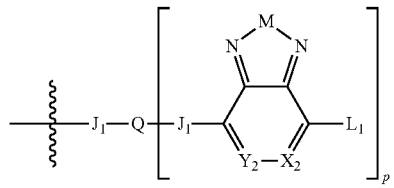

where p is 1, $H_1$ and $L_1$ are the same, and both $H_1$ and $L_1$ are

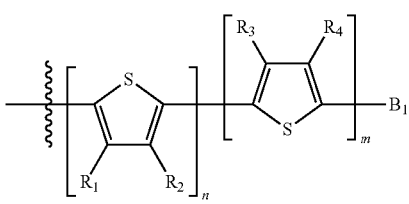

where n is an integer between 0 and 5, inclusive and m is an integer between 0 and 5, inclusive, and $1 \leq m+n \leq 5$ where each $B_1$ is independently selected from an aryl or heteroaryl groups substituted with one, two, or more $B_2$. Each $B_2$ is independently selected from H, a substituent or

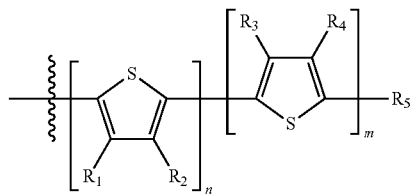

where $R_1$, $R_2$, $R_3$, $R_4$ and $R_8$ are each independently H or a substituent.

In some compounds of formula B, H and $L_1$ may be

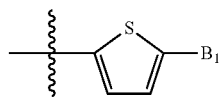

In some compounds of formula B, $B_1$ is substituted by two $B_2$.

In some compounds of formula B, $H_2$ is

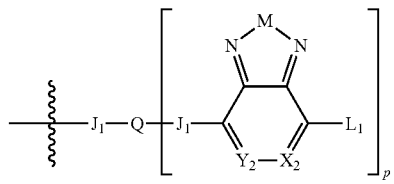

where p is 1, each $J_1$ is a nonentity, $H_1$ and $L_1$ are the same, and both $H_1$ and $L_1$ are

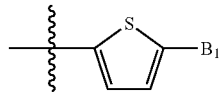

and each $B_1$ is an aryl or heteroaryl group substituted with two $B_2$, where each $B_2$ is independently selected from H, a substituent or

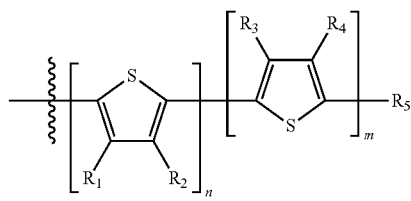

where n is an integer between 0 and 5, inclusive and m is an integer between 0 and 5 and where $R_1$, $R_2$, $R_3$ and $R_5$ are each independently H or a substituent.

Some compounds of formula B have formula 2:

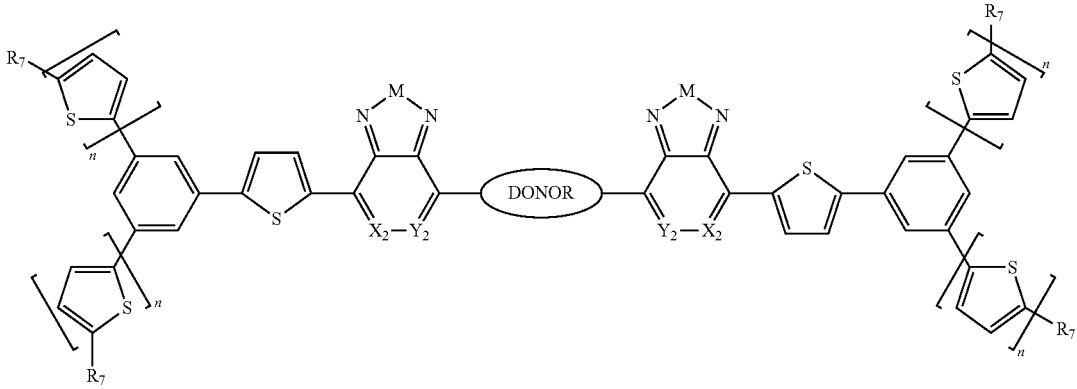

where n is an integer from 0 to 5 inclusive, where M is selected from sulfur (S), oxygen (O), selenium (Se), tellurium (Te), —N($R_6$)—, —C($R_7$)$_2$—C($R_8$)$_2$—, —$CR_7$=$CR_8$—, —S(=O)$_2$—, —S(=O)—, —C(=O)—, —C(=S)—, or —C(=N—$R_1$)—; where $R_6$ is H or a substitutent; $R_7$ is H or a substituent; and $R_8$ is H or a substituent. $X_1$ is H or halogen and $Y_1$ is H or halogen, where at least one of $X_1$ and $Y_1$ is halogen. $X_2$ is H or halogen and each $Y_2$ is H or halogen, where at least one of $X_2$ and $Y_2$ is halogen. $R_7$ is selected from H or a substituent.

In some compounds of formula B, $H_2$ is

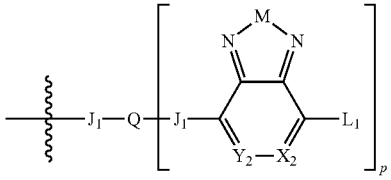

where p is 1, $H_1$ and $L_1$ are the same, and both $H_1$ and $L_1$ are -$A_1$-$B_2$ or

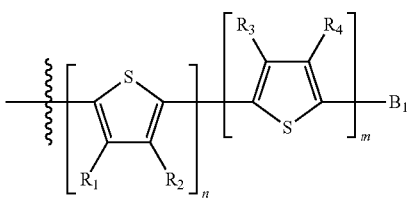

where n is an integer between 0 and 5, inclusive and m is an integer between 0 and 5, inclusive, and 1≤m+n≤5 where each $B_1$ is independently selected from an aryl or heteroaryl groups substituted with one, two, or more $B_2$. Each $B_2$ is independently selected from H, a substituent, halogen, —Sn($C_1$-$C_4$ alkyl)$_4$, —Zn(halide), —Mg(halide), —B(OH)$_2$, or boronate ester, or

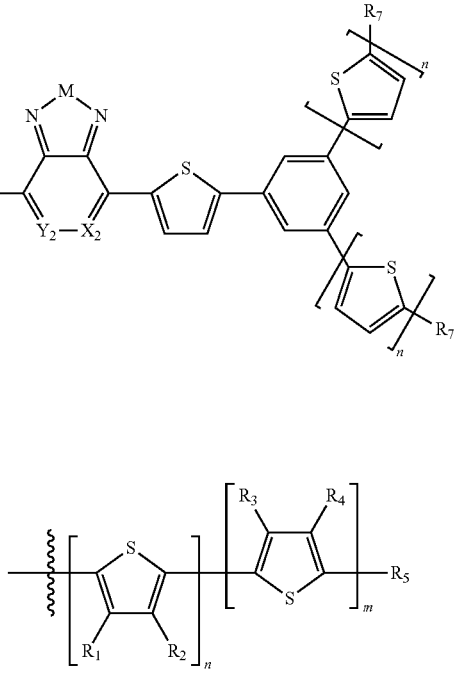

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_5$ is H, a substituent, halogen, —Sn($C_1$-$C_4$ alkyl)$_3$, —Zn (halide), —Mg(halide), —B(OH)$_2$, or boronate ester.

In some compounds of formula B, $B_2$ is H or a substituent.

In some compounds of formula B, $H_2$ is

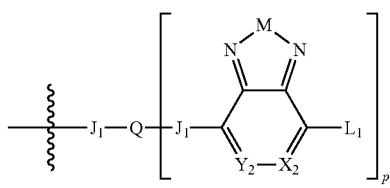

where p is 1, $H_1$ and $L_1$ are the same, and both $H_1$ and $L_1$ are -$A_1$-$B_2$ or

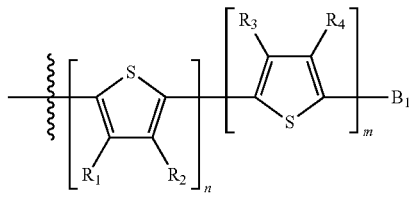

where n is an integer between 0 and 5, inclusive and m is an integer between 0 and 5, inclusive, and 1≤m+n≤5 where each $B_1$ is independently selected from an aryl or heteroaryl groups substituted with one, two, or more $B_2$. Each $B_2$ is independently selected from H or a substituent.

In some compounds of formula B, $-A_1-B_2$ is

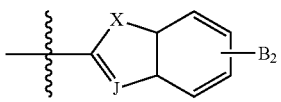

where J is selected from CH and N, and X is S, O, or NH when X is CH; and X is S when J is N.

In some compounds of formula B, $-B_1$ is

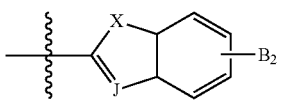

where J is selected from CH and N, and X is S, O, or NH when X is CH; and X is S when J is N.

Some compounds of formula B have formula 3:

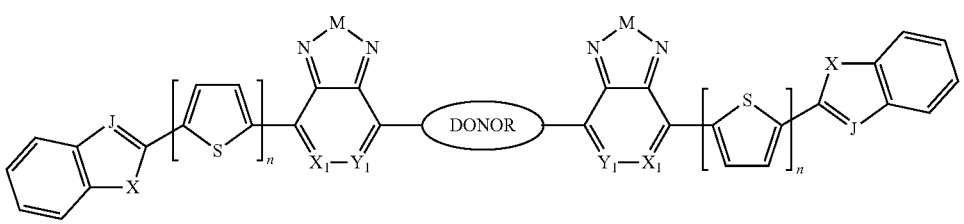

where n is an integer from 0 to 5 inclusive, J is selected from CH and N and X is S, O, or NH when X is CH; and X is S when J is N. M is selected from sulfur (S), oxygen (O), selenium (Se), tellurium (Te), $-N(R_6)-$, $-C(R_7)_2-C(R_8)_2-$, $-CR_7=CR_8-$, $-S(=O)_2-$, $-S(=O)-$, $-C(=O)-$, $-C(=S)-$, or $-C(=N-R_1)-$; where $R_6$ is H or a substituent; $R_7$ is H or a substituent; and $R_8$ is H or a substituent. $X_1$ is H or halogen and $Y_1$ is H or halogen, where at least one of $X_1$ and $Y_1$ is halogen. $X_2$ is H or halogen and each $Y_2$ is H or halogen, where at least one of $X_2$ and $Y_2$ is halogen.

In some compounds of formula B, $B_1$ is substituted by one $B_2$.

In some compounds of formula B, $B_2$ is diarylamine.

In some compounds of formula B, $B_1$ is phenyl.

In some compounds of formula B, $A_1$ is phenyl

In some compounds of formula B, $H_2$ is

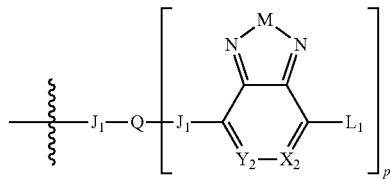

where p is 1, each $J_1$ is a nonentity, $H_1$ and $L_1$ are the same, and both $H_1$ and $L_1$ are $-A_1-B_2$ where $A_1$ is phenyl or

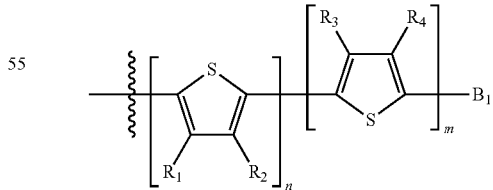

where n is an integer between 0 and 5, inclusive and m is an integer between 0 and 5, inclusive, and $1 \leq m+n \leq 5$ where each $B_1$ is phenyl substituted with one $B_2$, Each $B_2$ is independently selected from H or diarylamine.

Some compounds of formula B have formula 4:

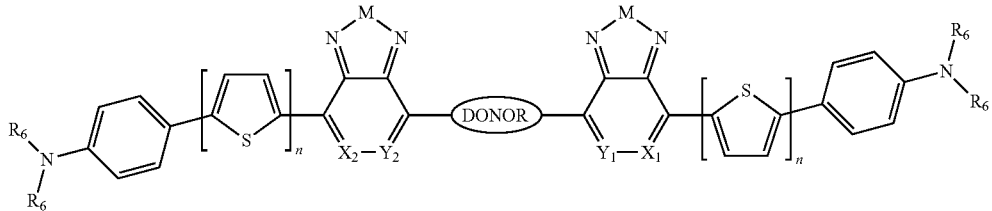

where n is an integer from 0 to 5 inclusive, J is selected from CH and N and X is S, O, or NH when X is CH; and X is S when J is N, where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N-$R_1$)—; where $R_6$ is H or a substitutent; $R_7$ is H or a substituent; and $R_8$ is H or a substituent. $X_1$ is H or halogen and $Y_1$ is H or halogen, where at least one of $X_1$ and $Y_1$ is halogen. $X_2$ is H or halogen and each $Y_2$ is H or halogen, where at least one of $X_2$ and $Y_2$ is halogen. $R_8$ is $C_6$-$C_{30}$ aryl optionally substituted with one or more $C_1$-$C_{16}$ allyl groups.

In some compounds of formula B, $H_2$ is

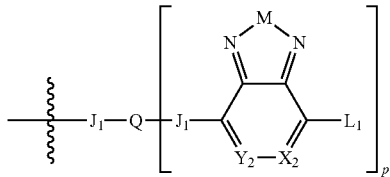

where p is 1, $H_1$ and $L_1$ are the same, and both $H_1$ and $L_1$ are both -$A_1$-$B_1$ where each $A_1$ is independently selected from substituted or unsubstituted aryl group, substituted or unsubstituted heteroaryl group,

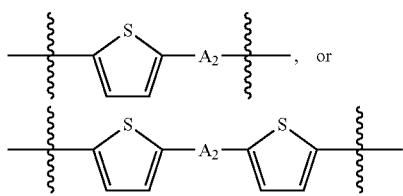

where $A_2$ is independently a substituted or unsubstituted aryl group or substituted or unsubstituted heteroaryl group. Each $B_1$ is independently selected from a an aryl or heteroaryl groups optionally substituted with one, two, or more $B_2$. Each $B_2$ is independently selected from H, a substituent, halogen, —Sn($C_1$-$C_4$ alkyl)$_4$, —Zn(halide), —Mg(halide), —B(OH)$_2$, or boronate ester, or

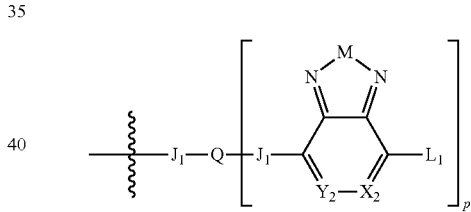

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_8$ is H, a substituent, halogen, —Sn($C_1$-$C_4$ alkyl)$_3$, —Zn(halide), —Mg(halide), —B(OH)$_2$, or boronate ester.

In some compounds of formula B, $A_1$ is a DONOR.

In some compounds of formula B, $H_2$ is

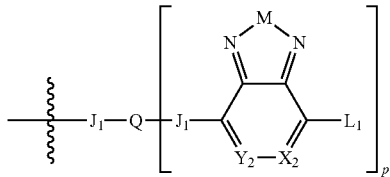

where p is 1, $H_1$ and $L_1$ are the same, and both $H_1$ and $L_1$ are both -$A_1$-$B_1$ where each $A_1$ is a DONOR. Each $B_1$ is independently selected from a an aryl or heteroaryl groups optionally substituted with one, two, or more $B_2$, Each $B_2$ is independently selected from H, a substituent, halogen, —Sn($C_1$-$C_4$ alkyl)$_4$, —Zn(halide), —Mg(halide), —B(OH)$_2$, or boronate ester, or

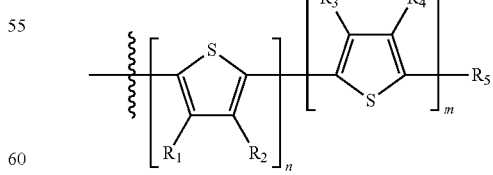

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

In some compounds of formula B, H₂ is

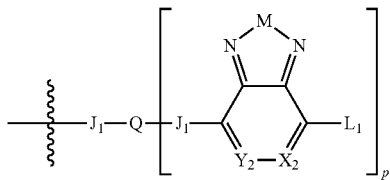

where p is 1, Q is a DONOR, each J₁ is a nonentity, H₁ and L₁ are the same, and both H₁ and L₁ are -A₁-B₁ where each A₁ is a DONOR. Each B₁ is phenyl substituted with one, two, or more B₂, and each B₂ is independently selected from a H or diarylamine.

Some compounds of formula B have formula 5:

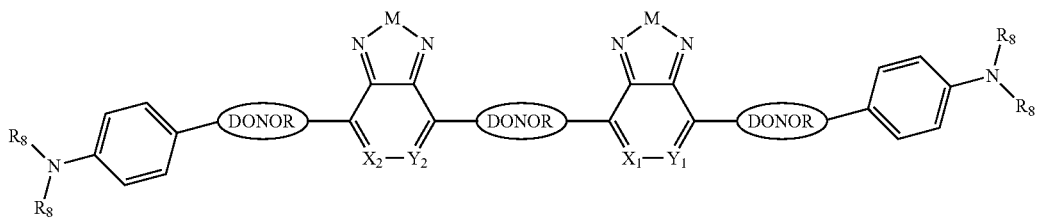

where M is selected from sulfur (S), oxygen (O), selenium (Se), tellurium (Te), —N(R₆)—, —C(R₇)₂—C(R₈)₂—, —CR₇=CR₈—, —S(O)₂—, —S(=O)—, —C(=O)—, —C(=S)—, or —C(=N—R₁)—; where R₆ is H or a substitutent; R₇ is H or a substituent; and R₈ is H or a substituent. X₁ is H or halogen and Y₁ is H or halogen, where at least one of X₁ and Y₁ is halogen. X₂ is H or halogen and each Y₂ is H or halogen, where at least one of X₂ and Y₂ is halogen. R₈ is C₆-C₃₀ aryl optionally substituted with one or more C₁-C₁₆ alkyl groups.

In some compounds according to Formula B, H₂ is

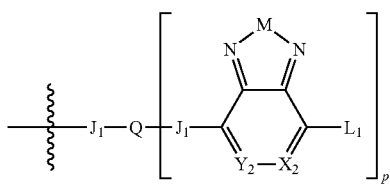

where p is 2.

In some compounds according to formula B, H₂ is

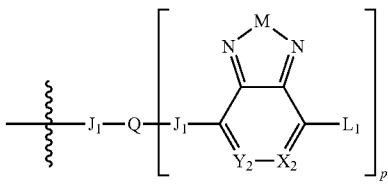

where p is 2, and H₁ and each L₁ are the same.

In some compounds according to formula B, H₂ is

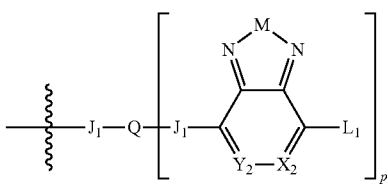

where p is 3, and H₁ and each L₁ are the same and are -A₁-B₂.

In some compounds according to formula B, J₁ is

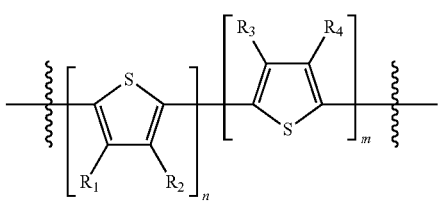

where n is an integer between 0 and 5, inclusive and m is an integer between 0 and 5, inclusive, and 1≤m+n≤5 and $R_1$, $R_2$, $R_3$, and $R_4$ are each independently H.

In some compounds according to formula B, Q is trivalent.

In some compounds according to formula B, Q is a trivalent aryl or heteroaryl group selected from

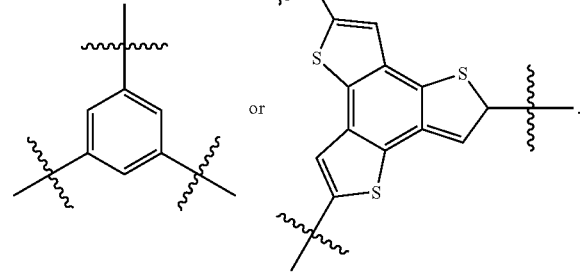

In some compounds according to formula B, $H_2$ is

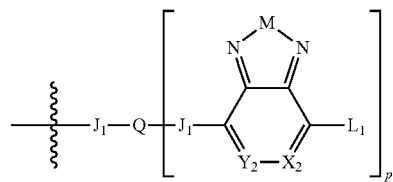

where p is 3, and $H_1$ and each $L_1$ are the same and are -$A_1$-$B_2$, where $A_1$ is a DONOR, and $B_1$ is H or a substituent, and each $J_1$ is a nonentity or

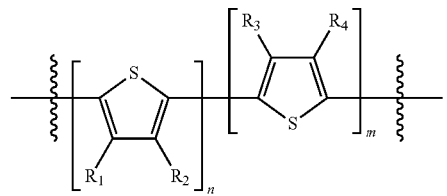

where n is an integer between 0 and 5, inclusive and m is an integer between 0 and 5, inclusive, and 1≤m+n≤5 and $R_1$, $R_2$, $R_3$, and $R_4$ are each independently H.

Some compounds according to formula B have formula 9 or 10:

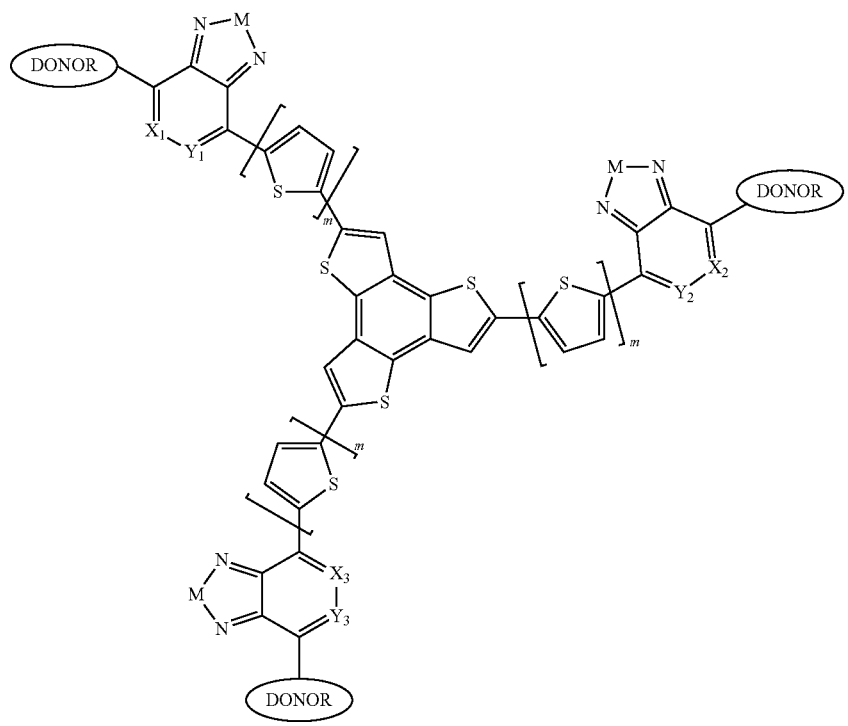

9

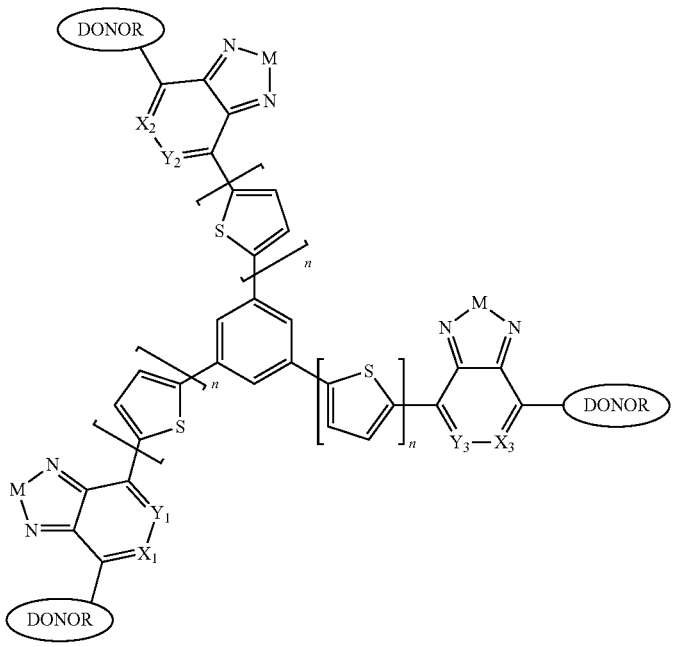

Where n is an integer from 0 to 5 inclusive; m is an integer from 0 to 5 inclusive, where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—; where $R_6$ is H or a substituent; $R_7$ is H or a substituent; and $R_8$ is H or a substituent. $X_1$ is H or halogen and $Y_1$ is H or halogen, where at least one of $X_1$ and $Y_1$ is halogen. $X_2$ is H or halogen and each $Y_2$ is H or halogen, where at least one of $X_2$ and $Y_2$ is halogen. $X_3$ is H or halogen and each $Y_3$ is H or halogen, where at least one of $X_3$ and $Y_3$ is halogen.

Compounds according to Formula B may have, for example, Formula 1, Formula 2, Formula 3, Formula 4, Formula 5, Formula 6, Formula 7, Formula 8, Formula 9 or Formula 10 as defined herein. In Formulas 1-2-3-4-5, each DONOR moiety may be the same or different. In Formulas 6-7-8, each DONOR moiety may be the same or different. In Formulas 9-10, each DONOR moiety may be the same or different.

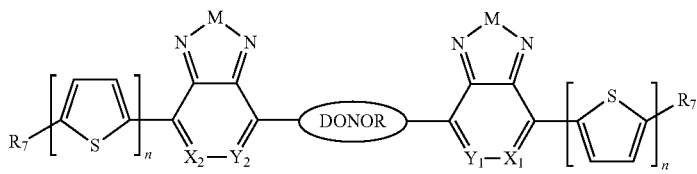

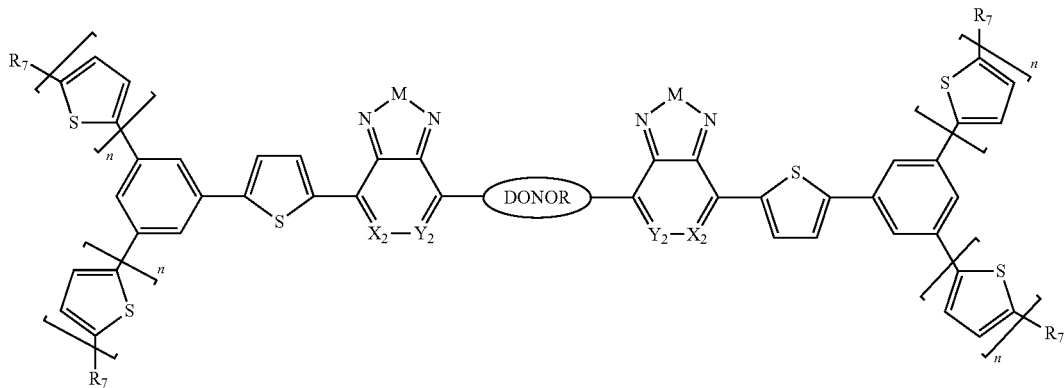

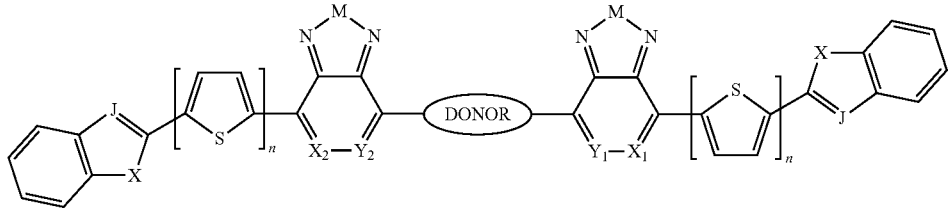
3
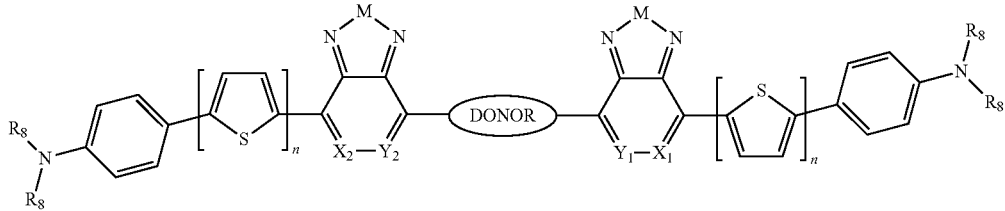
4
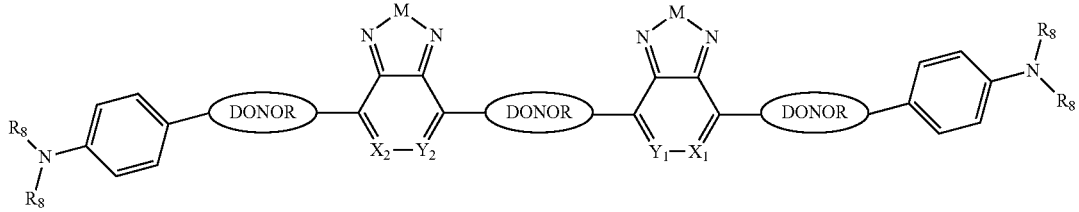
5
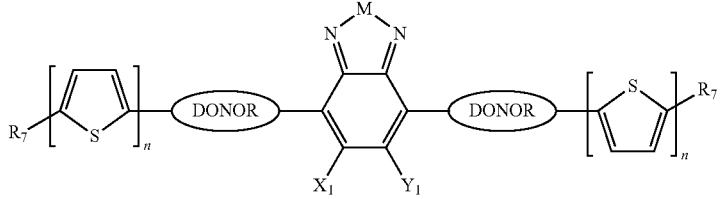
6
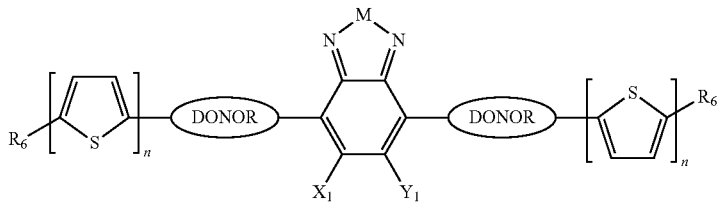
7
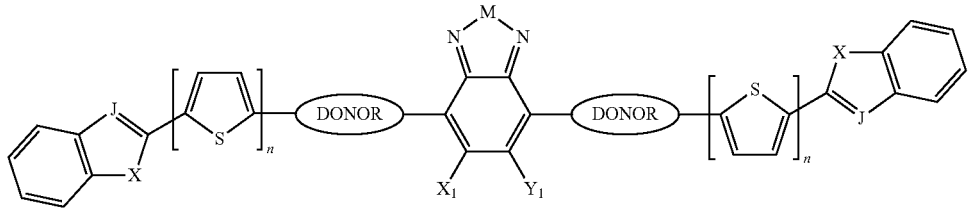
8

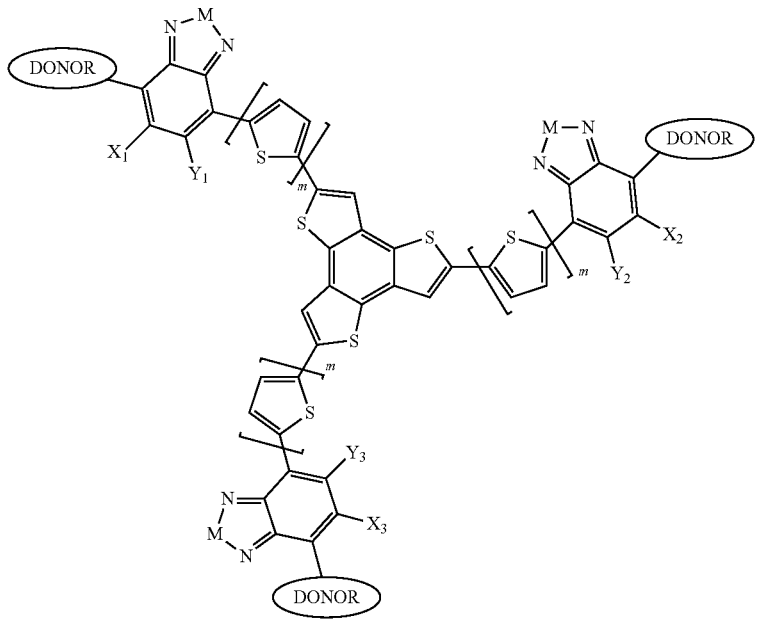

9

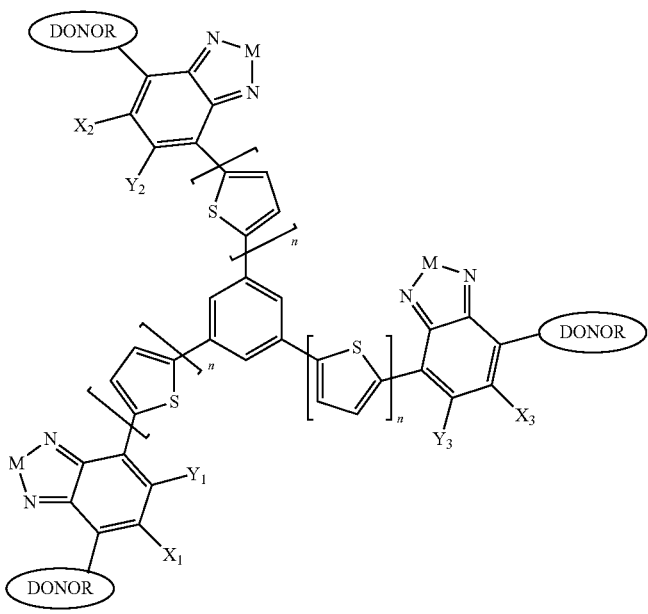

10 where n is an integer from 0 to 5 inclusive; m is an integer from 0 to 5 inclusive.

M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N-R$_1$)—; where R$_6$ is H or a substituent; R$_7$ is H or a substituent; and R$_8$ is H or a substituent. X$_1$ is H or halogen and Y$_1$ is H or halogen, where at least one of X$_1$ and Y$_1$ is halogen. X$_2$ is H or halogen and each Y$_2$ is H or halogen, where at least one of X$_2$ and Y$_2$ is halogen. X$_3$ is H or halogen and each Y$_3$ is H or halogen, where at least one of X$_3$ and Y$_3$ is halogen. R$_7$ is selected from H or a substituent. J is selected from CH and N. X is S, O, or NH when X is CH; and X is S when J is N. R$_8$ is C$_6$-C$_{30}$ aryl optionally substituted with one or more C$_1$-C$_{16}$ alkyl groups.

R$_6$ is selected from aryl, perfluoroaryl, or C$_6$-C$_{30}$ aryl optionally perfluorinated or optionally substituted with one or more C$_1$-C$_{16}$ alkyl groups.

As used throughout this application, DONOR is a heteroaromatic group, which may be, for example,

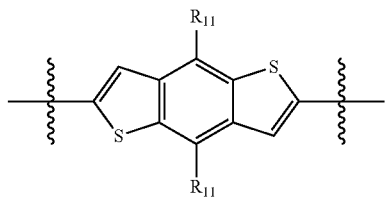

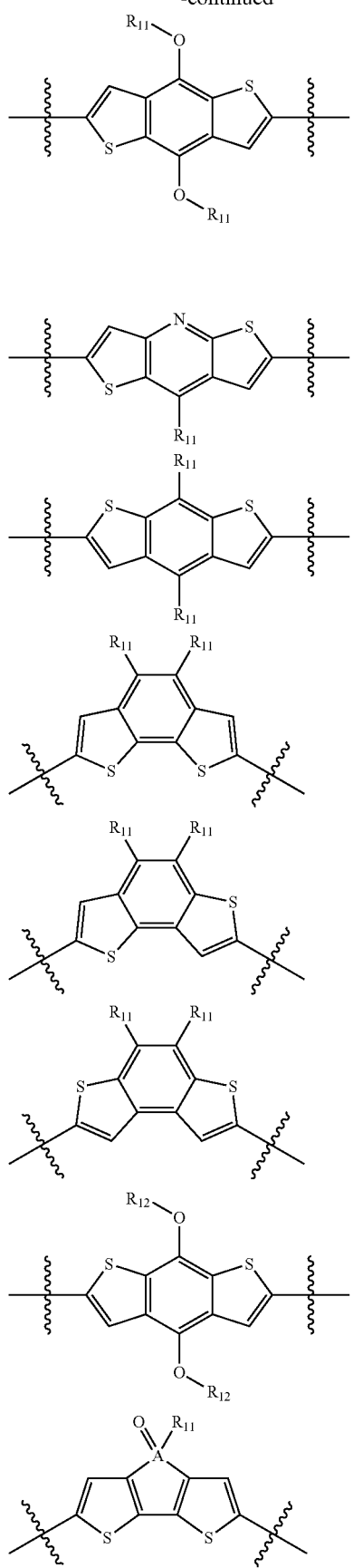
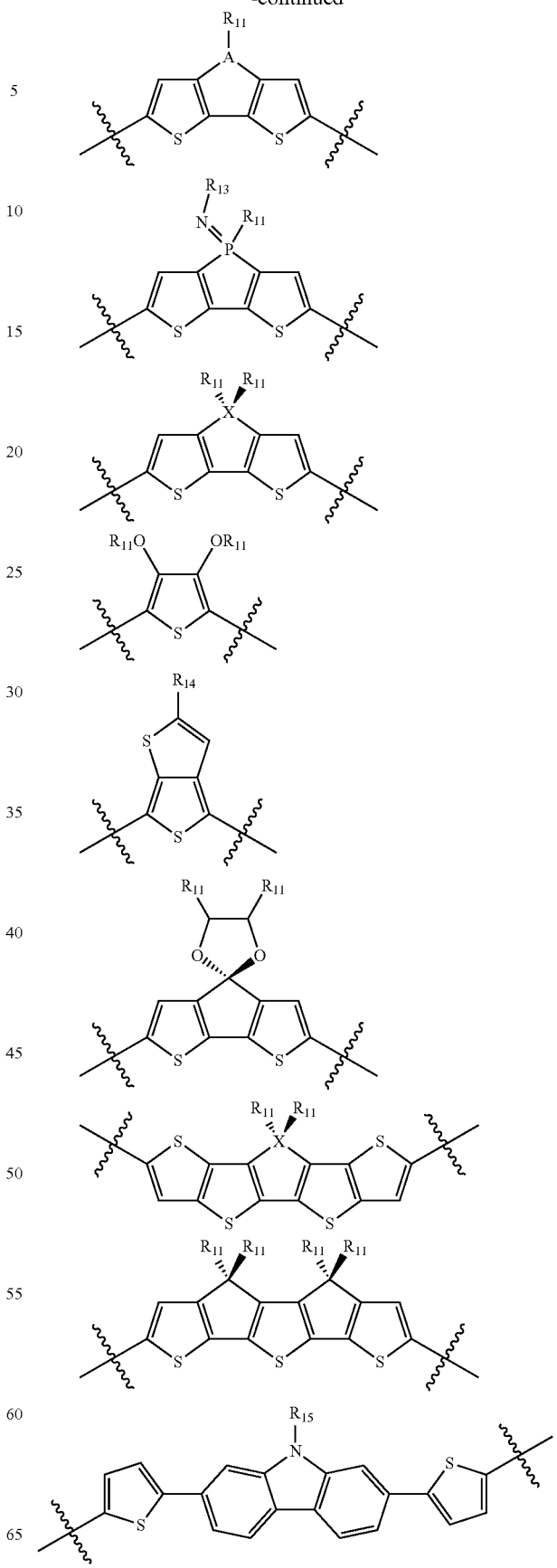

-continued

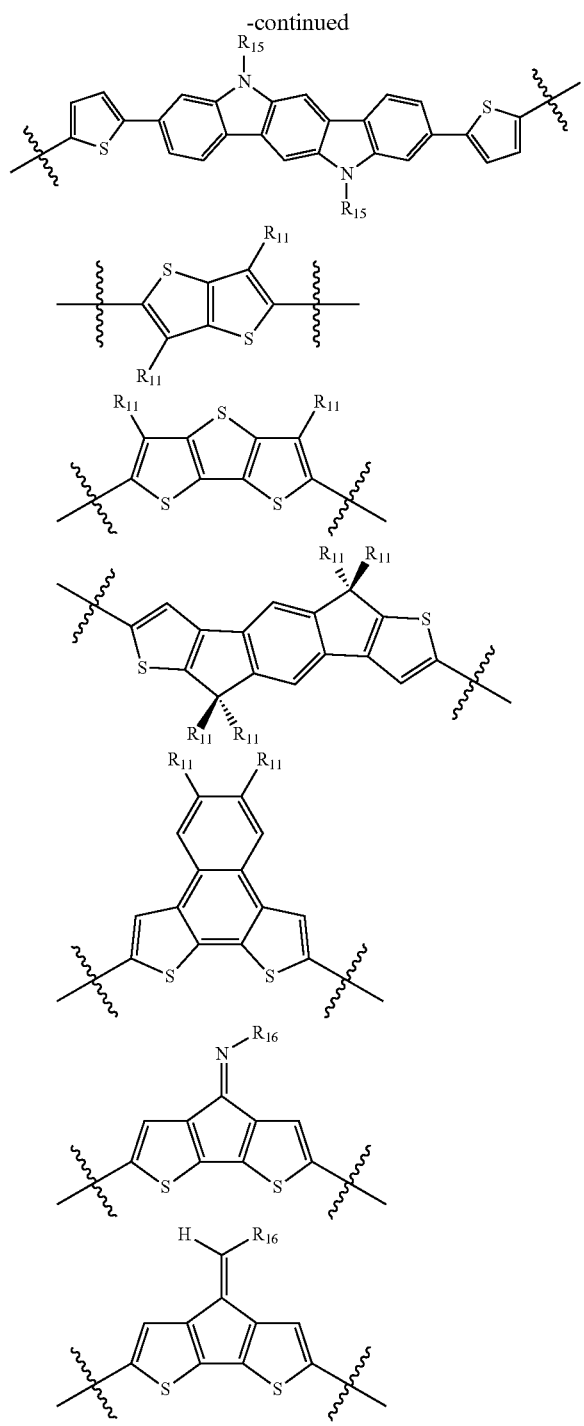

where X is C or Si. A is N or P. $R_{11}$ is selected from $C_1$-$C_{16}$ alkyl. $R_{12}$ is selected from $C_1$-$C_{16}$ alkyl, $C_6$-$C_{20}$ unsubstituted aryl, or $C_6$-$C_{20}$ aryl substituted with one or more substituent. $R_{13}$ is $C_1$-$C_{16}$ alkyl or $C_6$-$C_{20}$ aryl. $R_{14}$ is selected from $C_1$-$C_{16}$ alkyl, —O—$C_1$-$C_{16}$ alkyl, —C(=O)—O—C—$C_{16}$ alkyl, or —O—C(=O)—$C_1$-$C_{16}$ alkyl. $R_{15}$ is selected from $C_1$-$C_{16}$ alkyl, $C_6$-$C_{20}$ unsubstituted aryl, or $C_6$-$C_{20}$ aryl substituted with one or more substituent.

In any compound described herein, a substituent may be, for example, independently halogen, F, $NO_2$, CN, acyl, O-acyl, S-acyl, N-acyl, alkyl, haloalkyl, substituted or unsubstituted aryl, substituted or unsubstituted heteroaryl, alkenyl, alkoxy, alkylthio, alkylamine, arylamine, or hydroxy. As such, in any compound described herein, unless otherwise specified, $B_2$, $R_1$, $R_2$, $R_3$, $R_4$, or $R_5$ may be, independently halogen, F, $NO_2$, CN, acyl, O-acyl, S-acyl, N-acyl, alkyl, haloalkyl, substituted or unsubstituted aryl, substituted or unsubstituted heteroaryl, alkenyl, alkoxy, alkylthio, alkylamine, arylamine, or hydroxy.

In any compound described herein, at least one of $R_1$, $R_2$, $R_3$, or $R_4$ may be alkyl.

In any compound described herein, M may be S. In any compound described herein, M may be Se. In any compound described herein, M may be O.

In any compound described herein, all $R_9$ may be F.

In any compound described herein, unless otherwise specified, $A_1$ (when present) may be, for example, substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

In any compound described herein, unless otherwise specified, $A_2$ (when present) may be, for example, substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

In any compound described herein, unless otherwise specified, $B_1$ may be substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In any compound described herein, unless otherwise specified, Q may be substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, carbazole, 9,9-RR'-9H-fluorene, 9-R-9H-carbazole, 3,3'-RR'silylene-2, 2'-bithiophene, 3,3'RR'-cyclopenta[2,1-b:3,4-b']-dithiophene, where R and R'=$C_1$-$C_{30}$ alkyl or $C_6$-$C_{30}$ aryl.

In some embodiments, the non-polymeric molecules described herein have a solubility of at least about 0.1 mg/mL in an organic solvent, 1 mg/mL in an organic solvent, 5 mg/mL, 10 mg/mL in an organic solvent, 30 mg/mL in an organic solvent, or 100 mg/mL in an organic solvent. The organic solvent can be for example, chloroform, toluene, chlorobenzene, methylene dichloride, tetrahydrofuran, or carbon disulfide.

Preparation

Compounds may be prepared using methods available to a chemist of ordinary skill. In short, compounds of the invention may be assembled by metal-catalyzed (including palladium-catalyzed) cross-coupling reactions between aromatic precursors. Suitable aromatic precursors include those bearing halogen substituents, which can be reacted with, for example, boronic acid or borane substituted aromatic compounds (Suzuki coupling), alkyl stannane substituted aromatic compounds (Stille coupling), alkysilane substituted aromatic compounds (Hiyama coupling), zinc substituted aromatic compounds (Negishi coupling), among others.

For example, compounds described herein may be synthesized using as a precursor a compound of Formula C:

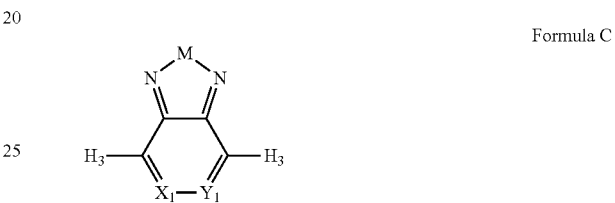

Formula C where M is selected from sulfur (S), oxygen (O), selenium (Se), tellurium (Te), —N($R_6$)—, —C($R_7$)$_2$—C($R_8$)$_2$—, —$CR_7$=$CR_8$—, —S(=O)$_2$—, —S(=O)—, —C(=O)—, —C(=S)—, or —C(=N-$R_1$)—; where $R_6$ is H or a substitutent; $R_7$ is H or a substituent; and $R_8$ is H or a substituent. $R_9$ is F, Cl, Br, or I. Substituents $H_3$ may be any substituent suitable for aromatic cross-coupling reaction. For example, $H_3$ may be Br, I, or —Sn($C_1$-$C_4$ alkyl)$_3$, or any other substituent suitable for aromatic cross-coupling reaction. For example, $H_3$ may be Cl, Br, I, —Sn($C_1$-$C_4$ allyl)$_3$, —Zn(halide), —Mg(halide), —B(OH)$_2$, or boronate ester.

Some exemplary routes to these precursors of Formula C are shown in Scheme 1.

Scheme 1

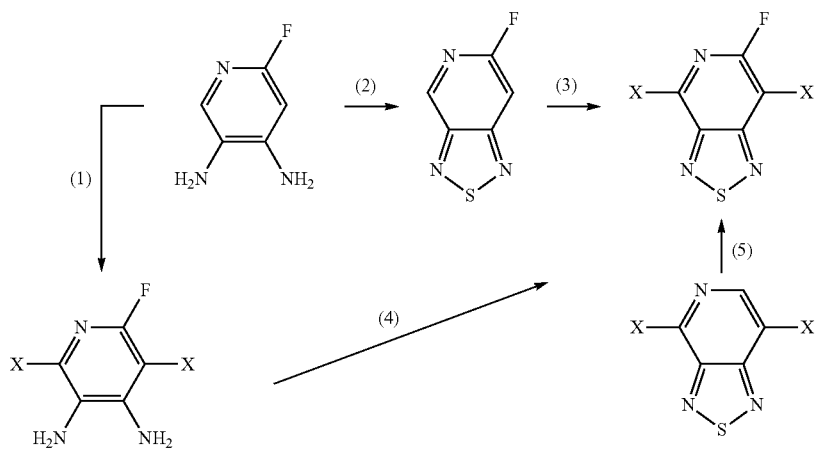

where X = halogen (Cl, Br, I)
(1) $Br_2$, HBr
(2) $SOCl_2$, $NEt_3$
(3) $Br_2$, HBr or NBS, conc. acid, or LDA, TMSCl, NBS
(4) $SOCl_2$, $NEt_3$
(5) Base, Electrophilic fluorinating agent.

The compound of Formula C may be cross-coupled with a compound having the formula:

L₁-H₁ where L is Cl, Br, I, —Sn(C₁-C₄ alkyl)₄, —Zn(halide), —Mg(halide), —B(OH)₂, or boronate ester.

Exemplary preparations are shown in the Examples below, Device architectures, materials, and fabrication Embodiments of the invention include electronic devices comprising a non-polymer compound comprising one or more groups of Formula A:

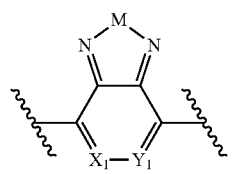

Formula A where M is selected from sulfur (S), oxygen (O), selenium (Se), tellurium (Te), —N(R₆)—, —C(R₇)₂—C(R₈)₂—, —CR₇=CR₈—, —S(=O)₂—, —S(=O)—, —C(=O)—, —C(=S)—, or —C(N—R₁)—; where R₆ is H or a substitutent; R₇ is H or a substituent and R₈ is H or a substituent; X₁ is N or C—R₉, Y₁ is N or C—R₉, and one of X₁ and Y₁ is N, and the other is C—R₉; where R₉ is F, Cl, Br, or I. In some embodiments, Formula A is a benzothiadiazole group, benzooxadizaole group, or benzotriazole group.

Embodiments of the invention include organic electronic devices comprising any compound of Formula A or Formula B, as described herein.

In some embodiments, the electronic device is a solar cell. In many solar cells, light passes though a transparent first electrode (such as ITO-coated glass), is absorbed by a donor:acceptor mixture, which results in the separation of electrical charges and migration of the charges to the electrodes, yielding a usable electrical potential.

Any electronic device described herein may have, for example, a first electrode, a second electrode and an active layer between the first and second electrode, where the active layer comprises the non-polymeric compound incorporating one or more groups of formula A or any compound according to formula B, described herein.

The first electrode may be made of materials such as, but not limited to, indium-tin oxide, indium-magnesium oxide, cadmium tin-oxide, tin oxide, aluminum- or indium-doped zinc oxide, gold, silver, nickel, palladium and platinum. In some embodiments, the first electrode has a high work function (4.3 eV or higher).

One electrode may be deposited onto a substrate. For example, the first electrode can be deposited onto a substrate, and the device can be fabricated by subsequent deposition of layers. However, the second electrode can be deposited onto a substrate, with subsequent deposition of layers. In some embodiments, the substrate may be transparent. The transparent substrate can be glass, plastic, or any other transparent material compatible with the electrode formed on the substrate.

The second electrode may be, for example, a metal electrode. Conducting metal oxides, such as indium tin oxide, zinc oxide, or cadmium oxide, can also be used as electrodes, as well as conducting organic materials, such as electrodes comprising graphene. For metal electrodes, the metal may be, for example, aluminum, silver or magnesium, but may be any metal. Nanowires such as silver nanowires or other nanostructured materials can also be used. If a transparent electrode is desired, very thin metallic layers of metals can also be used. In some embodiments, the device is annealed before and/or after evaporation of the metal electrode.

In any electronic device, one electrode may be transparent. For example the first electrode may be transparent, allowing light to enter the device, but in some embodiments, the second electrode can be transparent. In some embodiments, both electrodes are transparent. In some embodiments, the transparent electrode may be indium tin oxide (ITO) coated onto a transparent substrate.

Any device may further include an electron-blocking, exciton-blocking, or hole-transporting layer. The electron-blocking, exciton-blocking or hole-transporting layer may be adjacent to the first electrode. In some embodiments, the hole transporting layer may be, for example, poly(3,4-ethylene dioxythiophene:poly(styrenesulfonate) (PEDOT:PSS). Other hole transporting materials, such as polyaniline (with suitable dopants), or N,N'-diphenyl-N,N'-bis(3-methylphenyl)[1,1'-biphenyl]-4,4'-diamine (TPD), nickel oxide, can be used.

In some embodiments, the layer may be an electron-blocking, exciton-blocking, or hole-transporting metal oxide. Electron-blocking, exciton-blocking, or hole-transporting metal oxides include, for example, $MoO_3$, $MoO_{3-x}$, $V_2O_{5-x}$, NiO, $Ta_2O_5$, $Ag_2O$, CuO, $Cu_2O$, $CrO_{3-x}$, and $WO_3$, where x is between 0.01 and 0.99, or between 0.1 and 0.9. Other suitable materials are described in Greiner, Mark T. et al., "Universal energy-level alignment of molecules on metal oxides," Nature Materials, DOI: 10.1038/NMAT3159 (Nov. 6, 2011).

Any device may further include a hole-blocking, exciton-blocking, or electron-transporting layer. In some embodiments, this layer is adjacent to the second electrode, and may optionally be deposited on top of the donor-acceptor film in order to block holes or excitons, act as an optical buffer, or otherwise benefit the electrical characteristics of the device. 2,9-dimethyl-4,7-diphenyl-1,10-phenanthroline can act as a hole-blocking or exciton-blocking material, while 4,4',4"-tris[N-(3-methylphenyl)-N-phenylamino]triphenylamine and polyethylene dioxythiophene can act as exciton-blocking materials. Other materials that can be used between the second electrode and the active layer are titanium suboxide, ZnO, $Cs_2CO_3$, and $ZrO_3$. Additional materials suitable for use are described in Greiner, Mark T. et al., "Universal energy-level alignment of molecules on metal oxides," Nature Materials, DOI: 10.1038/NMAT3159 (Nov. 6, 2011).

In any device, the active layer may further include an electron acceptor. The electron acceptor may be, for example, a fullerene such as [6,6]-phenyl C61-butyric acid methyl ester (PCBM), but may be a different fullerene (including, but not limited to, C71-PCBM), a tetracyanoquinodimethane, a vinazene, a perylene tetracarboxylic acid-dianhydride, a perylene tetracarboxylic acid-diimide, an oxadiazole, carbon nanotubes, or any other organic electron acceptor, such as those compounds disclosed in U.S. 2008/0315187.

In other embodiments, the electron acceptor is an inorganic acceptor selected from $TiO_2$ (titanium dioxide), $TiO_x$ (titanium suboxide, where x<2) and ZnO (zinc oxide). The titanium dioxide can be anatase, rutile, or amorphous. A titanium dioxide layer can be prepared by depositing a sol-gel precursor solution, for example by spincasting or doctorblading, and sintering at a temperature between about 300° C. and 500° C. When an inorganic layer is used, component (c) of the optoelectronic device described above can be comprised of a layer of electron-donating chromophores of the general Formula I-VII and an inorganic electron-acceptor layer. Alternatively, the inorganic material can be dispersed in the electron-donating chromophores to create a single layer. Preparation of $TiO_2$ for use in solar cells is described in Brian O'Regan & Michael Gritzel, Nature 353:737 (1991) and Serap Günes et al., 2008 Nanotechnology 19 424009.

When titanium suboxide according to the formula TiO, where x<2, is used, x may follow the following relationships: $1<x<1.98$, $1.1<x<1.9$, $1.2<x<1.8$, or $1.3<x<1.8$. X in the formula $TiO_x$ can be, for example, <2, <1.98, <1.9, <1.8, <1.7, or <1.6.

In some embodiments, the device further includes a dielectric layer.

In some embodiments, the device further includes a third electrode.

Some devices may be tandem solar cells, such as those disclosed in US 2009/0126779. Tandem solar cells are arranged so that light which is not absorbed by a first solar cell passes to a second solar cell, where the second solar cell may have a smaller bandgap than the first solar cell in order to absorb electromagnetic radiation that cannot be usefully absorbed by the first solar cell.

Some devices may include passivating layers, such as those disclosed in US 2007/0221926 and US 2007/0169816.

Some devices may include optical spacer layers, such as those disclosed in US 2006/0292736.

One method of fabricating the optoelectronic device is as follows: A conductive, transparent substrate is prepared from commercially available indium tin oxide-coated glass and polystyrenesulfonic acid doped polyethylenedioxythiophene using standard procedures. A solution containing a mixture of the donor and acceptor materials is prepared so that the ratio of donor to acceptor is between 1:99 and 99:1 parts by mass; or in some embodiments between 3:7 and 7:3 parts by mass. The overall concentration of the solution may range between 0.1 mg/mL and 100 mg/mL, but the range of 10 mg/mL and 30 mg/mL is particularly suitable for some embodiments. Non-polymeric molecules are used that have a solubility of at least about 0.1 mg/mL in an organic solvent, 1 mg/mL in an organic solvent, 5 mg/mL, 10 mg/mL in an organic solvent, 30 mg/mL in an organic solvent, or 100 mg/mL in an organic solvent. The organic solvent can be selected from chloroform, toluene, chlorobenzene, methylene dichloride, tetrahydrofuran, or carbon disulfide.

Useful solvents include chloroform, toluene, chlorobenzene, methylene dichloride, tetrahydrofuran, and carbon disulfide. However, the solvent used may be any solvent which dissolves or partially dissolve both donor and acceptor materials and has a non-zero vapor pressure.

The solution of donor and acceptor is deposited by spin casting, doctor-blading, ink-jet printing, roll-to-roll coating, slot-dye coating, gravure coating, or any process which yields a continuous film of the donor-acceptor mixture such that the thickness of the film is within the range of 10 to 1000 nm, or between 50 and 150 nm in some embodiments.

In some embodiments, the layer of the donor and acceptor is cast from a solution comprising a solvent and the electron donor and the electron acceptor. The solvent can comprise chloroform, thiophene, trichloroethylene, chlorobenzene, carbon disulfide, a mixture of any of the foregoing solvents or any solvent or solvent mixture that dissolves both the donor and acceptor organic molecule. The solvent can also include processing additives, such as those disclosed in US Patent Application Publication Nos. 2009/0032808, 2008/0315187, or 2009/0108255. For example, 1,8-diiodooctane (DIO) can be added to the solvent/donor/acceptor mixture in an amount of 0.1-10% by volume. The additive, such as 2% DIO, can be added to any organic solvent used to cast the layer of donor/acceptor, such as chloroform. The solvent can also include doping agents such as molybdenum trioxide ($MoO_3$). For example, $MoO_3$ can be added to the solvent/donor/acceptor mixture in an amount of 0.1-10% by volume.

Finally, an electrode, such as a metal electrode, is deposited on top of the structure by thermal evaporation, sputtering, printing, lamination or some other process. Conducting metal oxides, such as indium tin oxide, zinc oxide, or cadmium oxide, can also be used as electrodes, as well as conducting organic materials, such as electrodes comprising graphene. For metal electrodes, the metal can be, for example, aluminum, silver or magnesium, but may be any metal. Nanowires such as silver nanowires or other nanostructures can also be used. If a transparent electrode is desired, very thin metallic sheets of metals can also be used. In some embodiments, the device is annealed before and/or after evaporation of the metal electrode.

Hole and electron mobilities are important parameters to consider in the fabrication/function of bulk heterojunction solar cells. For optimal device performance, a balance in the mobility of both charge carriers is desirable. The electron and hole mobilities may both be on the order of $10^{-4}$ $cm^2/Vs$ or higher. In some embodiments, the electron mobilities are on the order of $10^{-3}$ $cm^2/Vs$ or higher. In some embodiments, the electron mobilities are on the order of $10^{-4}$ $cm^2/Vs$ or higher, and the hole mobilities are between $10^8$ $cm^2/Vs$ and $10^{-4}$ $cm^2/Vs$ or higher. In other embodiments, the electron mobilities are on the order of $10^{-3}$ $cm^2/Vs$ or higher, and the hole mobilities are between $10^{-8}$ $cm^2/Vs$ and $10^{-4}$ $cm^2/Vs$ or higher.

Optoelectronic devices of the present invention have excellent photovoltaic properties. In some embodiments, the power conversion efficiency (PCE) is at least 0.5%, at least 1.0%, at least 2.0%, or at least 3.0%. In some embodiments, the short circuit current density is greater than 3.0 $mA/cm^2$, but may be greater than 8 $mA/cm^2$ in some embodiments. In some embodiments, the open circuit voltage is between 0.3 and 1.0 V or higher. In some embodiments, the device exhibits an external quantum efficiency of approximately 35% or greater between 300 and 800 nm.

The morphological properties of the donor:acceptor films can be measured using atomic force microscopy or other surface-sensitive techniques. The films may have, for example, a root-mean-squared surface roughness of less than 1.0 nm or less than 0.5 nm in some embodiments.

For embodiments of the devices using an inverted device architecture, the first electrode can comprise Au or another material having a work function higher than the work function of the second electrode, while the second electrode can comprise an ITO substrate modified using a self-assembled monolayer of 3-aminopropyltrimethoxysiloxane or another material having a work function lower than the work function of the first electrode.

FIG. 1 provides a schematic illustration of an electronic or optoelectronic device 100 according to an embodiments of the current invention. The electronic or optoelectronic device 100 has a first electrode 102, a second electrode 104, spaced apart from said first electrode 102, and an active layer between said first electrode 102 and said second electrode 104. The active layer 106 can include any non-polymeric compound of formula A or formula B described herein. The first electrode 102 may be, for example, a transparent anode of indium-tin-oxide (ITO). The second electrode 104 may be, for example, a metal aluminum cathode.

In some embodiments, the electronic or optoelectronic device 100 can include a hole transporting layer 108 between the first electrode 102 and the active layer 106. The hole transporting layer 108 can be, for example, PEDOT:PSS. In some embodiments, the first electrode 102 can be formed on a substrate 110. The substrate 110 can be a transparent substrate in some embodiments. In some embodiments, the substrate 110 can be glass.

EXAMPLES

Example 1

Synthesis of 4,7-dibromo-6-fluoro-[1,2,5]thiadiazolo[3,4-c]pyridine (FPT)

FPT may be prepared following paths (1) and (4) in Scheme 1 by reaction of 6-fluoropyridine-3,4-diamine with bromine (Br$_2$) in hydrobromic acid (HBr):

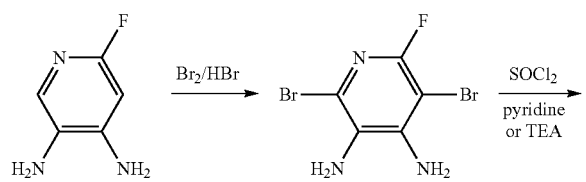

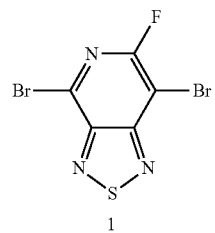

as described by Zhuo et al. (Angewandte Chemie, International Edition, vol. 49, no. 43, pp. 7992-7995, S7992/1-S7992/11, 2010), which is incorporated herein by reference in its entirety.

Alternative synthesis of 4,7-dibromo-6-fluoro-[1,2,5]thiadiazolo[3,4-c]pyridine (FPT)

FPT may be prepared according to path (5) in Scheme 1 by fluorination of 4,7-dibromo-[1,2,5]thiadiazolo[3,4-c]pyridine with a suitable electrophilic fluorinating agent in the presence of base. Some suitable electrophilic fluorinating agents include N-fluorobenzenesulfonamide (NSFI), Selectfluor® (I and II),

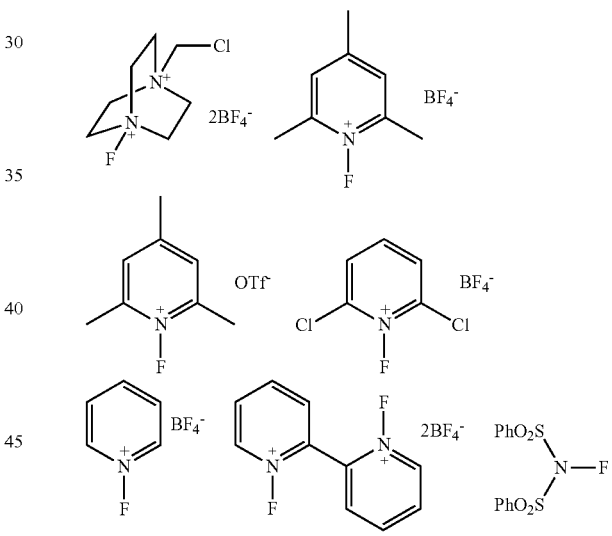

and other commercially available "F+" reagents. Suitable bases include potassium bis(trimethylsilyl)amide (KHMDS), lithium bis(trimethylsilyl)amide (LHMDS), Lithium 2,2,6,6-tetramethylpiperidide (LTMP), lithium diisopropyl amide (LDA) and related "bulky" amines which have high kinetic basicity.

In one example, to a stirring solution of 4,7-dibromo-[1,2,5]thiadiazolo[3,4-c]pyridine (110 mg, 0.4 mmol) at 0° C. or −20° C. in 2 mL of toluene was added strong base (e.g., TMP-MgClLiCl (1M solution, Aldrich)). After stirring for thirty minutes the reaction was quenched with an appropriate electrophile (e.g., 2,4,6-trimethyl-1-fluoropyridinium tetrafluoroborate) at the same temperature and allowed to stir for thirty minutes before coming to room temperature. The reaction mixture was diluted with dichloromethane and washed with aqueous base (1 M, NaOH) and water/brine.

The organic phase was dried (Na₂SO₄) and concentrated in vacuo to give the crude product.

Compound 1 can also be prepared by electrophilic aromatic substitution with F⁺ under acidic conditions:

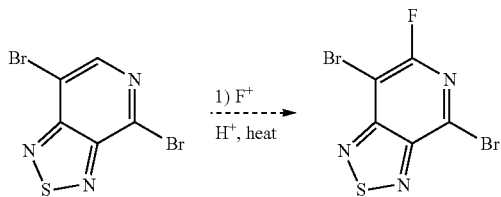

F⁺ = NFSi, Selectfluor (I and II), 1-fluoropyridinium tetrafluoroborate, etc.
H⁺ = H₂SO₄, HBr, HOTf This route is also suitable with more electron rich molecules:

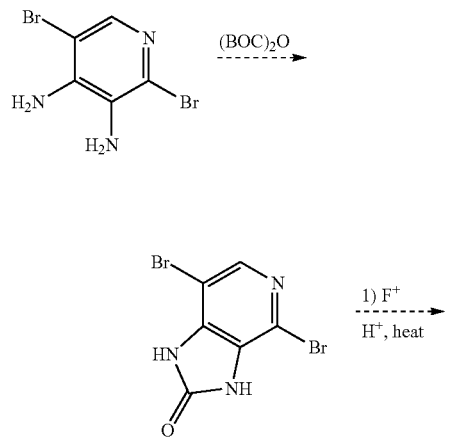

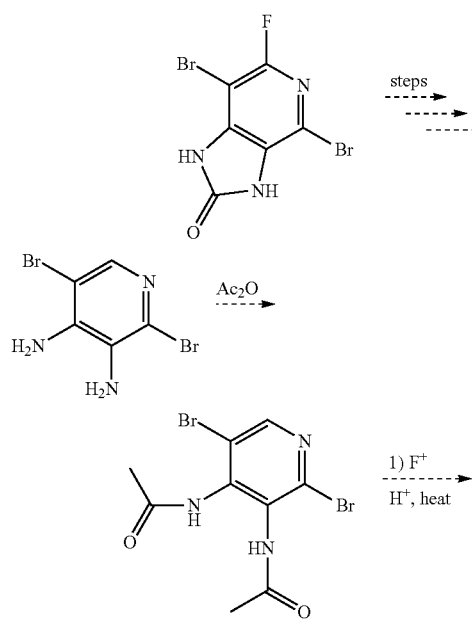

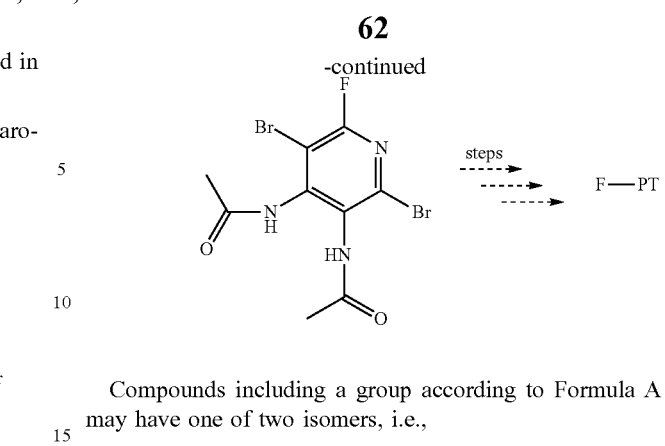

Compounds including a group according to Formula A may have one of two isomers, i.e.,

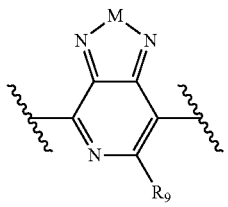

and, separately,

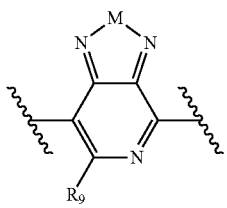

In one exemplary synthesis, a first isomer of one exemplary compound may be prepared by first substituting at the position α to the pyridine nitrogen, for example:

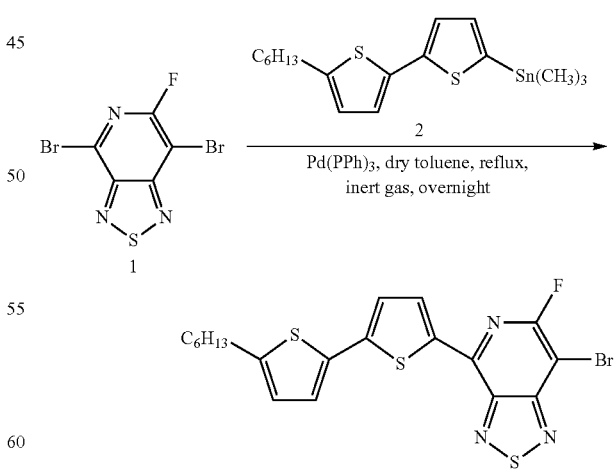

Compound 3 can also be prepared by fluorination with an electrophilic fluorinating reagent ("F⁺") of a non-halogenated analog:

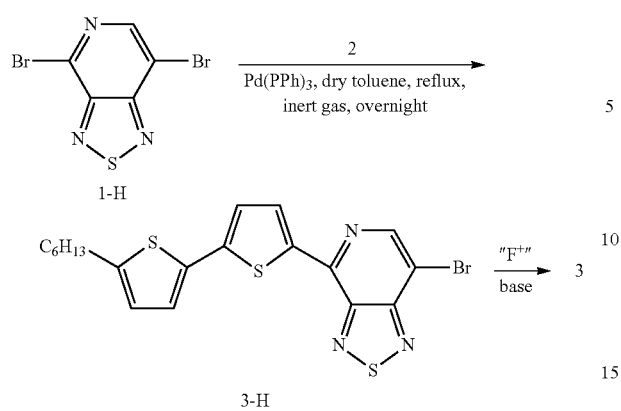

In one example, 3-H was converted to 3 according to the following method. To a stirring solution of 3-H (200 mg, 0.4 mmol) at the 0° C. or −20° C. in toluene (2 mL) was added TMP-MgClLiCl (1M solution, Aldrich). After stirring for thirty minutes the reaction was quenched with an appropriate electrophile (e.g., 2,4,6-trimethyl-1-fluoropyridinium tetrafluoroborate) at the same temperature and allowed to stir for thirty minutes before coming to room temperature. There action mixture was diluted with dichloromethane and washed with aqueous base (1 M, NaOH) and water/brine. The organic phase was dried ($Na_2SO_4$) and concentrated in vacuo to give the crude product. NMR analysis of the crude reaction mixture indicated that no deprotonation had occurred and/or signs of decomposition were evident.

In another example, 3-H was converted to 3 according to the following method.

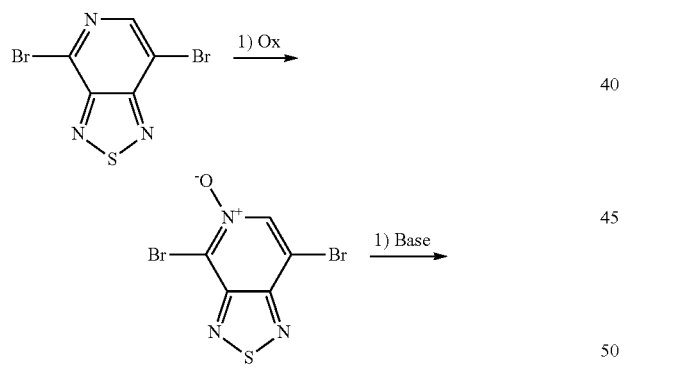

Formation of the N-Oxide of 3-H can help direct ortho metallation in addition to a reduction in the pKa of the alpha proton. (In the above reaction, "E+" represents an electrophile, such as an electrophilic F species). In a related system, (below), the N-Oxide can react in an enolate type fashion.

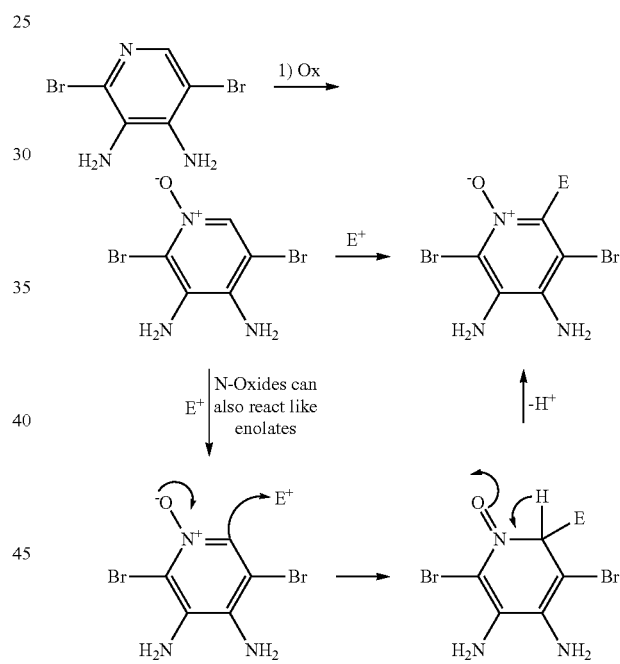

Compound 3 is a precursor to the first isomer:

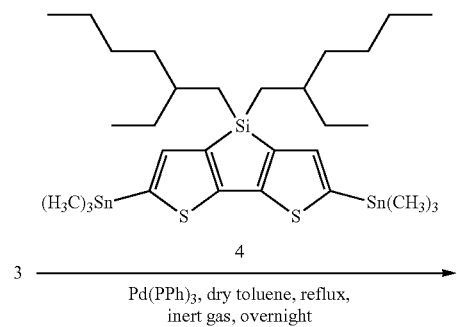

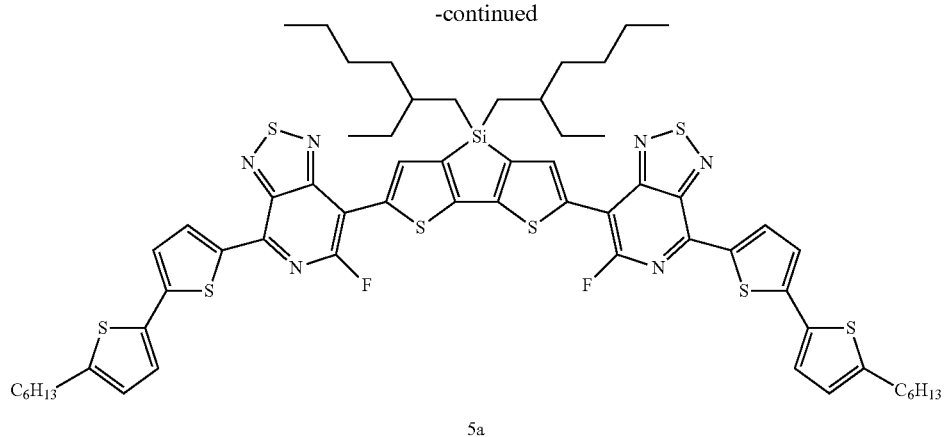
5a
The second isomer can be prepared by first substituting at the position (3 to the pyridine nitrogen, e.g., by first coupling 1 to 4 (instead of 3):
Alternatively, compound 6 can be prepared by fluorination with an electrophilic fluorinating reagent ("F+") of a non-halogenated analog:
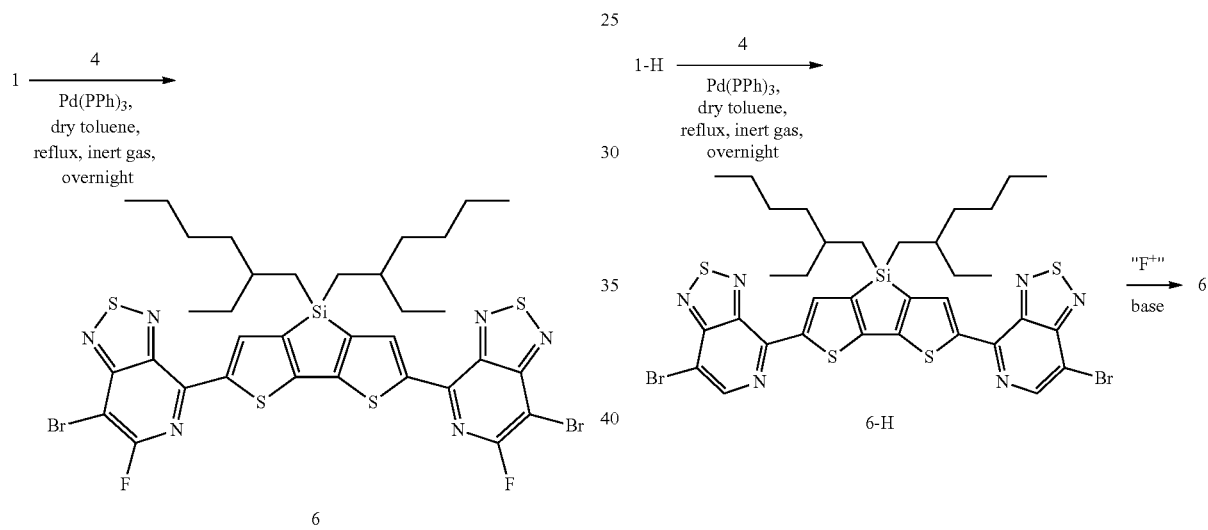
Compound 6 is a precursor to the second isomer:
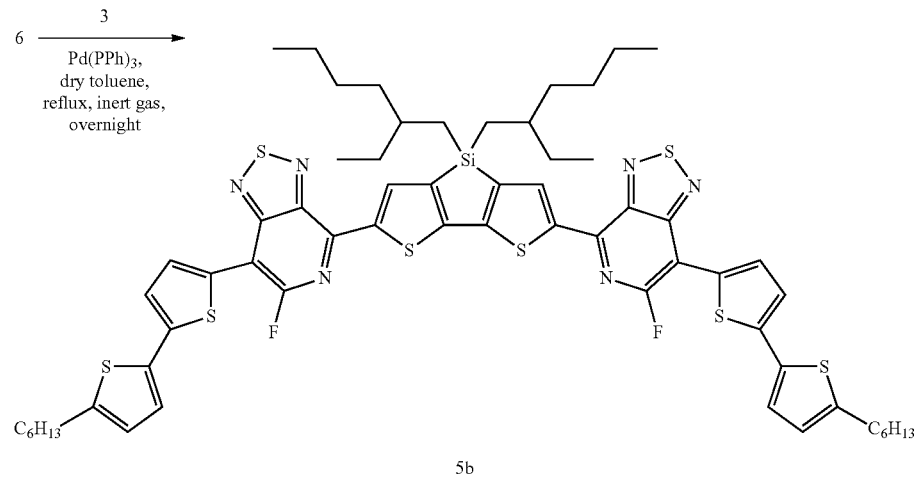
5b In another example, compounds described herein may be synthesized by fluorination with an electrophilic fluorinating reagent ("F+") of a non-halogenated analog:

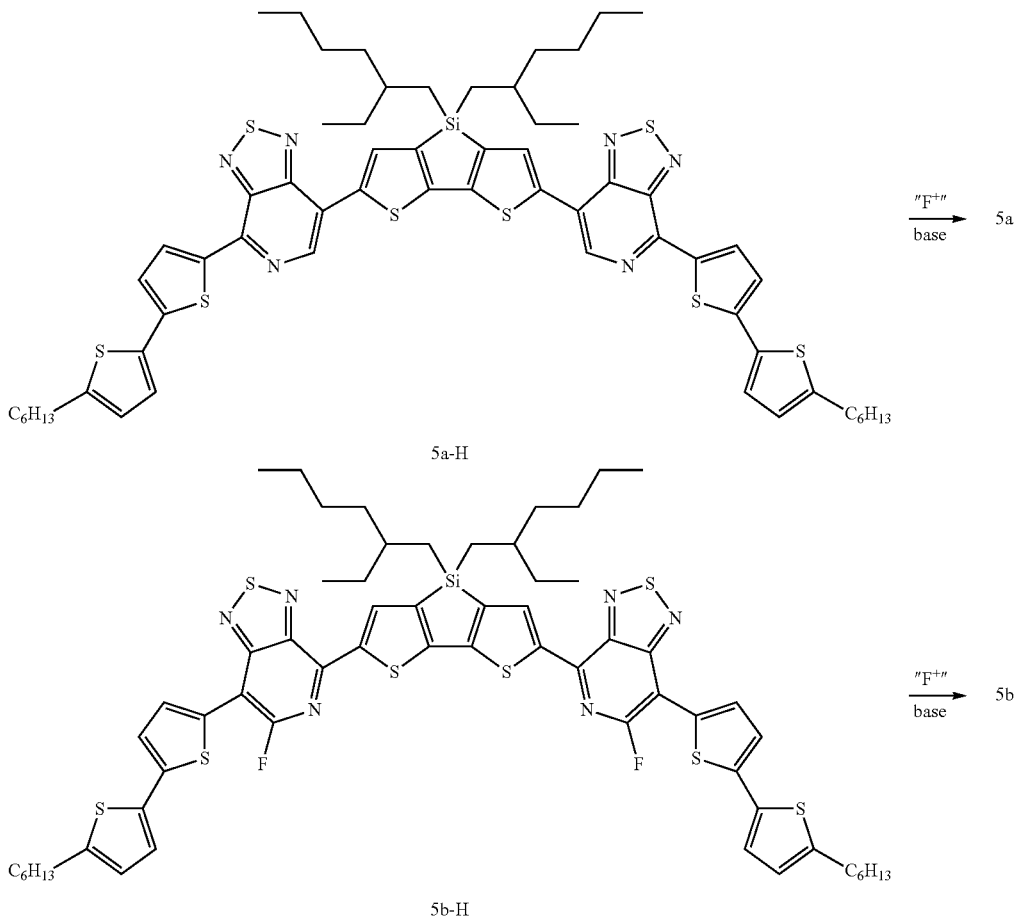

Example 2—Determination of HOMO-LUMO Values

Calculations: HOMO-LUMO values may be calculated, for example, using the Spartan '10 program. Optimized gas-phase structures may be obtained using the density functional theory (DFT) method B3LYP in conjunction with 6-31G(d,p) basis set, i.e., B3 LYP/6-31 G(d,p).

Example 3—General Procedures for Fabrication of Devices

Device Fabrication: Solar cells may be fabricated on patterned ITO-coated glass substrates. The ITO-coated glass substrates may first be cleaned with detergent, ultrasonicated in water, acetone and isopropyl alcohol, and subsequently dried overnight in an oven. $MoO_3$ films may be thermally evaporated onto UV-Ozone cleaned ITO substrates at a rate of 0.1 Å $s^{-1}$ under a vacuum of about $1 \times 10^{-6}$ torr. The thickness of the $MoO_3$ film may be, for example, approximately 13 nm. A solution containing a mixture of a compound according to formula A and [70]PCBM in chlorobenzene at a total solids concentration of, for example, 35 mg $ml^{-1}$ may spin-cast on top of the $MoO_3$ films at a spin speed of 1500 rpm. The composition of the active layer may include, for example, a 60:40 ratio of non-polymeric compound and [70]PCBM with or without 1,8-diiodooctane.

In other devices, PEDOT:PSS 4083 may be spin cast onto UV-ozone cleaned ITO then thermally annealed for 30 m at 150° C. The solution containing a mixture of non-polymeric compound and [70]PCBM in chlorobenzene at a total solids concentration of, for example, 35 mg $ml^{-1}$ may be spin-cast on top of the PEDOT:PSS films at a spin speed of 1500 rpm with the same composition as previously described.

The active layers may be heated at 70° C. for 10 min to evaporate any residual solvent. Finally, an aluminum cathode (~100 nm) may be deposited through a shadow mask by thermal evaporation under a vacuum of about $1 \times 10^{-6}$ torr. The active area of the device may be, for example, about 15 $mm^2$. The devices may be finally annealed at 90° C. for 2 m.

Device Testing.

Current density-voltage (J-V) characteristics may be measured using a Keithley 2602A Source Measure Unit while illuminated with a simulated 100 $mWcm^{-2}$ AM 1.5G light source using a 300 W Xe arc lamp with an AM1.5 global filter. Solar-simulator illumination intensity may be measured using a standard silicon photovoltaic with a protective KG1 filter calibrated by the National Renewable Energy Laboratory.

For organic photovoltaic devices, the overall PCE is determined by the equation:

$$PCE = (V_{oc} * J_{sc} * FF) / P_{in}$$

where Voc is the open circuit voltage, Jsc is the short-circuit current density, FF is the fill factor and Pin is the incident light power. Voc is the voltage at which there is no current flow in the device while the Jsc is the amount of current flowing when no voltage is applied. Values may be derived from the current density-voltage (J-Y) graph.

The disclosures of all publications, patents, patent applications and published patent applications referred to herein by an identifying citation are hereby incorporated herein by reference in their entirety.

As described herein, all embodiments or subcombinations may be used in combination with all other embodiments or subcombinations, unless mutually exclusive.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

As described herein, all embodiments or subcombinations may be used in combination with all other embodiments or subcombinations, unless mutually exclusive.

What is claimed is:

1. A compound of Formula I:

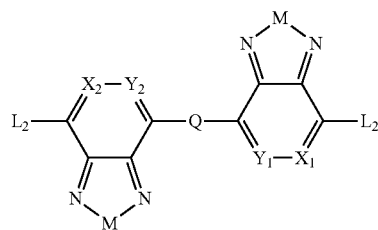

Formula I where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N—R$_1$)—;

where R$_1$ is H or a substituent;
R$_6$ is H or a substituent;
R$_7$ is H or a substituent;
R$_8$ is H or a substituent;
X$_1$ is N or C—R$_9$, Y$_1$ is N or C—R$_9$, one of X$_1$ and Y$_1$ is N, and the other is C—R$_9$; where R$_9$ is F, Cl, Br, or I;

X$_2$ is N or C—R$_9$, Y$_2$ is N or C—R$_9$, one of X$_2$ and Y$_2$ is N, and the other is C—R$_9$; where R$_9$ is F, Cl, Br, or I;

Q is a bivalent aryl or heteroaryl group;

each L$_2$ is independently —B$_2$ or -A$_1$-B$_2$ where A$_1$ is independently selected from substituted or unsubstituted aryl group, substituted or unsubstituted heteroaryl group,

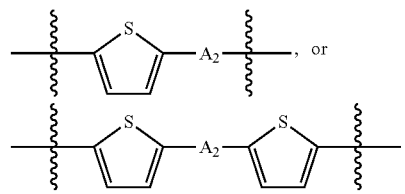

where A$_2$ is independently a substituted or unsubstituted aryl group or substituted or unsubstituted heteroaryl group;

each B$_2$ is independently selected from H, a substituent, halogen, —Sn(C$_1$-C$_4$ alkyl)$_4$, —Zn(halide), —Mg(halide), —B(OH)$_2$, or boronate ester, or

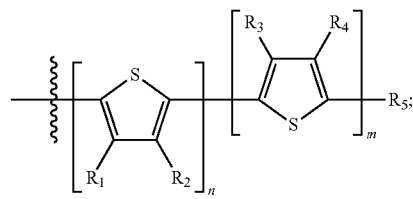

where n is an integer between 0 and 5, inclusive and m is an integer between 0 and 5, inclusive, and 1≤m+n≤5; and where R$_1$, R$_2$, R$_3$, and R$_4$ are each independently H or a substituent, R$_5$ is H, a substituent, halogen, —Sn(C$_1$-C$_4$ alkyl)$_3$, —Zn(halide), —Mg(halide), —B(OH)$_2$, or boronate ester.

2. A compound of claim 1, having Formula II:

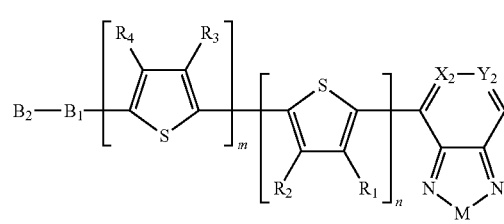 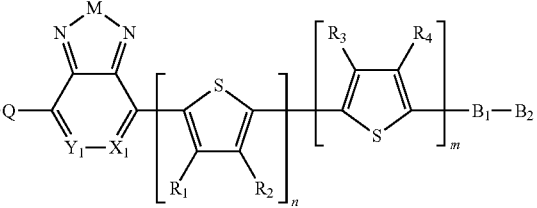

where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N—R$_1$)—;

where R$_1$ is H or a substituent;
R$_6$ is H or a substituent;
R$_7$ is H or a substituent;
R$_8$ is H or a substituent;

$X_1$ is N or C—$R_9$, $Y_1$ is N or C—$R_9$, one of $X_1$ and $Y_1$ is N, and the other is C—$R_9$; where $R_9$ is F, Cl, Br, or I;

$X_2$ is N or C—$R_9$, $Y_2$ is N or C—$R_9$, one of $X_2$ and $Y_2$ is N, and the other is C—$R_9$; where $R_9$ is F, Cl, Br, or I;

Q is a bivalent aryl or heteroaryl group;

each $B_1$ is independently selected from a an aryl or heteroaryl groups;

each $B_2$ is independently selected from H, a substituent, halogen, —Sn($C_1$-$C_4$ alkyl)$_4$, —Zn(halide), —Mg(halide), —B(OH)$_2$, or boronate ester.

3. A compound of claim 2 wherein $B_1$ is a substituted or unsubstituted thiophene.

4. A compound of claim 3, wherein Q is independently selected from substituted or unsubstituted thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl.

5. A compound of claim 2, wherein $B_1$ is independently selected from substituted or unsubstituted thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole.

6. A compound of claim 2, wherein Q is 3,3'-RR'silylene-2,2'-bithiophene and R and R' are both $C_1$-$C_{30}$ alkyl.

7. A compound of claim 2, where Q is

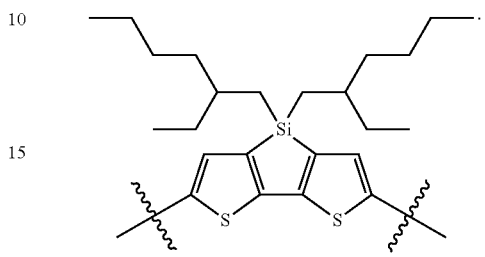

8. A compound of claim 7, where n+m=1.

9. A compound of claim 8, where $B_1$ is thiophene.

10. A compound of claim 9, where $B_2$ is alkyl.

11. A compound of claim 2, having the structure

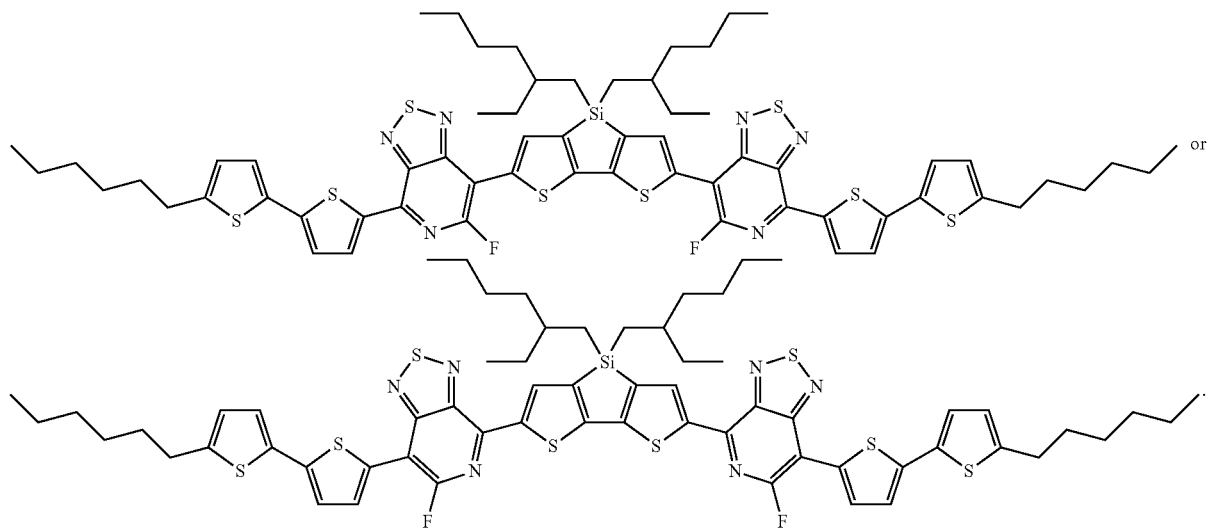

12. A compound of claim 1, wherein Q is independently selected from substituted or unsubstituted thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene where R and R'=$C_1$-$C_{30}$ alkyl or $C_6$-$C_{30}$ aryl.

13. A compound of claim 1, wherein each $L_2$ is -$A_1$-$B_2$ and each $A_1$ is selected from substituted or unsubstituted thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole.

14. A compound of claim 1, wherein each $L_2$ is $B_2$ and $B_2$ is

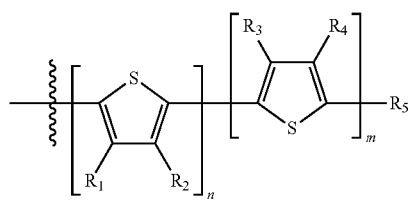

where n is an integer between 0 and 5, inclusive and m is an integer between 0 and 5, inclusive, and $1 \leq m+n \leq 5$; and where $R_1$, $R_2$, $R_3$, $R_4$ and $R_5$ are each independently H or a substituent.

15. A compound having Formula IV-V:

Formula IV-V

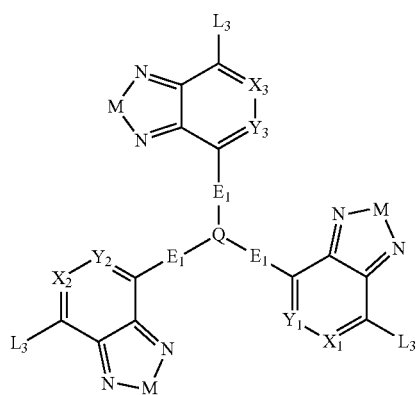

where M is selected from sulfur (S), oxygen (O), selenium (Se), tellurium (Te), —N($R_6$)—, —C($R_7$)$_2$—C($R_8$)$_2$—, —CR$_7$=CR$_8$—, —S(=O)$_2$—, —S(=O)—, —C(=O)—, —C(=S)—, or —C(=N—$R_1$)—;

where $R_1$ is H or a substituent;

$R_6$ is H or a substituent;

$R_7$ is H or a substituent;

$R_8$ is H or a substituent;

$X_1$ is N or C—$R_9$, $Y_1$ is N or C—$R_9$, one of $X_1$ and $Y_1$ is N, and the other is C—$R_9$; where $R_9$ is F, Cl, Br, or I;

$X_2$ is N or C—$R_9$, $Y_2$ is N or C—$R_9$, one of $X_2$ and $Y_2$ is N, and the other is C—$R_9$; where $R_9$ is F, Cl, Br, or I;

$X_3$ is N or C—$R_9$, $Y_3$ is N or C—$R_9$, one of $X_3$ and $Y_3$ is N, and the other is C—$R_9$; where $R_9$ is F, Cl, Br, or I;

Q is a trivalent aryl or heteroaryl group;

each $E_1$ is independently either nonentity, substituted or unsubstituted aryl, substituted or unsubstituted heteroaryl groups, or

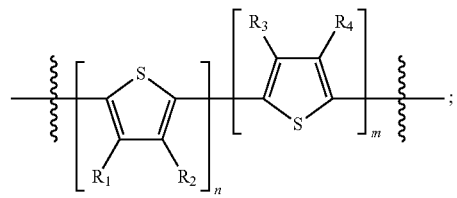

each $L_3$ is, independently, —$B_2$ or -$A_1$-$B_2$ each $A_1$ is independently selected from substituted or unsubstituted aryl group, substituted or unsubstituted heteroaryl group,

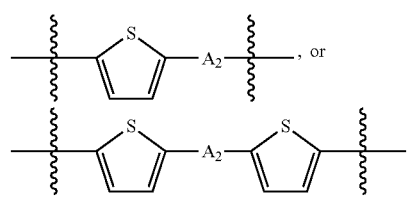

where $A_2$ is independently a substituted or unsubstituted aryl group or substituted or unsubstituted heteroaryl group;

each $B_2$ is independently selected from H, a substituent, halogen, —Sn($C_1$-$C_4$ alkyl)$_4$, —Zn(halide),

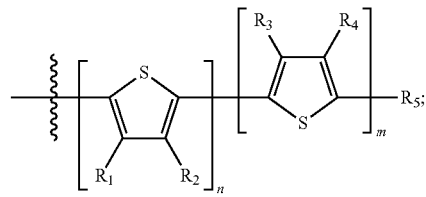

—Mg(halide), —B(OH)$_2$, or boronate ester, or where n is an integer between 0 and 5, inclusive and m is an integer between 0 and 5, inclusive, and $1 \leq m+n \leq 5$; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

16. A compound of claim 15, having Formula IVa

Formula IVa

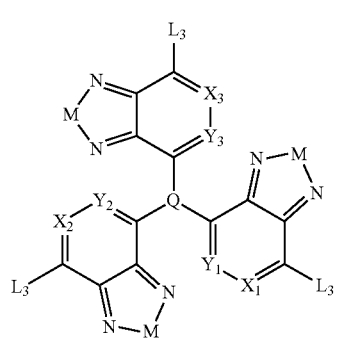

where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N—R$_1$)—;

where R$_1$ is H or a substituent;

R$_6$ is H or a substituent;

R$_7$ is H or a substituent;

R$_8$ is H or a substituent;

X$_1$ is N or C—R$_9$, Y$_1$ is N or C—R$_9$, one of X$_1$ and Y$_1$ is N, and the other is C—R$_9$; where R$_9$ is F, Cl, Br, or I;

X$_2$ is N or C—R$_9$, Y$_2$ is N or C—R$_9$, one of X$_2$ and Y$_2$ is N, and the other is C—R$_9$; where R$_9$ is F, Cl, Br, or I;

X$_3$ is N or C—R$_9$, Y$_3$ is N or C—R$_9$, one of X$_3$ and Y$_3$ is N, and the other is C—R$_9$; where R$_9$ is F, Cl, Br, or I;

Q is a trivalent aryl or heteroaryl group;

each L$_3$ is, independently, —B$_2$ or -A$_1$-B$_2$ each A$_1$ is independently selected from substituted or unsubstituted aryl group, substituted or unsubstituted heteroaryl group,

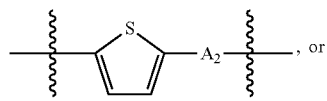, or

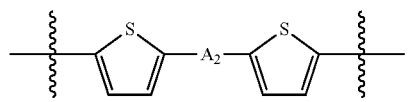

where A$_2$ is independently a substituted or unsubstituted aryl group or substituted or unsubstituted heteroaryl group;

each B$_2$ is independently selected from H, a substituent, halogen, —Sn(C$_1$-C$_4$ alkyl)$_4$, —Zn(halide), —Mg(halide), B(OH)$_2$, or boronate ester, or

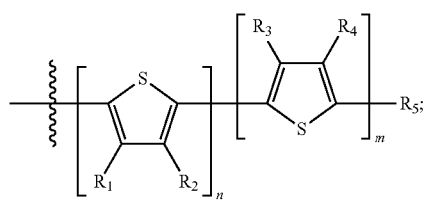

where n is an integer between 0 and 5, inclusive and m is an integer between 0 and 5, inclusive, and 1 m+n≤5; and where R$_1$, R$_2$, R$_3$, and R$_4$ are each independently H or a substituent, R$_5$ is H, a substituent, halogen, —Sn(C$_1$-C$_4$ alkyl)$_3$, —Zn(halide), —Mg(halide), —B(OH)$_2$, or boronate ester.

17. A compound of claim 15, of Formula Va:

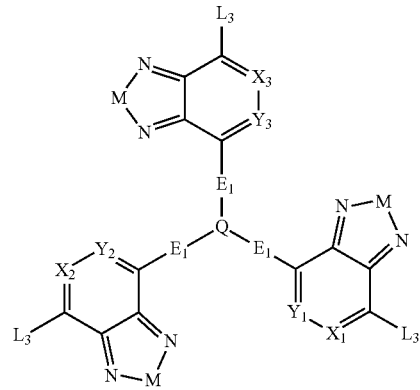

Formula Va where M is selected from sulfur (S), oxygen (O), selenium (Se), tellurium (Te), —N(R$_6$)—, —C(R$_7$)$_2$—C(R$_8$)$_2$—, —CR$_7$=CR$_8$—, —S(=O)$_2$—, —S(=O)—, —C(=O)—, —C(=S)—, or —C(=N—R$_1$)—;

where R$_1$ is H or a substituent;

R$_6$ is H or a substituent;

R$_7$ is H or a substituent;

R$_8$ is H or a substituent;

X$_1$ is N or C—R$_9$, Y$_1$ is N or C—R$_9$, one of X$_1$ and Y$_1$ is N, and the other is C—R$_9$; where R$_9$ is F, Cl, Br, or I;

X$_2$ is N or C—R$_9$, Y$_2$ is N or C—R$_9$, one of X$_2$ and Y$_2$ is N, and the other is C—R$_9$; where R$_9$ is F, Cl, Br, or I;

X$_3$ is N or C—R$_9$, Y$_3$ is N or C—R$_9$, one of X$_3$ and Y$_3$ is N, and the other is C—R$_9$; where R$_9$ is F, Cl, Br, or I;

Q is a trivalent aryl or heteroaryl group;

each E$_1$ is independently either substituted or unsubstituted aryl, substituted or unsubstituted heteroaryl groups, or

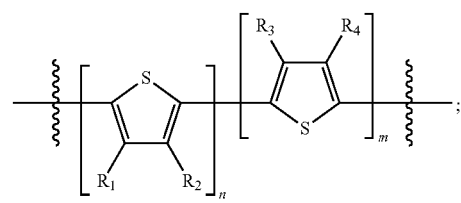;

each L$_3$ is, independently, —B$_2$ or -A$_1$-B$_2$ each A$_1$ is independently selected from substituted or unsubstituted aryl group, substituted or unsubstituted heteroaryl group,

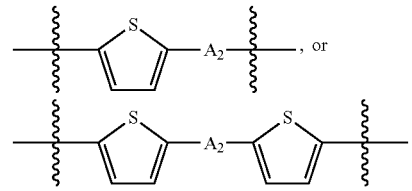, or where A₂ is independently a substituted or unsubstituted aryl group or substituted or unsubstituted heteroaryl group;

each B₂ is independently selected from H, a substituent, halogen, —Sn(C₁-C₄ alkyl)₄, —Zn(halide), —Mg(halide), —B(OH)₂, or boronate ester, or

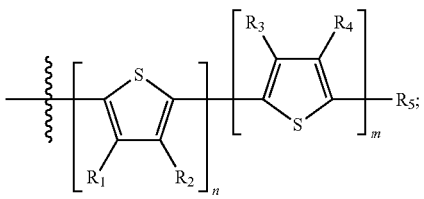

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_5$ is H, a substituent, halogen, —Sn(C₁-C₄ alkyl)₃, —Zn(halide), —Mg(halide), —B(OH)₂, or boronate ester.

18. A compound having Formula VI-VII:

Formula VI-VII

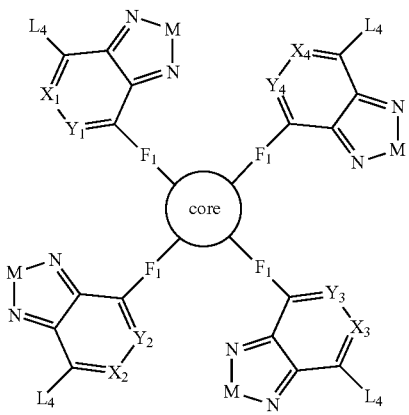

where the moiety

is a tetravalent aryl or heteroaryl group selected from

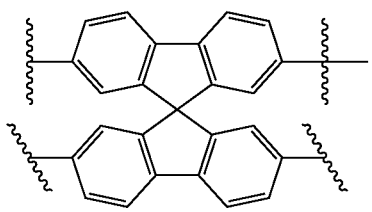 [SMILES: *c1ccc2c(c1)C1(c3cc(*)ccc3-2)c2cc(*)ccc2-c2ccc(*)cc21]

(2, 2',7,7'-yl-9,9'-spirobi[fluorene]),

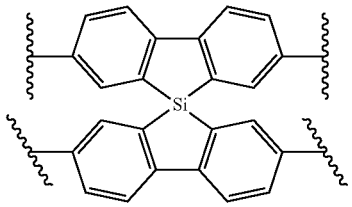 [SMILES: *c1ccc2c(c1)[Si]1(c3cc(*)ccc3-2)c2cc(*)ccc2-c2ccc(*)cc21]

(3,3',7,7'-yl-5,5'-spirobi[dibenzo[b,d]silole]),

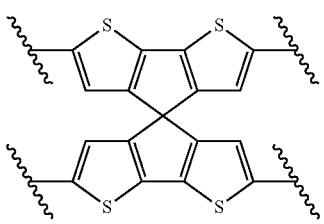 [SMILES: *c1cc2c(s1)-c1sc(*)cc1C21c2cc(*)sc2-c2sc(*)cc21]

(2,2',6,6'-yl-4,4''-spirobi[cyclopenta[1,2-b:5,4-b']dithiophene]), or

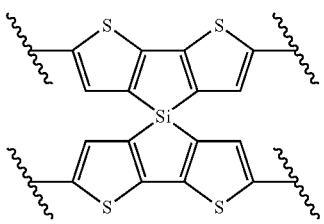 [SMILES: *c1cc2c(s1)-c1sc(*)cc1[Si]21c2cc(*)sc2-c2sc(*)cc21]

(2,2',6,6'-yl-4,4'-spirobi[silolo[3,2-b:4,5-b']dithiophene]);

where M is selected from sulfur (S), oxygen (O), selenium (Se), tellurium (Te), —N(R₆)—, —C(R₇)₂—C(R₈)₂—, —CR₇=CR₈—, —S(=O)₂—, —S(=O)—, —C(=O)—, —C(=S)—, or —C(=N—R₁)—;

where $R_1$ is H or a substituent;

$R_6$ is H or a substituent;

$R_7$ is H or a substituent;

$R_8$ is H or a substituent;

$X_1$ is N or C—R₉, $Y_1$ is N or C—R₉, one of $X_1$ and $Y_1$ is N, and the other is C—R₉; where $R_9$ is F, Cl, Br, or I;

$X_2$ is N or C—R₉, $Y_2$ is N or C—R₉, one of $X_2$ and $Y_2$ is N, and the other is C—R₉; where $R_9$ is F, Cl, Br, or I;

$X_3$ is N or C—R₉, $Y_3$ is N or C—R₉, one of $X_3$ and $Y_3$ is N, and the other is C—R₉; where $R_9$ is F, Cl, Br, or I;

$X_4$ is N or C—R₉, $Y_4$ is N or C—R₉, one of $X_4$ and $Y_4$ is N, and the other is C—R₉; where $R_9$ is F, Cl, Br, or I;

each $F_1$ is independently either nonentity, substituted or unsubstituted aryl, substituted or unsubstituted heteroaryl groups, or

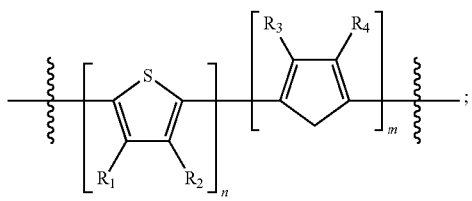

each $L_4$ is, independently, —$B_2$ or -$A_1$-$B_2$;
each $A_1$ is independently selected from substituted or unsubstituted aryl group, substituted or unsubstituted heteroaryl group

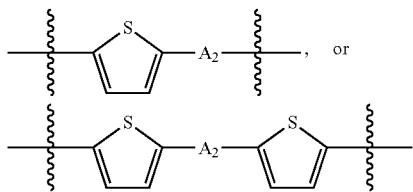

where $A_2$ is independently a substituted or unsubstituted aryl group or substituted or unsubstituted heteroaryl group;
each $B_2$ is independently selected from H, a substituent, halogen, —Sn($C_1$-$C_4$ alkyl)$_4$, —Zn(halide), —Mg(halide), —B(OH)$_2$, or boronate ester, or

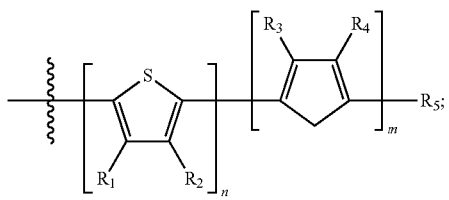

where n is an integer between 0 and 5, inclusive and m is an integer between 0 and 5, inclusive, and $1 \le m+n \le 5$; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

19. A compound of claim 18, of Formula VIa:

Formula VIa

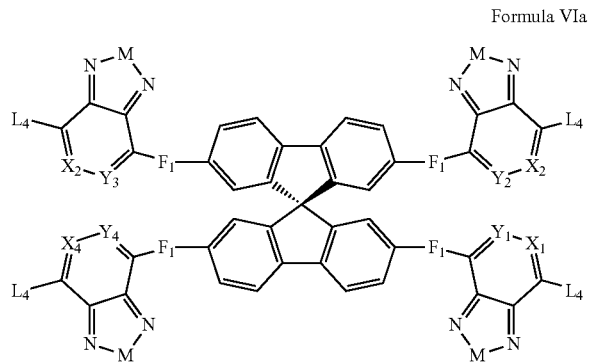

where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N-$R_1$)—;
where $R_1$ is H or a substituent;
$R_6$ is H or a substituent;
$R_7$ is H or a substituent;
$R_8$ is H or a substituent;
$X_1$ is N or C—$R_9$, $Y_1$ is N or C—$R_9$, one of $X_1$ and $Y_1$ is N, and the other is C—$R_9$; where $R_9$ is F, Cl, Br, or I;
$X_2$ is N or C—$R_9$, $Y_2$ is N or C—$R_9$, one of $X_2$ and $Y_2$ is N, and the other is C—$R_9$; where $R_9$ is F, Cl, Br, or I;
$X_3$ is N or C—$R_9$, $Y_3$ is N or C—$R_9$, one of $X_3$ and $Y_3$ is N, and the other is C—$R_9$; where $R_9$ is F, Cl, Br, or I;
$X_4$ is N or C—$R_9$, $Y_4$ is N or C—$R_9$, one of $X_4$ and $Y_4$ is N, and the other is C—$R_9$; where $R_9$ is F, Cl, Br, or I;
each $F_1$ is independently either nonentity, substituted or unsubstituted aryl, substituted or unsubstituted heteroaryl groups, or

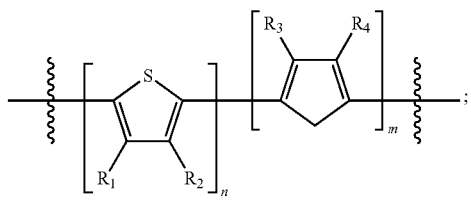

each $L_4$ is, independently, —$B_2$ or -$A_1$-$B_2$;
each $A_1$ is independently selected from substituted or unsubstituted aryl group, substituted or unsubstituted heteroaryl group,

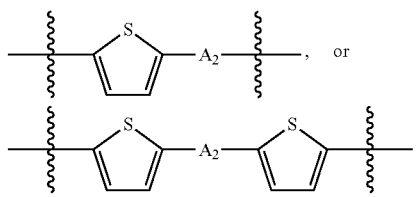

where $A_2$ is independently a substituted or unsubstituted aryl group or substituted or unsubstituted heteroaryl group;
each $B_2$ is independently selected from H, a substituent, halogen, —Sn($C_1$-$C_4$ alkyl)$_4$, —Zn(halide), —Mg(halide), —B(OH)$_2$, or boronate ester, or

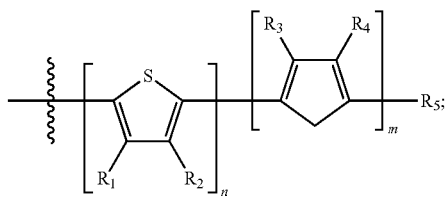

where n is an integer between 0 and 5, inclusive and m is an integer between 0 and 5, inclusive, and $1 \le m+n \le 5$;

and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester.

20. A compound of claim 18, of Formula VIIa:

Formula VIIa

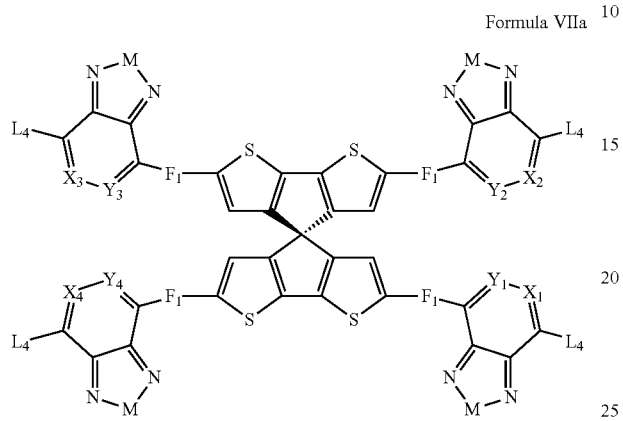

where M is selected from sulfur (S), oxygen (O), selenium (Se), tellurium (Te), —N($R_6$)—, —C($R_7$)$_2$—C($R_8$)$_2$—, —$CR_7$=$CR_8$—, —S(=O)$_2$—, —S(=O)—, —C(=O)—, —C(=S)—, or —C(=N—$R_1$)—;

where $R_1$ is H or a substituent;

$R_6$ is H or a substituent;

$R_7$ is H or a substituent;

$R_8$ is H or a substituent;

$X_1$ is N or C—$R_9$, $Y_1$ is N or C—$R_9$, one of $X_1$ and $Y_1$ is N, and the other is C—$R_9$; where $R_9$ is F, Cl, Br, or I;

$X_2$ is N or C—$R_9$, $Y_2$ is N or C—$R_9$, one of $X_2$ and $Y_2$ is N, and the other is C—$R_9$; where $R_9$ is F, Cl, Br, or I;

$X_3$ is N or C—$R_9$, $Y_3$ is N or C—$R_9$, one of $X_3$ and $Y_3$ is N, and the other is C—$R_9$; where $R_9$ is F, Cl, Br, or I;

$X_4$ is N or C—$R_9$, $Y_4$ is N or C—$R_9$, one of $X_4$ and $Y_4$ is N, and the other is C—$R_9$; where $R_9$ is F, Cl, Br, or I;

each $F_1$ is independently either nonentity, substituted or unsubstituted aryl, substituted or unsubstituted heteroaryl groups, or

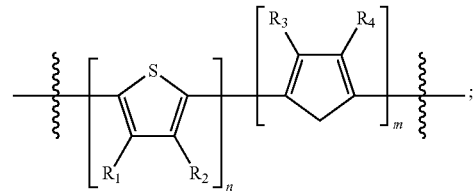

each $L_4$ is, independently, —$B_2$ or -$A_1$-$B_2$;

each $A_1$ is independently selected from substituted or unsubstituted aryl group, substituted or unsubstituted heteroaryl group,

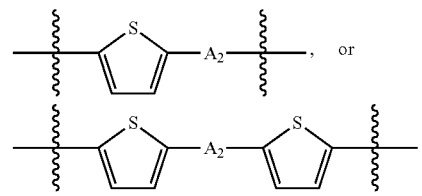

where $A_2$ is independently a substituted or unsubstituted aryl group or substituted or unsubstituted heteroaryl group;

each $B_2$ is independently selected from H, a substituent, halogen, —Sn($C_1$-$C_4$ alkyl)$_4$, —Zn(halide), —Mg(halide), —B(OH)$_2$, or boronate ester, or

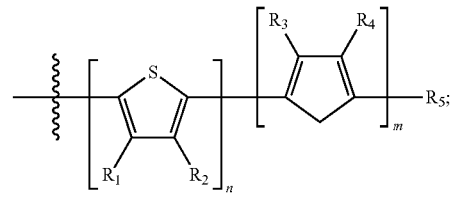

where n is an integer between 0 and 5, inclusive and m is an integer between 0 and 5, inclusive, and 1≤m+n≤5; and where $R_1$, $R_2$, $R_3$, and $R_4$ are each independently H or a substituent, $R_5$ is H, a substituent, halogen, —Sn($C_1$-$C_4$ alkyl)$_4$, —Zn(halide), —Mg(halide), —B(OH)$_2$, or boronate ester.

21. A compound selected from Formula 1, Formula 2, Formula 3, Formula 4, Formula 5, Formula 6, Formula 7, Formula 8, Formula 9 or Formula 10:

1

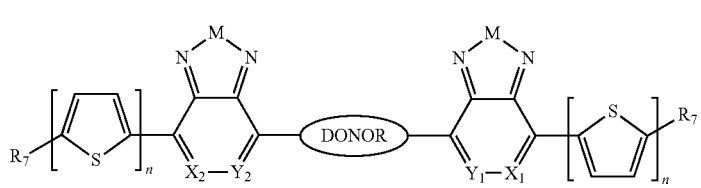

-continued
2
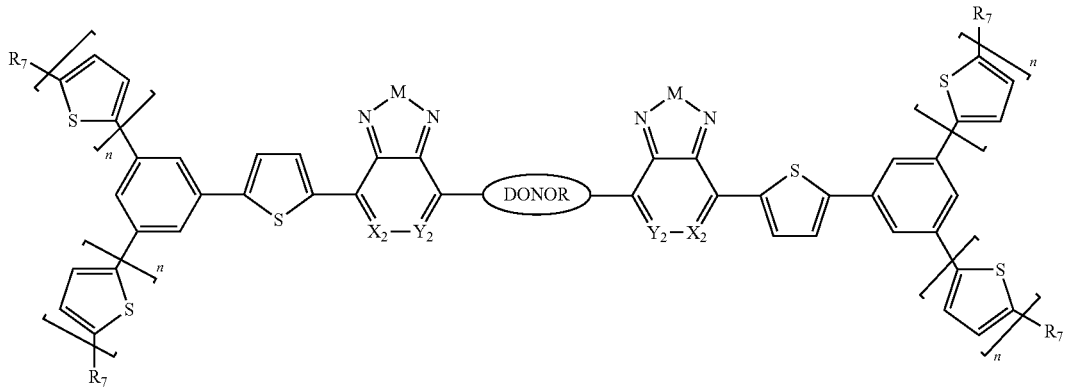
3
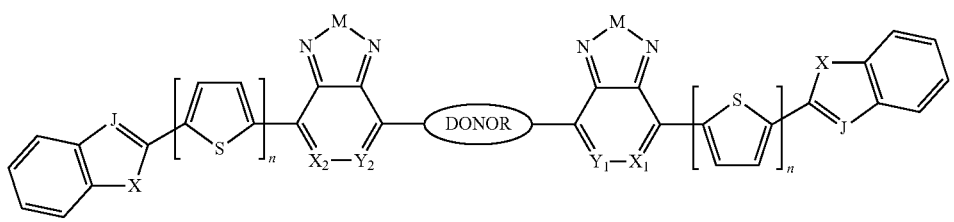
4
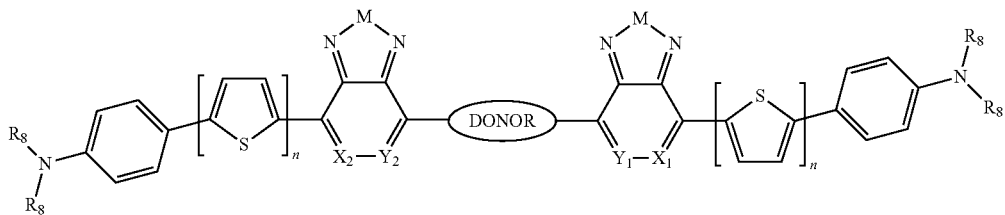
5
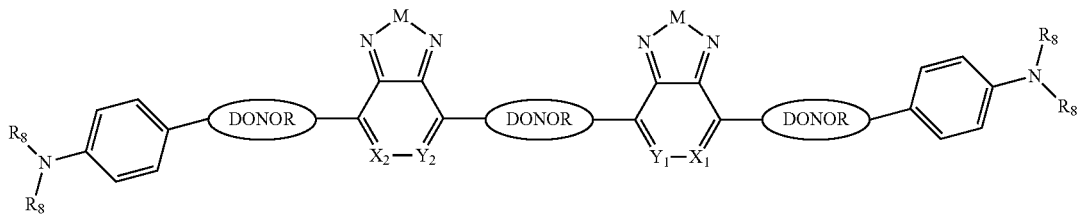
6
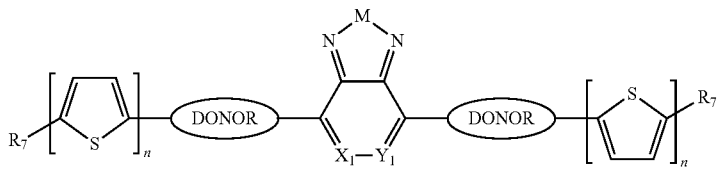
7
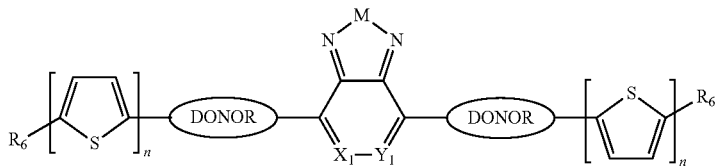
8
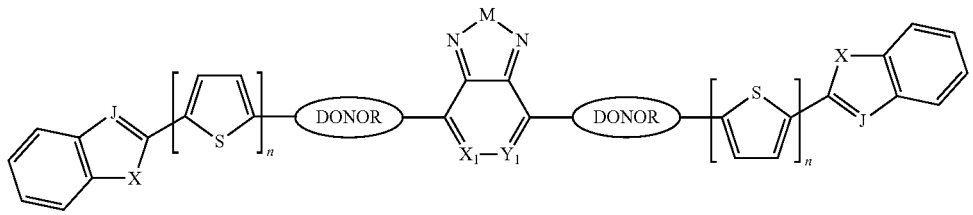

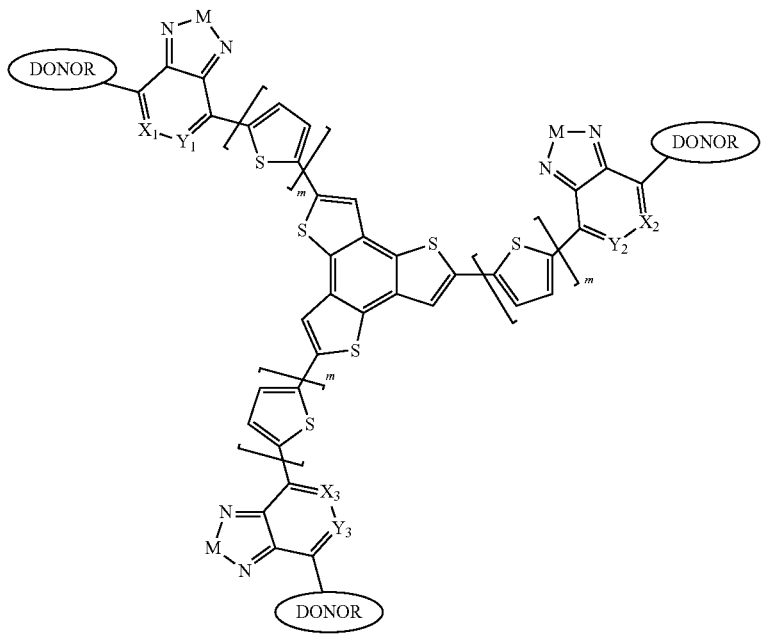

9

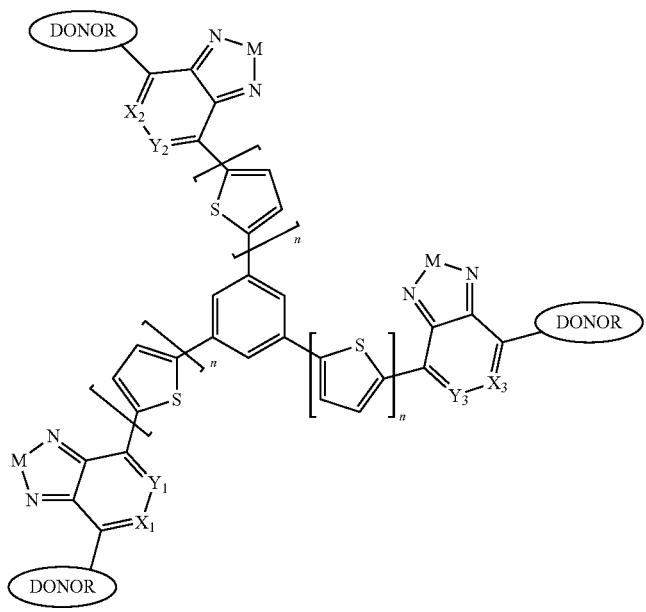

10 where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—;

where $R_1$ is H or a substituent;

$R_6$ is H or a substituent;

$R_7$ is H or a substituent;

$R_8$ is H or a substituent;

$X_1$ is N or C—$R_9$, $Y_1$ is N or C—$R_9$, one of $X_1$ and $Y_1$ is N, and the other is C—$R_9$; where $R_9$ is F, Cl, Br, or I;

$X_2$ is N or C—$R_9$, $Y_2$ is N or C—$R_9$, one of $X_2$ and $Y_2$ is N, and the other is C—$R_9$; where $R_9$ is F, Cl, Br, or I;

$X_3$ is N or C—$R_9$, $Y_3$ is N or C—$R_9$, one of $X_3$ and $Y_3$ is N, and the other is C—$R_9$; where $R_9$ is F, Cl, Br, or I;

n is an integer from 0 to 5 inclusive; m is an integer from 0 to 5 inclusive;

$R_7$ is selected from H or a substituent;

J is selected from CH and N;

X is S, O, or NH when X is CH; and X is S when J is N;

$R_8$ is $C_6$-$C_{30}$ aryl optionally substituted with one or more $C_1$-$C_{16}$ alkyl groups;

$R_6$ is selected from aryl, perfluoroaryl, or $C_6$-$C_{30}$ aryl optionally perfluorinated or optionally substituted with one or more $C_1$-$C_{16}$ alkyl groups; and each DONOR is an aryl or heteroaryl group independently selected from:

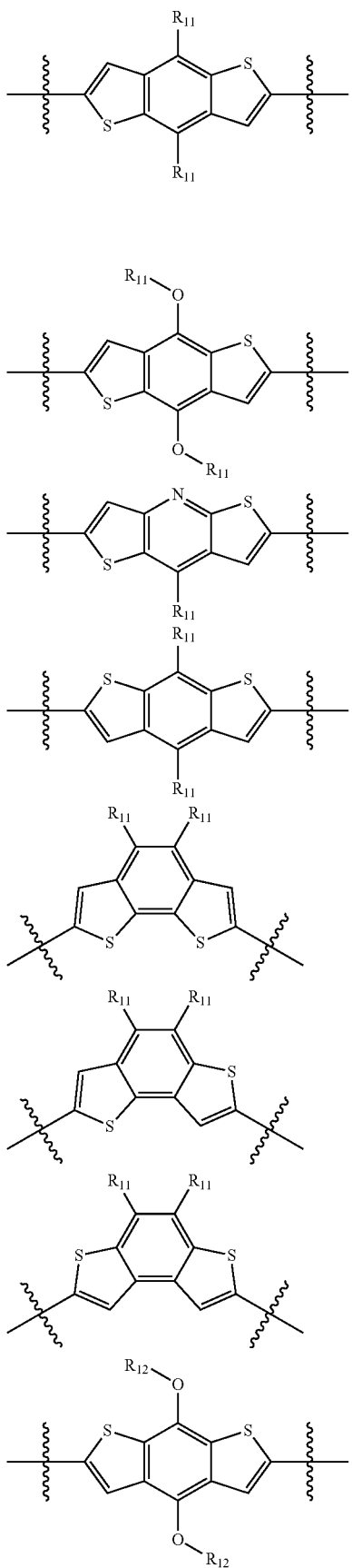
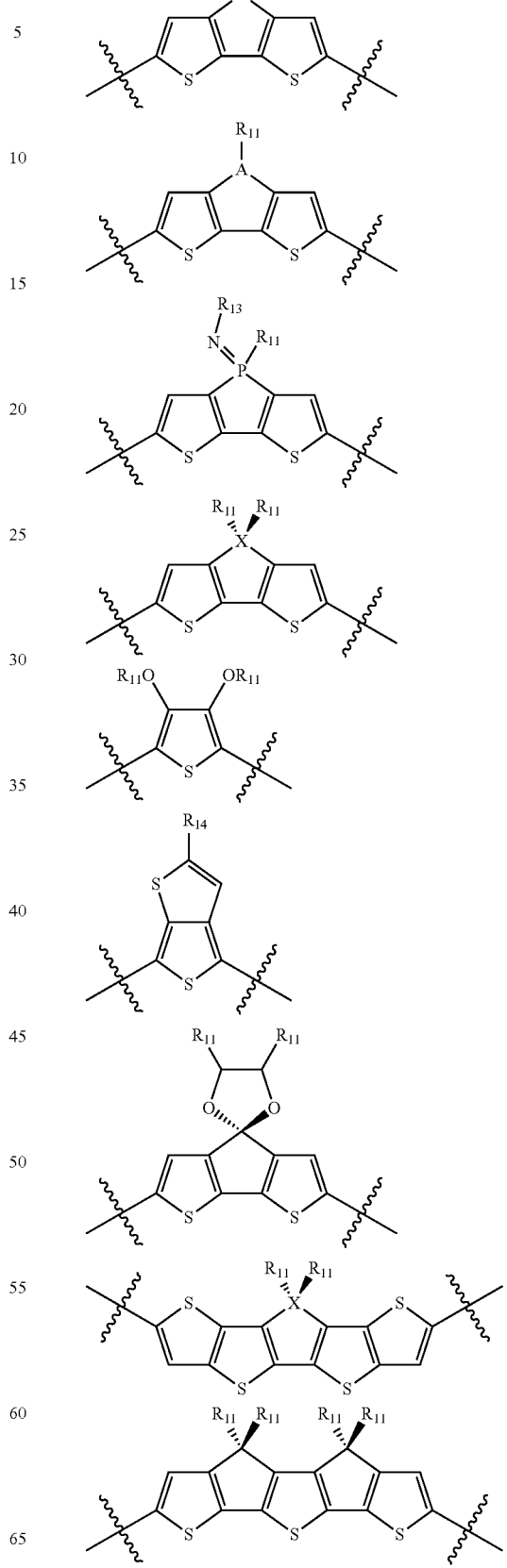

-continued

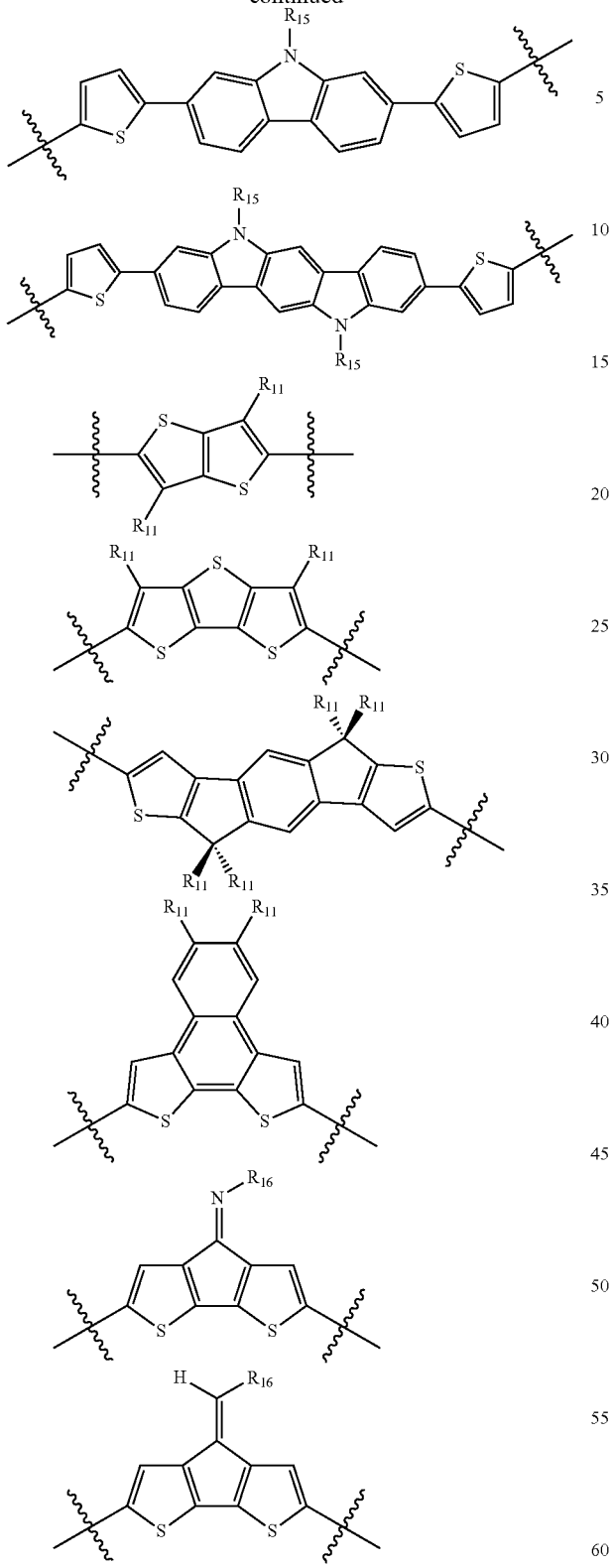

where X is C or Si;
A is N or P;
$R_{11}$ is selected from $C_1$-$C_{16}$ alkyl;
$R_{12}$ is selected from $C_1$-$C_{16}$ alkyl, C6-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl;

$R_{13}$ is selected from $C_1$-$C_{16}$ alkyl or $C_6$-$C_{20}$ aryl;

$R_{14}$ is selected from $C_1$-$C_{16}$ alkyl, —O—C—$C_{16}$ alkyl, —C(=O)—O—$C_1$-$C_{16}$ alkyl, or —O—C(=O)—$C_1$-$C_{16}$ alkyl; and $R_{15}$ is selected from $C_1$-$C_{16}$ alkyl, $C_6$-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl; and $R_{16}$ is selected from $C_1$-$C_{16}$ alkyl, $C_6$-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl.

22. A compound of Formula B:

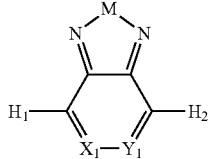

Formula B where M is selected from sulfur (S), oxygen (O), selenium (Se), tellurium (Te), —N($R_6$)—, —C($R_7$)$_2$—C($R_8$)$_2$—, —C$R_7$=C$R_8$—, —S(=O)$_2$—, —S(=O)—, —C(=O)—, —C(=S)—, or —C(=N—$R_1$)—;

where $R_1$ is H or a substituent;

$R_6$ is H or a substituent;

$R_7$ is H or a substituent;

$R_8$ is H or a substituent;

$X_1$ is N or C—$R_9$, $Y_1$ is N or C—$R_9$, and one of $X_1$ and $Y_1$ is N, and the other is C—$R_9$; where $R_9$ is F, Cl, Br, or I;

$H_1$ is selected from -$A_1$-$B_1$, -$A_1$-$B_2$, or

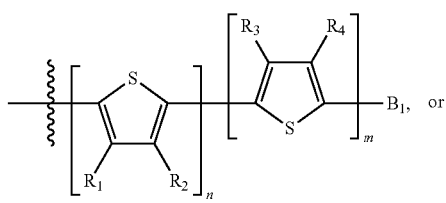

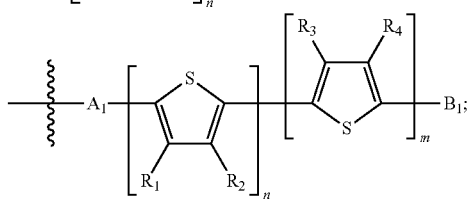

n is an integer between 0 and 5, inclusive and m is an integer between 0 and 5, inclusive, and $1 \le m+n \le 5$;

$A_1$ is independently selected from substituted or unsubstituted aryl group, substituted or unsubstituted heteroaryl group,

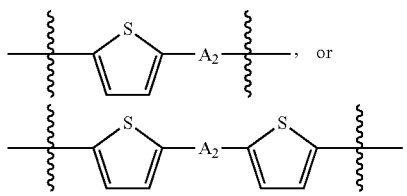, or where $A_2$ is independently a substituted or unsubstituted aryl group or substituted or unsubstituted heteroaryl group;

each $B_1$ is independently selected from a an aryl or heteroaryl groups substituted with one, two, or more $B_2$; and each $B_2$ is independently selected from a substituent, halogen, —Sn($C_1$-$C_4$ alkyl)$_4$, —Zn(halide), —Mg(halide), —B(OH)$_2$, or boronate ester, or

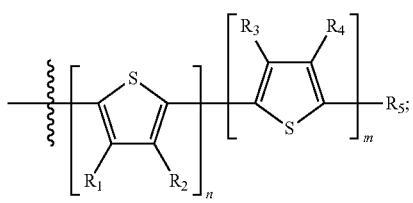

where n is an integer between 0 and 5, inclusive and m is an integer between 0 and 5, inclusive, and $1 \le m+n \le 5$; and where $R_1$, $R_2$, $R_3$, and $R_4$ are each independently H or a substituent, $R_5$ is H, a substituent, halogen, —Sn($C_1$-$C_4$ alkyl)$_3$, —Zn(halide), —Mg(halide), —B(OH)$_2$, or boronate ester;

$H_2$ is selected from —$B_2$, -$A_1$-$B_1$, -$A_1$-$B_2$,

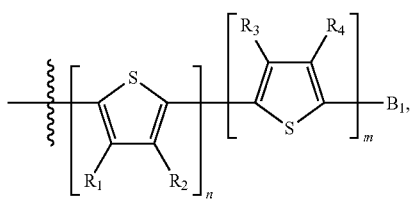

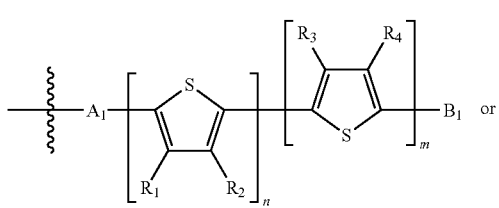

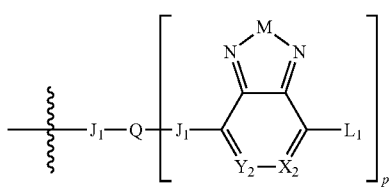

where p is 1, 2, or 3;

each $X_2$ is N or C—$R_9$, $Y_2$ is N or C—$R_9$, one of $X_2$ and $Y_2$ is N, and the other is C—$R_9$;

where $R_9$ is F, Cl, Br, or I;

each $J_1$ is independently selected from a nonentity, substituted or unsubstituted aryl, substituted or unsubstituted heteroaryl groups, or

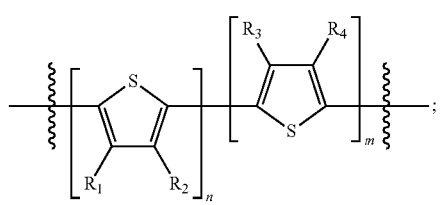

Q is a bivalent, trivalent, or tetravalent aryl or heteroaryl group or

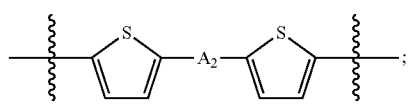

$L_1$ is selected from —$B_2$, -$A_1$-$B_1$, -$A_1$-$B_2$,

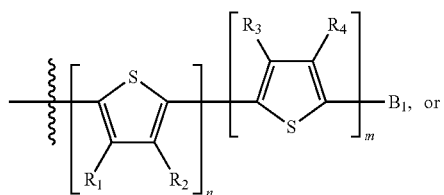

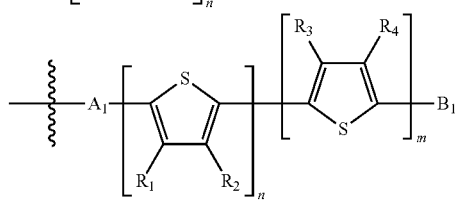

where each $A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups; wherein the compound is a polymer.

23. A compound according to claim 2, where $R_1$, $R_2$, $R_3$, $R_4$, $R_5$ are each independently halogen, F, $NO_2$, CN, acyl, O-acyl, S-acyl, N-acyl, alkyl, haloalkyl, substituted or unsubstituted aryl, substituted or unsubstituted heteroaryl, alkenyl, alkoxy, alkylthio, alkylamine, arylamine, or hydroxy.

24. A compound according to claim 2, where at least one of $R_1$, $R_2$, $R_3$, or $R_4$ is alkyl.

25. A compound according to claim 2, wherein all $R_9$ are F.

26. A compound according to claim 2, wherein M is S.

27. An electronic or optoelectronic device comprising a non-polymeric compound of claim 2.

28. An electronic or optoelectronic device according to claim 27, wherein said device is a solar cell.

29. An electronic or optoelectronic device according to claim 27, wherein said group of Formula A is a pyridothiadiazole group, pyridooxadizaole group, or pyridotriazole group.

30. A device of claim 27, comprising a first electrode, a second electrode and an active layer between the first and second electrode, where the active layer comprises the non-polymeric compound.

31. A device of claim 30, where one electrode is transparent.

32. A device of claim 30, further comprising an electron-blocking, exciton-blocking, or hole-transporting layer.

33. A device of claim 30, further comprising a hole-blocking, exciton-blocking, or electron-transporting layer.

34. A device of claim 33, where the active layer further comprises an electron acceptor.

35. A device of claim 34, where the electron acceptor is a fullerene.

36. A device of claim 30, further comprising a dielectric layer.

37. A device of claim 30, further comprising a third electrode.

38. An electronic or optoelectronic device of claim 27, comprising:
- a first electrode;
- a second electrode spaced apart from said first electrode; and
- an active layer between said first electrode and said second electrode, wherein said active layer comprises the non-polymeric compound.

39. An electronic or optoelectronic device of claim 38, further comprising a hole transporting layer between said first electrode and said active layer.

\* \* \* \* \*